(12) United States Patent
Rozenblat et al.

(10) Patent No.: US 10,226,499 B2
(45) Date of Patent: Mar. 12, 2019

(54) PLANT EXTRACTS FOR THE TREATMENT AND PREVENTION OF INFECTIONS

(75) Inventors: Sharon Rozenblat, Tel-Aviv (IL); DaiHyun Jung, Gwangsan-Gu (KR); SangHyun Moh, Yongin-si (KR); SuJung Kim, Gwangsan-Gu (KR); JungHun Lee, Seoul (KR)

(73) Assignees: KAMEDIS LTD., Tel Aviv (IL); BIO-FD&C CO. LTD., Jeonnam, Hwasun-Gun (KR)

( * ) Notice: Subject to any disclaimer, the term of this patent is extended or adjusted under 35 U.S.C. 154(b) by 0 days.

(21) Appl. No.: 13/976,638

(22) PCT Filed: Dec. 28, 2011

(86) PCT No.: PCT/IL2011/050081
§ 371 (c)(1),
(2), (4) Date: Jun. 27, 2013

(87) PCT Pub. No.: WO2012/090205
PCT Pub. Date: Jul. 5, 2012

(65) Prior Publication Data
US 2013/0323335 A1    Dec. 5, 2013

Related U.S. Application Data

(60) Provisional application No. 61/427,495, filed on Dec. 28, 2010.

(51) Int. Cl.
| *A61K 36/71* | (2006.01) |
| *A61K 36/739* | (2006.01) |
| *A61K 36/484* | (2006.01) |
| *A61K 36/539* | (2006.01) |
| *A61K 36/708* | (2006.01) |
| *A61K 36/185* | (2006.01) |
| *A61K 36/28* | (2006.01) |

(52) U.S. Cl.
CPC .......... *A61K 36/739* (2013.01); *A61K 36/185* (2013.01); *A61K 36/28* (2013.01); *A61K 36/484* (2013.01); *A61K 36/539* (2013.01); *A61K 36/708* (2013.01)

(58) Field of Classification Search
CPC .................................................. A61K 36/739
See application file for complete search history.

(56) References Cited

U.S. PATENT DOCUMENTS

| 3,755,560 A | 8/1973 | Dickert et al. |
| 4,421,769 A | 12/1983 | Dixon et al. |
| 4,665,201 A | 5/1987 | Honda |
| 4,774,342 A | 9/1988 | Honda |
| 5,466,452 A | 11/1995 | Whittle |
| 5,658,247 A | 8/1997 | Henley |
| 5,667,487 A | 9/1997 | Henley |
| 6,143,498 A | 11/2000 | Olsen |
| 6,235,287 B1 | 5/2001 | Weidner |
| 6,329,340 B1 | 12/2001 | Bougueleret |
| 6,335,318 B1 | 1/2002 | Selsted |
| 6,420,116 B1 | 7/2002 | Olsen |
| 6,566,405 B2 | 5/2003 | Weidner |
| 6,676,975 B2 | 1/2004 | Whittle |
| 6,911,577 B2 | 6/2005 | Simmons |
| 7,211,567 B1 | 5/2007 | Kotani |
| 7,223,840 B2 | 5/2007 | Olsen |
| 7,252,845 B2 | 8/2007 | Weidner |
| 2006/0036083 A1 | 2/2006 | Moss |
| 2006/0147442 A1 | 7/2006 | Homan |
| 2007/0104722 A1 | 5/2007 | Imboden |

FOREIGN PATENT DOCUMENTS

| CN | 1380098 A | 11/2002 |
| CN | 1883588 | 12/2006 |
| CN | 1943768 | 4/2007 |
| CN | 101073260 | 11/2007 |
| CN | 101254251 | 9/2008 |
| CN | 101279024 | 10/2008 |
| CN | 101342322 | 1/2009 |
| CN | 101444596 | 6/2009 |
| JP | 2009235049 | 10/2009 |
| KR | 20060033070 | 4/2006 |
| KR | 20060130830 | 12/2006 |
| KR | 20070016352 | 2/2007 |
| KR | WO2010/078419 | 7/2010 |

OTHER PUBLICATIONS

Ahn et al. (2005) Pesticide Biochemistry and Physiology 81; 105-112.*
Akamatsu et al. (1991) Planta Med. 57; 119-121.*
Bray et al. (1987) Phytotherapy Research, vol. 1, No. 1, 22-24.*
Cha et al. (2013) J. Fd Hyg. Safety vol. 28, No. 2, pp. 95-98.*
Chung et al. (1995) Phytotherapy Research, vol. 9, 429-434.*
Revilla et al. (1998) J. Agric. Food Chem. 46, 4592-4597.*
De Feo et al. (2005) Phytother. Res. 19, 226-230.*
Jin et al. (2006) Biol. Pharm. Bull. 29(5): 884-888.*
Kim et al. (2001) Phytother. Res. 15, 718-720.*
Lee et al. (2010) Lab. Anim. Res. 26(3), 257-263.*
Lee et al. (2011) J. Ethnopharma. 138, 602-609.*

(Continued)

*Primary Examiner* — Christopher R Tate
*Assistant Examiner* — Russell G Fiebig
(74) *Attorney, Agent, or Firm* — Pearl Cohen Zedek Latzer Baratz LLP

(57) ABSTRACT

A composition comprising a *Sanguisorbae officinalis* plant extract and at least one additional plant extract selected from the group consisting of an *Ailanthus altissima* plant extract, a *Galla rhois* gallnut plant extract, a *Glycyrrhiza Glabra* plant extract, a *Rheum palmatum* plant extract and a *Scutellaria baicalensis* plant extract is disclosed. Compositions comprising *Ailanthus altissima* plant extract or Ailanthone are also disclosed.

4 Claims, 52 Drawing Sheets

(56) References Cited

OTHER PUBLICATIONS

Lee et al. (2005) J. Ethnopharma. 96, 211-219.*
Leung et al. (2004) J. Clin. Invest. vol. 113, No. 5, 651-657.*
Yu et al. (2011) J. Ethnopharma. 134, 11-17.*
Zhao et al. (2005) Arch. Pharm Res. vol. 28, No. 10, 1147-1151.*
Baltina et al. (2009) Pharmaceutical Chemistry Journal vol. 43, No. 10. pp. 539-548.*
Zhang et al. (2012) Int. J. Biological Macromolecules 51: 1057-1062.*
Albanesi C. et al.,"IL-4 and IL-13 Negatively Regulate TNF-a- and IFN-y- Induced B-Defensin Expression through STAT-6, Suppressor of Cytokine Signaling (SOCS)- and SOCS-3" Journal of Immunology (2007) 179(2): 984-992.
Nomura I. et al., "Cytokine Milieu of Atopic Dermatitis, as Compared to Psoriasis, Skin Prevents Induction of Innate Immune Response Genes" Journal of Immunology, (2003) 171(6), 3262-3269.
Na HJ. et al.,"Regulatory Effects of Cytokine Production in Atopic Allergic Reaction by Gammi-Danguieumja ", Inflammation (2004) 28, 291-297.
Kawai, M. et al.,"Flavonoids and Related Compounds as Anti-Allergic Substances" Allergology International (2007) 56:113-123.
Hua Jin, M. et al., "Anti-inflammatory Activity of Ailanthus altissima in Ovalbumin Induced Lung Inflammation" Biol. Pharm. Bull. (2006) 29: 884-888.
Ram A et al., "Glycyrrhizin alleviates experimental allergic asthma in mice", International Immunopharacol, (2006) 6(9):1468-1477.
Kim CD et al., "Inhibition of Mast Cell-Dependent Allergy Reaction by Extract of Black Cohosh (*Cimicifuga racemosa*)", Immunopharmacol Immunotoxicol (2004) 26: 299-308.
Goh et al. "Skin colonization of *Staphylococcus aureus* in atopic dermatitis patients seen at the National Skin Centre, Singapore." Int J Dermatol. (1997) 36(9):653-7.
Swanson RL et al., "Induction of Settlement of Larvae of the Sea Urchin *Holopneustes purpurascens* by Histamine From a Host Alga" 2004, Biol. Bull. 206: 161-72.
NG LK and Hupe M."Effects of moisture content in cigar tobacco on nicotine extraction. Similarity between soxhlet and focused open-vessel microwave-assisted techniques" 2003, J. Chromatogr A. 1011: 213-9.
Diwanay S, et al., "Immunoprotection by botanical drugs in cancer chemotherapy" 2004, J. Ethnopharmacol. 90: 49-55.
Harder et al., "A peptide antibiotic from human skin" Nature (1997) 387: 861.
Harder et al., "Isolation and Characterization of Human B-Defensin-3, a Novel Human Inducible Peptide Antibiotic" J Biol Chem (2001) 276: 5707-13.
Xuejun Chen et al., "Synergistic effect of antibacterial agents human B-defensins, cathelicidin LL-37 and lysozymeagainst *Staphylococcus aureus* and *Escherichia coli* " J. Dermatol. Science (2005) 40(2), 123-132.
Search Report for International Application No. PCT/IL2011/050081 dated Aug. 2012.
Jin M. H et al.: "Antiinflammatory activity of Ailanthus altissima in ovalbumin-induced lung inflammation" Medicinal & Aromatic Plants Abstracts, vol. 28, No. 5, Oct. 1, 2006, Scientific Publishers, New Delhi, India.
Jin M. H et al.: "Anti-inflammatory activity of Ailanthus altissima in ovalbumin-induced lung inflammation" Biological & Pharmaceutical Bulletin (of Japan), vol. 29, No. 5, May 1, 2006, p. 884-888, Pharmaceutical Society of Japan, Tokyo, Japan.
Jin M. H et al.: "Antiasthmatic activity of luteolin-7-0-glucoside from Ailanthus altissima through the downregulation of T helper 2 cytokine expression and inhibition of prostaglandin E2 production in an ovalbumin-induced asthma model", Medicinal & Aromatic Plants Abstracts, vol. 32, No. 1. Feb. 1, 2010, Scientific Publishers, New Delhi, India.
Tae Gyun Kim et al.: "Antiviral activities of extracts isolated from *Terminalis chebula* Retz., *Sanguisorba officinalis* L., *Rubus coreanus* Miq. and *Rheum palmatum* L. against hepatitis B virus", Phytotherapy Research , vol. 15, No. 8, 2001, pp. 718-720.
Tae Gyum Kim et al. "Inhibitory effects of Teminalia chebula, Sanguisorba officinalis, Rubus coreanus and Rheum palmatum on hepatitis B virus replication in HepG2 2.2.15 cells", Yakhak Hoeji, vol. 43, No. 4, Aug. 1999, pp. 458-463.
Lee H-B et al.: "Immunomodulator effects of herbal Scutellaria baicalnesis extract on cytokine production by Der p I-specific CD4+ cells in atopic individuals", Journal of Allergy and Clinical Immunology, vol. 105, No. 1, Part 2, Jan. 1, 2000, p. S151.
Pijush Kundu et al.: "A brief resume on the genus Ailanthus: chemical and pharmacological aspects", Phytochemistry Reviews, vol. 9, No. 3, Nov. 12, 2009, pp. 379-412, Kluwer Academic Publishers.
Okunade A L et al.: "Antiplasmodial activity of extracts and quassinoids isolated from seedlings of Ailanthus altissima (Simaroubaceae)", Phytotherapy Research, vol. 17, No. 6, Jun. 2003, pp. 675-677.
Chinese Office Action for Chinese Application No. 201180068626.0 dated Sep. 9, 2014.
"The Pharmacological Action and the Clinical Application of Sanguisorba", Jin Meihua, Modern Medicine and Hygiene,vol. 25, No. 16, p. 2479 [abstract translation enclosed].
Chinese Ancient Medical Prescription,Zhang Fangsheng, Scientific and Technical Documentation Press, pp. 461-462 [abstract translation enclosed].
Chinese Office Action for application No. 201180068626.0 dated Apr. 19, 2016.
Jin Meihua "The Pharmacological Action and the Clinical Application of Sangiusorba" Modern Medicine and Hygiene, vol. 25, No. 16 p. 2479, Dec. 31, 2009.
Zhang Fangsheng "Chinese Ancient Medical Prescription" Scientific and Technical Documentation Press, pp. 461-462, May 31, 1999.
Chinese Office Action for App. No. 201180068626.0 dated Oct. 10, 2016.
Shin, Tae-Yong, Kyeong-Bo Lee, and Sang-Hyun Kim. "Antiallergic effects of Sanguisorba officinalis on animal models of allergic reactions." Immunopharmacology and immunotoxicology 24.3 (2002): pp. 455-468.
Canadian Office Action for CA Application No. 2,823,086 dated Jun. 6, 2017.
Shan, B., Cai, Y. Z., Brooks, J. O., & Corke, H. (2007). The in vitro antibacterial activity of dietary spice and medicinal herb extracts. *International Journal of food microbiology*, 117(1), pp. 112-119.
Rahman, Atiqur, Eun Lyang Kim, and Sun Chu: Kang. "Antibacterial and antioxidant properties of Ailanthus altissima Swingle leave extract to reduce foodborne pathogens and spoiling bacteria." *Journal of food safety* 29.4 (2009): 499-510.
Manish, S. L., and S. H. Mishra. "Nutritional and therapeutic potentialof Ailanthus excelsa-A Review." *Pharmacognosy reviews* 1.1 (2007): 105.-113.
KR Office Action for KR Application No. 10-2013-7020011 dated Nov. 15, 2017.

* cited by examiner

Concentration 1- 1% ( Fisetin-100 µM); Concentration 2-0.1% (Fisetin- 10 µM); Concentration 3- 0.01% (Fisetin- 1 µM)

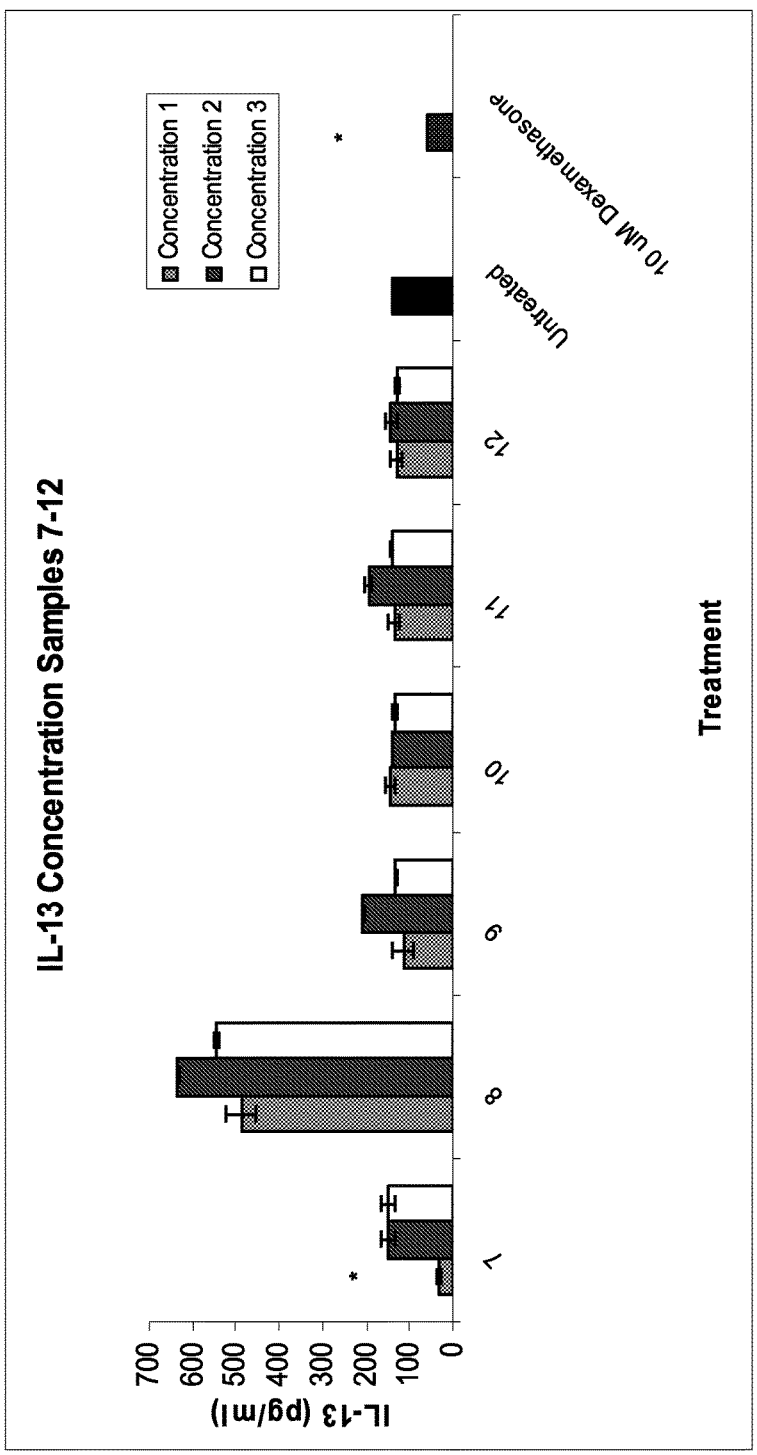

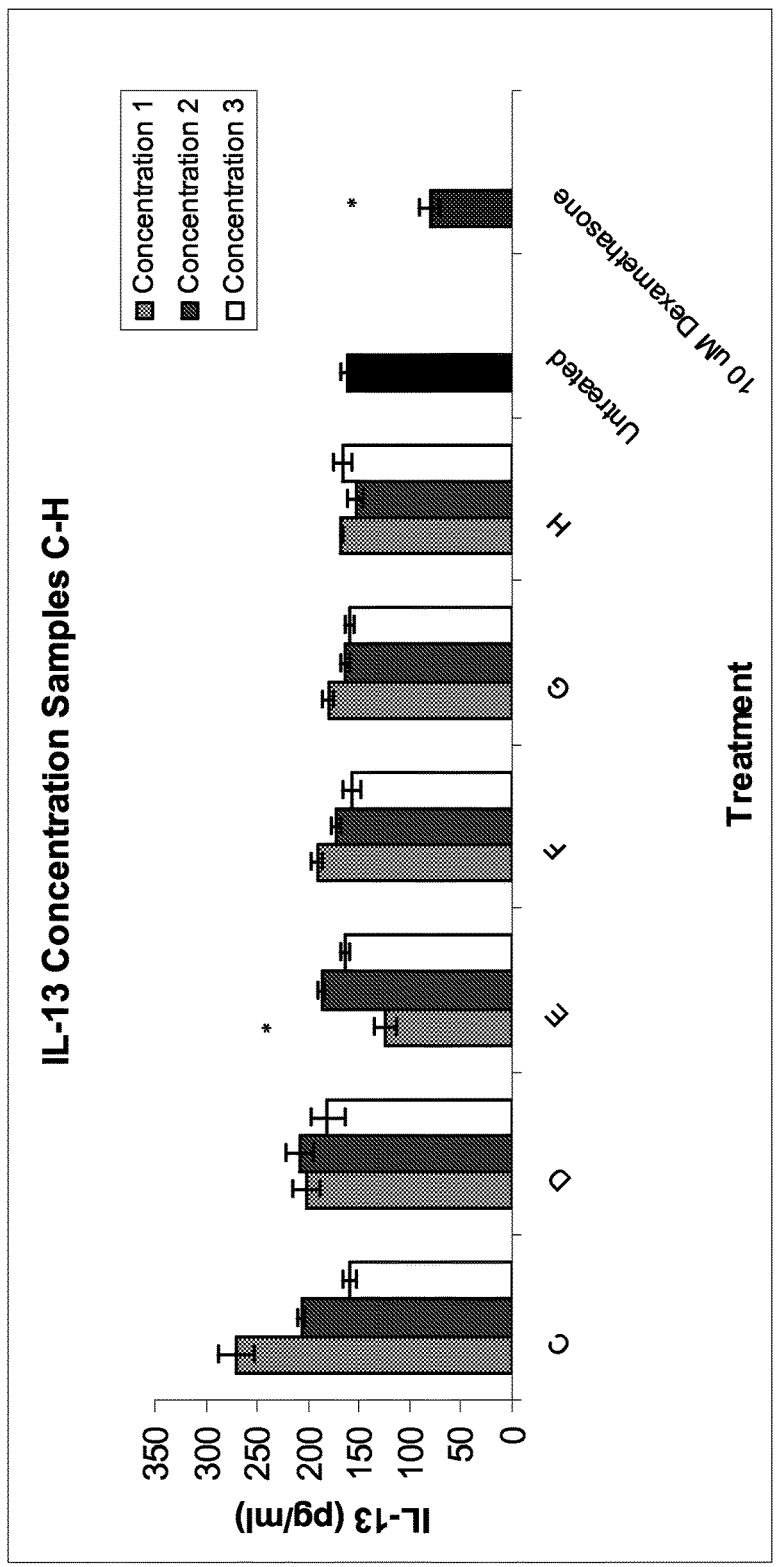

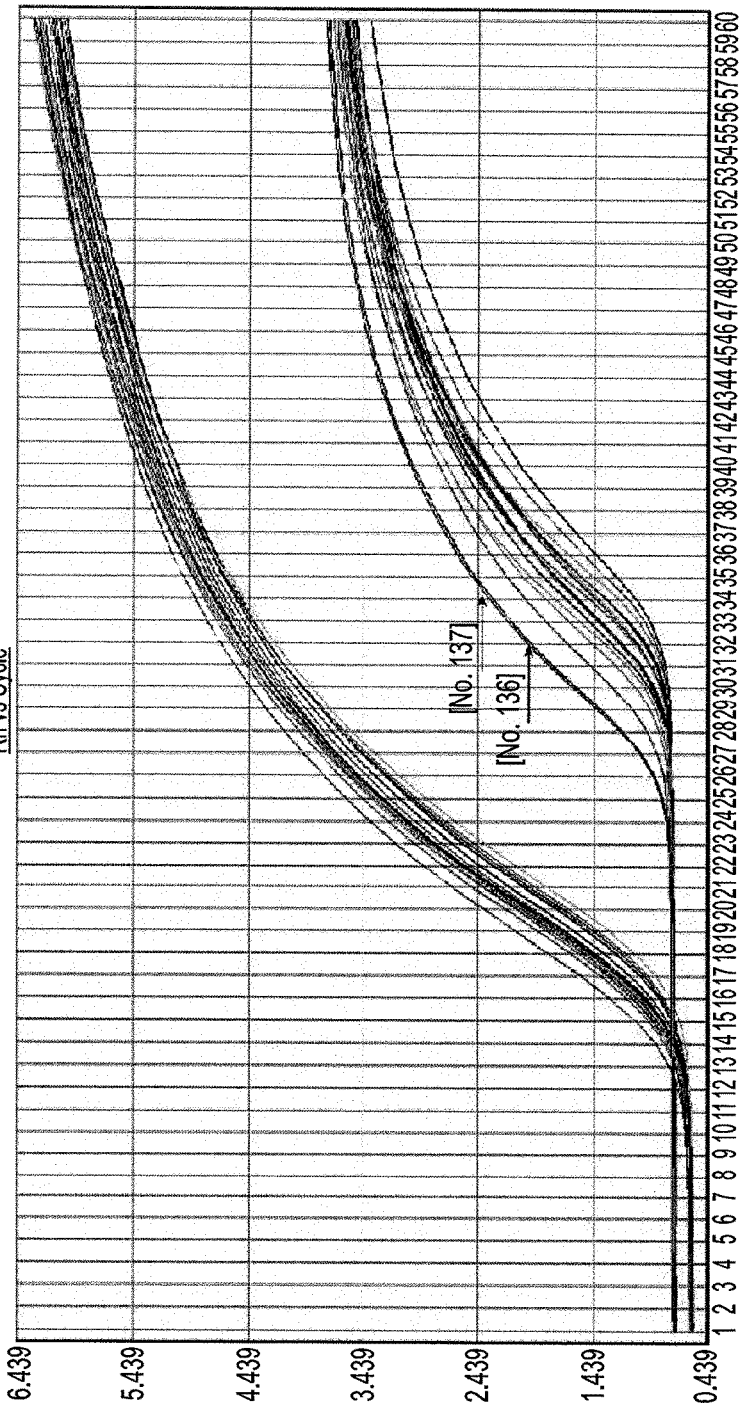

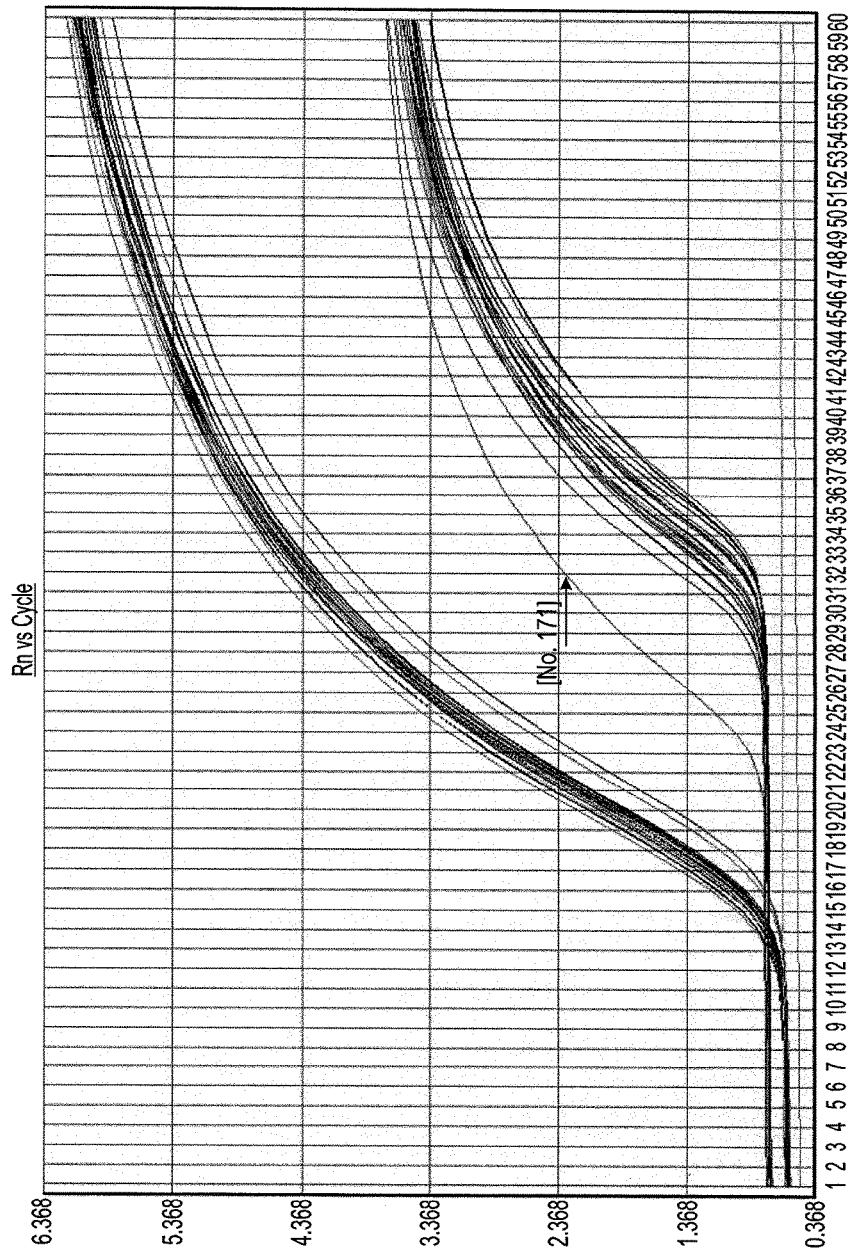

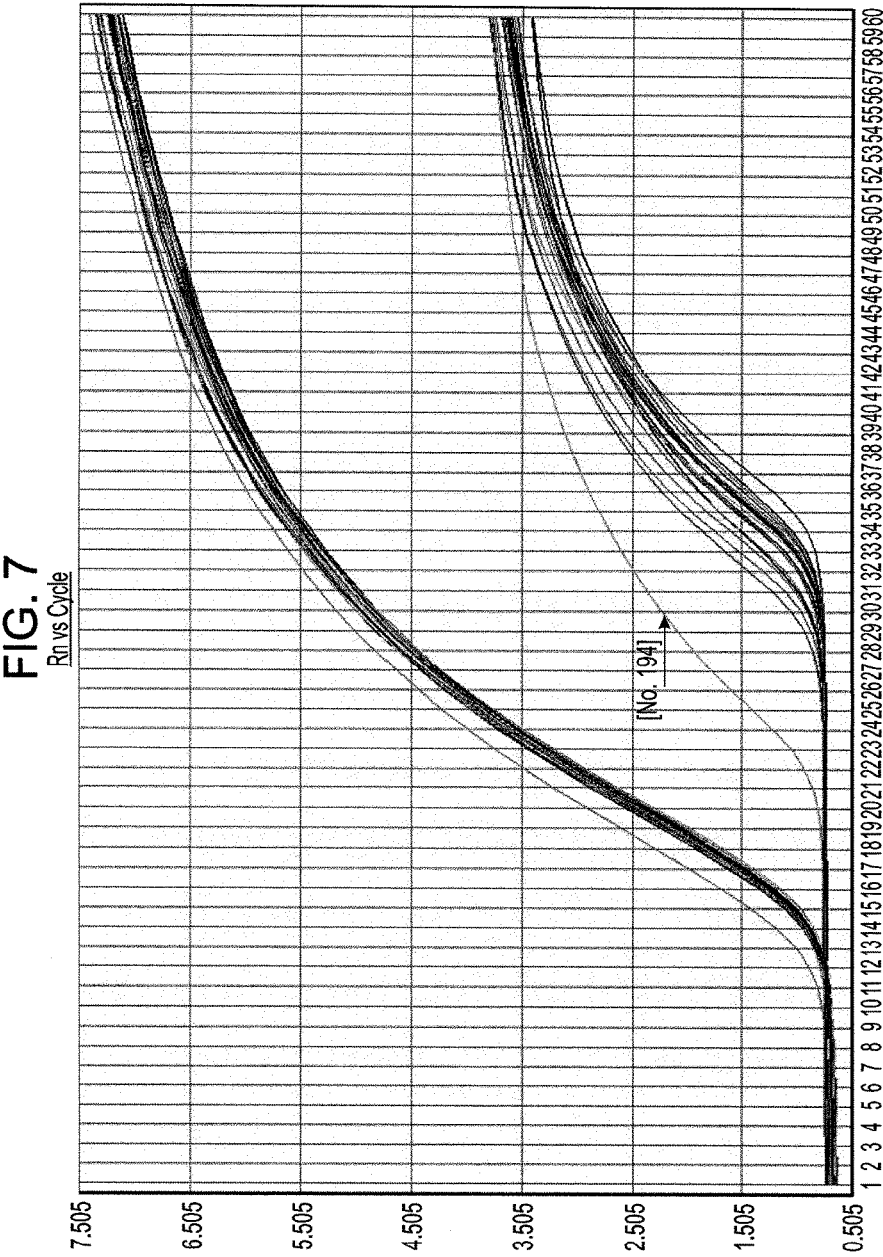

Rn vs Cycle

Rn vs Cycle

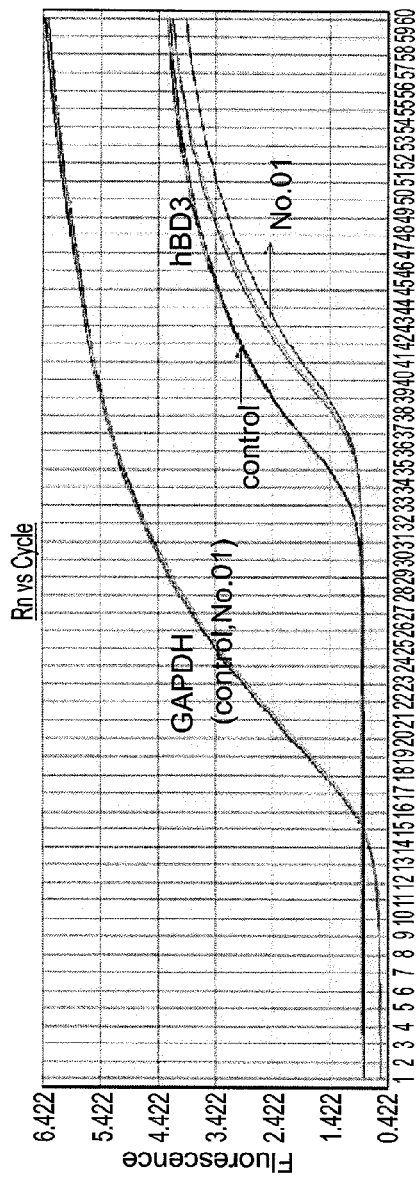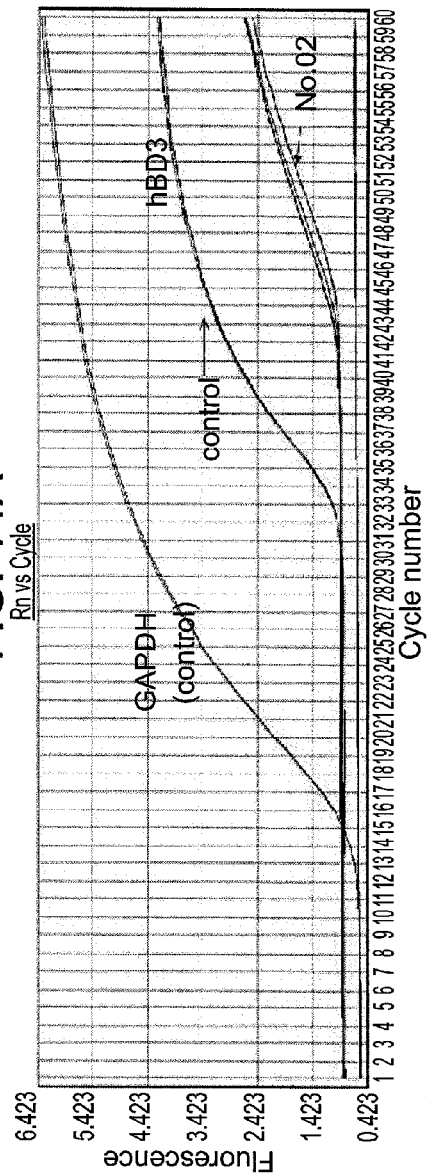
FIG. 14A
FIG. 14B

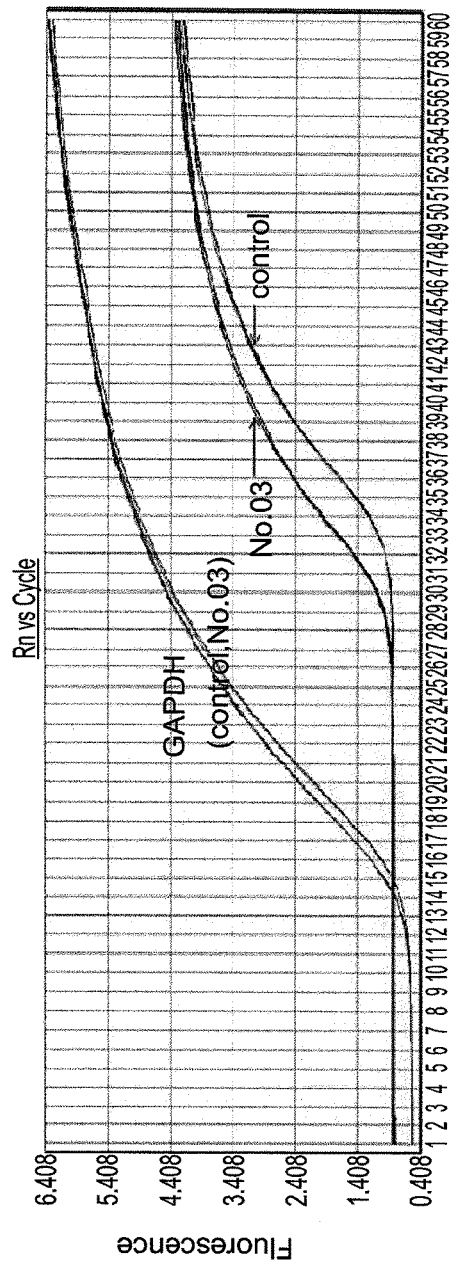
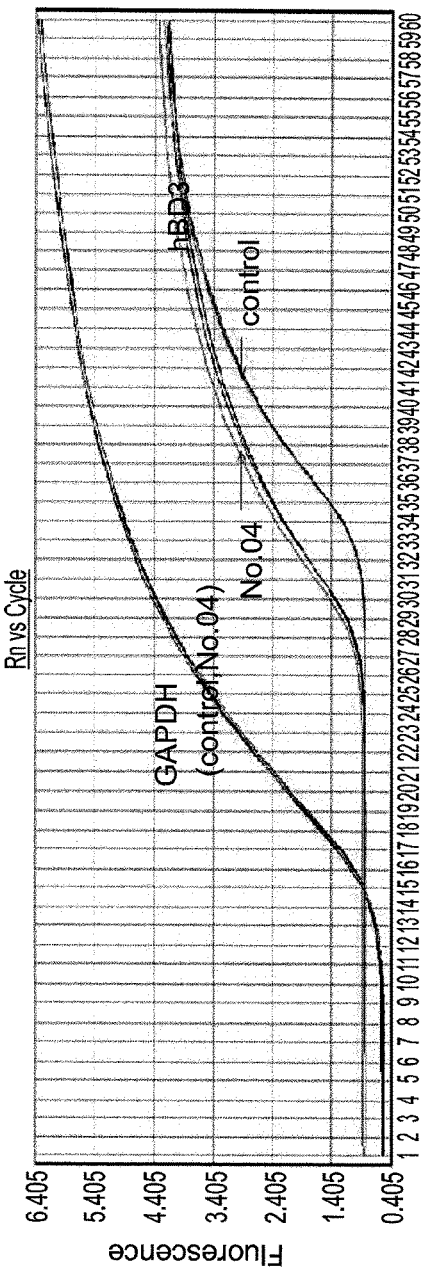
FIG. 14C
FIG. 14D

*Stap. aureus subsp aureus*

Amp resistant *E. coli*

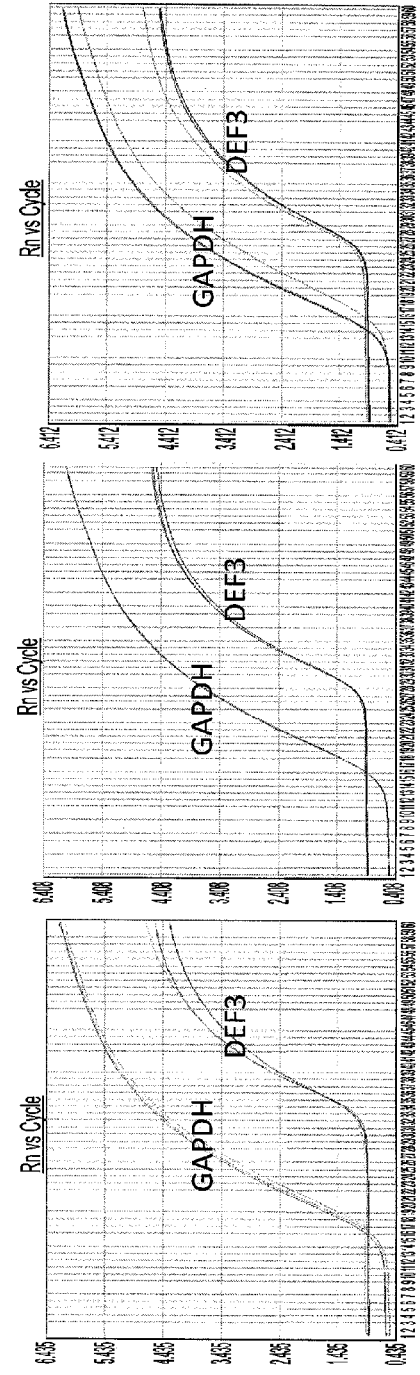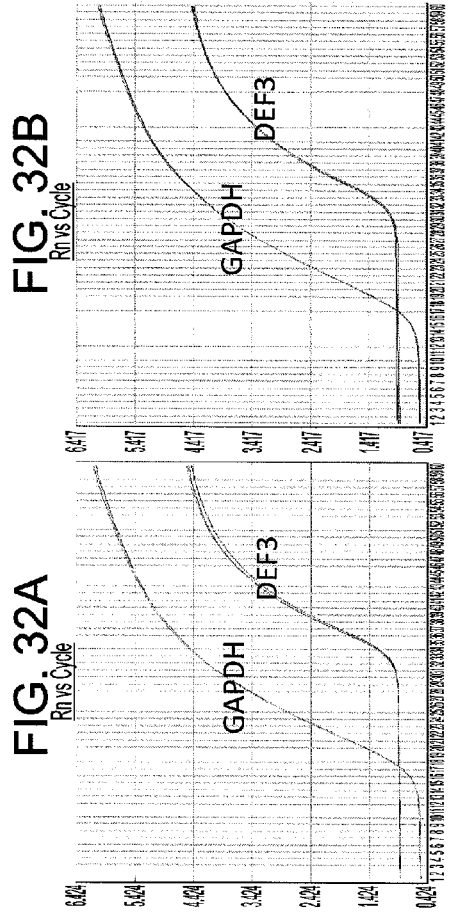

PLANT EXTRACTS FOR THE TREATMENT AND PREVENTION OF INFECTIONS

CROSS-REFERENCE TO RELATED APPLICATIONS

This application is a National Phase Application of PCT International Application No. PCT/IL2011/050081, filed Dec. 28, 2011, claiming the benefit of US Provisional Application No. 61/427,495, filed on Dec. 28, 2010, hereby incorporated by reference.

FIELD AND BACKGROUND OF THE INVENTION

The present invention, in some embodiments thereof, relates to plant extracts and, more particularly, but not exclusively, to the use of same for the treatment or prevention of infections including secondary infections of chronic inflammatory diseases.

Atopic dermatitis (AD) is a common chronic inflammatory skin disease, with lifetime prevalence of 10-20% in children, and 1-3% in adults. The incidence of the disease appears to be increasing especially in the developed countries. AD is associated with cutaneous hyper-reactivity to environmental triggers that are innocuous to normal non-atopic individuals and is typified by pruritus, eczematous lesions, xerosis (dry skin), and lichenification of the skin (thickening of the skin and skin marks). AD is often complicated by recurrent infections of skin lesions by bacterial, viral and fungal pathogens (e.g. *Staphylococcus aureus* colonization takes place in 85-90% of patients with AD). The secondary infection treatments available to date for AD patients do not cure the skin disorder but do control the severity and duration of its symptoms. These treatments include mainly antibiotics to treat secondary infections, topical corticosteroids, and topical calcineurin inhibitors (immuno-suppressant agents). These treatments are not recommended for long-term use, especially for young children, due to their potential side effects.

The underlying biological mechanisms of AD are poorly understood. Several cell types including immune and epidermal cells seem to be involved, including T lymphocytes, mast cells, eosinophils, Langerhans cells and keratinocytes. Other factors, including cytokines and IgE, are also implicated. Many early academic and clinical reports suggest a number of different pathogenic mechanisms. One possible mechanism is an immune defect involving elevation of $T_H2$ cells that interact with Langerhans cells and results in increased production of interleukins IL-4, IL-5, IL-6, IL-10 and IL-13. This leads to increased IgE and decreased gamma interferon levels. Another theory involves the defective barrier function in the stratum corneum leading to the entry of antigens, which results in the production of various inflammatory cytokines.

Recently it was suggested that the high susceptibility for bacterial infection in AD patients is associated with the defective innate defense mechanism, specifically, the low expression of antimicrobial peptides, known as β-defensins Skin biopsies from AD lesions demonstrated deficiently low expression of inflammation induced antimicrobial peptides, thus providing a possible explanation for the susceptibility of patients with AD to skin infections.

β-defensins, including the human β-defensins (hBDs), are natural, small, cationic, amphipathic molecules which are involved in the innate defense mechanism. In the skin, these peptides are secreted by keratinocytes, and have a major role in directly killing the invading microorganisms and modifying inflammatory events. These peptides disrupt the membrane of the target microbe or penetrate the microbial membrane, interfering with intracellular functions. They also display additional roles, such as regulation of inflammatory and immune responses, chemoattracting immune or inflammatory cells to wound or infection/inflammation sites, acceleration of angiogenesis and promotion of wound healing.

Human β-defensin-3 (hBD-3) exhibits potent killing activity against *S. aureus* and other gram-positive bacteria in addition to activity against gram-negative organisms. Moreover, the antimicrobial activity of hBD-3 is retained at physiologic salt concentrations. Thus, endogenous production of hBD-3 in the epidermis may provide an antimicrobial shield to protect cutaneous tissues from bacterial invasion against pathogens such as *S. aureus*.

Regulation of β-defensins expression including, human β-defensin-2 (hBD-2) and human β-defensin-3 (hBD-3) expression, is a complicated mechanism; their expression is elevated by microorganisms, TNF-alpha or IFN-gamma, and is down-regulated by cytokines produced by mast cells and type 2 helper T cells (specifically IL-4 and IL-13).

In vitro studies using primary keratinocytes demonstrated that IL-4 and IL-13 cytokine expression inhibits the expression of β-defensins [Albanesi C. et al., J. Immunol. (2007) 179(2): 984-992]. This inverse correlation was also demonstrated in human skin biopsies [Nomura I. et al., J. Immunol. (2003) 171(6), 3262-3269].

Several herbal extracts that inhibit IL-4 and/or IL-13 expression induced by mast cells and type 2 helper cells have been previously described. These include Gammi-Danguieumja prescription (*Rehmannia glutinosa*, *Angelica gigas*, etc.) [Na H J. et al., Inflammation (2004) 28, 291-297], flavonoids (Avanin, Luteolin, Apigenin, Fisetin, etc.) [Kawai, M. et al., Allergology International (2007) 56:113-123], *Ailanthus altissima* (EAa) [Hua Jin, M. et al., Biol Pham Bult (2006) 29: 884-888], *Glycyrrhiza glabra* L. (Licorice root) [Ram A et al., Int Immunopharacol. (2006) 6(9):1468-77], *Cimicifuga raceomosa* [Kim C D et al., Immunopharmacol Immunotoxicol (2004) 26: 299-308] and *Cimicifuga racemosa* [Kim C D et al., supra].

Herbs that comprise anti-inflammatory and anti-allergic properties have been previously described in the art. These include *Sanguisorba officinalis* known in Traditional Chinese Medicine to treat eczema and pain in the skin and *Silybum marianum* previously described to comprise anti-inflammatory properties.

U.S. Pat. No. 6,235,287 discloses diterpenes as well as extracts or concentrates of the plant *Curcuma amada* containing at least one such diterpene for use as medicaments for immuno-modulation and for the alleviation of pain, and for the treatment or prevention of hypersensitivity diseases and autoimmune disorders.

U.S. Pat. Nos. 6,566,405 and 7,252,845 disclose compositions containing aromatic compounds and terpenoids which are present in and may preferably be derived from the plant *Alpinia galanga* (Zingiberaceae). These show synergistic effects with respect to immuno-modulation and significantly suppress hypersensitivity reactions. Thus, 6566405 contemplates the use of same for the treatment or prevention of IgE mediated allergic reactions and conditions, such as asthma, allergic rhinitis, a topic eczema or anaphylaxis, and autoimmune disorders, such as Crohn's disease, ulcerative colitis, rheumatoid arthritis or psoriasis, as well as for the alleviation of pain.

U.S. Pat. No. 5,466,452 discloses pharmaceutical herbal compositions for the treatment of skin disorders such as eczema and psoriasis. Specifically U.S. Pat. No. 5,466,452 teaches preparation of an extract or extracts of herbs (e.g. of *Potentilla chinensis, Rehmannia glutinosa, Radix paeoniae lactiflorae/veitchii, Dictamnus augustifolia, Glycyrrhiza uralensis, Ledebouriella sesloides, Tribulus terrestris, Lopatheri gracile, Schizonepeta tenuifolia, Akebia trifoliata*) which provide an anti-inflammatory agent, an adrenocortical stimulant and a cortisol protecting agent by steam distillation and decoction and then treating the extracts to reduce the polysaccharide and/or sugar content.

U.S. Pat. No. 6,676,975 discloses Chinese herbal compositions for treating eczema and psoriasis. Specifically, U.S. Pat. No. 6,676,975 relates to a material which is suitable for the treatment of atopic disease, non-atopic eczema or psoriasis. The material can be extracted from a freeze-dried decoction of a mixture comprising the following Chinese herbs: *Radix Ledebouriella, Fructus Tribuli, Herba Potentilla chinensis, Caulis Clematis armandii, Radix Rehmannia, Radix Glycyrrhiza, Radix Paeonia rubra, Cortex Dictamni radicis, Herba Lopatheri, Spica Schizonepetae*.

U.S. Pat. No. 7,211,567 discloses composition for preventing and treating type I allergy (including atopic dermatitis). The astragalin needed for preparing the compositions taught in U.S. Pat. No. 7,211,567 may be obtained from any astragalin-containing plant e.g. *Ailanthus altissima*.

Additional background art includes U.S. Pat. Nos. 6,143,498, 6,329,340, 6,335,318, 6,420,116, 6,911,577 and 7,223,840 and U.S. Patent Application Nos. 20060147442, 20070104722 and 20060036083.

SUMMARY OF THE INVENTION

According to an aspect of some embodiments of the present invention there is provided a composition comprising a *Sanguisorbae officinalis* plant extract and at least one additional plant extract selected from the group consisting of an *Ailanthus altissima* plant extract, a *Galla rhois gallnut* plant extract, a *Glycyrrhiza Glabra* plant extract, a *Rheum palmatum* plant extract and a *Scutellaria baicalensis* plant extract.

According to an aspect of some embodiments of the present invention there is provided a method of treating and/or preventing atopic dermatitis (AD) in a subject in need thereof, the method comprising administering to the subject a therapeutically effective amount of a composition comprising a *Sanguisorbae officinalis* plant extract and an *Ailanthus altissima* plant extract, thereby treating and/or preventing the infection in the subject.

According to an aspect of some embodiments of the present invention there is provided a use of a composition comprising a *Sanguisorbae officinalis* plant extract and an *Ailanthus altissima* plant extract for the treatment and/or prevention of atopic dermatitis (AD) in a subject in need thereof.

According to an aspect of some embodiments of the present invention there is provided a composition comprising a plant extract, wherein the plant is selected from the group consisting of *Galla rhois gallnut, Peucedanum praeruptorum* and *Cimicifuga raceomosa*.

According to an aspect of some embodiments of the present invention there is provided a composition comprising an *Ailanthus altissima* plant extract and at least one additional plant extract selected from the group consisting of a *Galla rhois gallnut* plant extract, a *Glycyrrhiza Glabra* plant extract, a *Rheum palmatum* plant extract and a *Scutellaria baicalensis* plant extract.

According to an aspect of some embodiments of the present invention there is provided a composition comprising Ailanthone at a concentration of at least about 0.01% and a cosmetically or a pharmaceutically acceptable carrier.

According to an aspect of some embodiments of the present invention there is provided a method of treating and/or preventing an infection in a subject in need thereof, the method comprising administering to the subject a therapeutically effective amount of the composition of the present invention, thereby treating and/or preventing the infection in the subject.

According to an aspect of some embodiments of the present invention there is provided a use of the composition of the present invention for the treatment and/or prevention of an infection in a subject in need thereof.

According to an aspect of some embodiments of the present invention there is provided a delivery system comprising an applicator and the composition of the present invention contained within.

According to an aspect of some embodiments of the present invention there is provided a unit dosage form comprising *Sanguisorbae officinalis* plant extract at a concentration of about 0.5-2% weight/weight.

According to an aspect of some embodiments of the present invention there is provided a unit dosage form comprising *Ailanthus altissima* plant extract at a concentration of about 0.5-2% weight/weight.

According to an aspect of some embodiments of the present invention there is provided a unit dosage form comprising *Glycyrrhiza Glabra* plant extract at a concentration of about 0.5-2% weight/weight.

According to an aspect of some embodiments of the present invention there is provided a unit dosage form comprising *Galla rhois gallnut* plant extract at a concentration of about 0.5-2% weight/weight.

According to an aspect of some embodiments of the present invention there is provided a unit dosage form comprising *Sanguisorbae officinalis* plant extract at a concentration of about 0.5-2% weight/weight, *Ailanthus altissima* plant extract at a concentration of about 0.5-2% weight/weight and *Glycyrrhiza Glabra* plant extract at a concentration of about 0.5-2% weight/weight.

According to an aspect of some embodiments of the present invention there is provided a unit dosage form comprising *Sanguisorbae officinalis* plant extract at a concentration of about 0.5-2% weight/weight, *Ailanthus altissima* plant extract at a concentration of about 0.5-2% weight/weight and *Galla rhois gallnut* plant extract at a concentration of about 0.5-2% weight/weight.

According to an aspect of some embodiments of the present invention there is provided a unit dosage form selected from the group consisting of a topical, an oral, a pulmonary or an ocular unit dosage form comprising Ailanthone at a concentration of at least about 0.01% weight/weight.

According to an aspect of some embodiments of the present invention there is provided a method of preparing a composition for treating and/or preventing an infection, the method comprising: (a) subjecting a plant to ×1-10 volumes of water to produce an extract of the plant; and (b) reducing the amount of organic salts and/or heavy metals and/or starch in the plant extract using a macroporous resin which results in an elevated content of an active ingredient which is present in the plant extract.

According to an aspect of some embodiments of the present invention there is provided a method of identifying an agent having inflammatory modulator properties, the method comprising: (a) contacting the agent with a cell; and (b) assaying secretion of a human beta-defensin from the cell, wherein an upregulation in the beta-defensin secretion following the contacting is indicative that the agent has an inflammatory modulator properties.

According to an aspect of some embodiments of the present invention there is provided a cosmetic carrier comprising a *Rheum Palmatum* Root Extract, a *Cnidium Monnieri* Fruit Extract, a *Scutellaria Baicalensis* Root Extract and Dipotassium Glycyrrhizate.

According to an aspect of some embodiments of the present invention there is provided a cosmetic composition comprising a *Sanguisorbae officinalis* plant extract, an *Ailanthus altissima* plant extract, a *Rheum Palmatum* Root Extract, a *Cnidium Monnieri* Fruit Extract, a *Scutellaria Baicalensis* Root Extract and Dipotassium Glycyrrhizate.

According to some embodiments of the invention, the composition comprises the *Sanguisorbae officinalis* plant extract, the *Ailanthus altissima* plant extract and the *Glycyrrhiza Glabra* plant extract.

According to some embodiments of the invention, the composition comprises the *Sanguisorbae officinalis* plant extract, the *Ailanthus altissima* plant extract and the *Galla rhois gallnut* plant extract.

According to some embodiments of the invention, the composition comprises the *Sanguisorbae officinalis* plant extract and the *Ailanthus altissima* plant extract.

According to some embodiments of the invention, the composition comprises the *Sanguisorbae officinalis* plant extract and the *Galla rhois gallnut* plant extract.

According to some embodiments of the invention, the composition comprises the *Sanguisorbae officinalis* plant extract and the *Glycyrrhiza Glabra* plant extract.

According to some embodiments of the invention, the composition comprises the *Sanguisorbae officinalis* plant extract and the *Rheum palmatum* plant extract.

According to some embodiments of the invention, the composition comprises the *Sanguisorbae officinalis* plant extract and the *Scutellaria baicalensis* plant extract.

According to some embodiments of the invention, the composition further comprises *Sanguisorbae officinalis* plant extract.

According to some embodiments of the invention, the composition further comprises a plant extract selected from the group consisting of a *Galla rhois gallnut* plant extract, a *Glycyrrhiza Glabra* plant extract a *Rheum Palmatum* Root Extract, a *Cnidium Monnieri* Fruit Extract and a *Scutellaria Baicalensis* Root Extract.

According to some embodiments of the invention, the composition further comprises Dipotassium Glycyrrhizate.

According to some embodiments of the invention, the composition is formulated for topical, ocular, oral or pulmonary administration.

According to some embodiments of the invention, the concentration of the Ailanthone is about 0.01-1%.

According to some embodiments of the invention, the concentration of the Ailanthone is about 0.01-5%.

According to some embodiments of the invention, the *Sanguisorbae officinalis* plant extract and the at least one additional plant extract are formulated in a co-formulation.

According to some embodiments of the invention, the *Sanguisorbae officinalis* plant extract and the at least one additional plant extract are formulated in separate formulations.

According to some embodiments of the invention, the concentration of each of the plant extracts in the composition is in the range of 0.01-10%.

According to some embodiments of the invention, the concentration of each of the plant extracts in the composition is in the range of 0.5-2%.

According to some embodiments of the invention, the concentration of each of the plant extracts in the composition is 1%.

According to some embodiments of the invention, the concentration of the plant extract in the composition is in the range of 0.01-10%.

According to some embodiments of the invention, the concentration of the plant extract in the composition is in the range of 0.5-2%.

According to some embodiments of the invention, the concentration of the plant extract in the composition is 1%.

According to some embodiments of the invention, the *Ailanthus altissima* plant extract comprises at least about 0.01% Ailanthone.

According to some embodiments of the invention, the *Ailanthus altissima* plant extract consists of *Ailanthi radicis* plant extract.

According to some embodiments of the invention, the *Ailanthi radicis* plant extract is a polar extract.

According to some embodiments of the invention, the polar extract is extracted using a polar solvent selected from the group consisting of a butyl alcohol and an ethyl alcohol.

According to some embodiments of the invention, the *Ailanthi radicis* plant extract is further purified using a high-performance liquid chromatography (HPLC).

According to some embodiments of the invention, the plant extract comprises an aqueous plant extract.

According to some embodiments of the invention, the aqueous plant extract is further purified using a resin chromatography.

According to some embodiments of the invention, the resin chromatography comprises a macroporous resin.

According to some embodiments of the invention, the composition does not comprise a beta-defensin.

According to some embodiments of the invention, the composition is a pharmaceutical composition and comprises a pharmaceutically acceptable carrier or diluent.

According to some embodiments of the invention, the composition is a cosmetic composition and comprises a cosmetically acceptable carrier or diluent.

According to some embodiments of the invention, the cosmetically acceptable carrier or diluent is formulated in a form selected from the group consisting of a cream, a gel, a spray, a lotion, an ointment, an oil, a wash, a shampoo, a soap and a spray.

According to some embodiments of the invention, the infection is secondary to chronic inflammation.

According to some embodiments of the invention, the infection is associated with a disease selected from the group consisting of an atopic disease, a contact dermatitis, a nummular dermatitis, a radiation dermatitis, a burn, a non-atopic eczema, a pressure sore, an eye inflammatory disease, a respiratory inflammatory diseases, an asthma, a gastrointestinal disease and an oral infectious disease.

According to some embodiments of the invention, the subject is a human being.

According to some embodiments of the invention, the therapeutically effective amount is for downregulating secretion of a Th2 type cytokine in a cell of the subject.

According to some embodiments of the invention, the Th2 type cytokine is selected from the group consisting of IL-4, IL-5, IL-6, IL-10 and IL-13.

According to some embodiments of the invention, the therapeutically effective amount is for upregulating expression of a human beta-defensin in a cell of the subject.

According to some embodiments of the invention, the therapeutically effective amount comprises an anti-microbial activity.

According to some embodiments of the invention, the applicator is in a form selected from the group consisting of an adhesive bandage, a non-adhesive bandage, a wipe, a gauze and a pad.

According to some embodiments of the invention, the unit dosage form further comprises *Ailanthus altissima* plant extract at a concentration of about 0.5-2% weight/weight.

According to some embodiments of the invention, the unit dosage form further comprises *Glycyrrhiza Glabra* plant extract at a concentration of about 0.5-2% weight/weight.

According to some embodiments of the invention, the unit dosage form further comprises *Galla rhois gallnut* plant extract at a concentration of about 0.5-2% weight/weight.

According to some embodiments of the invention, the unit dosage form further comprises *Rheum palmatum* plant extract at a concentration of about 0.5-2% weight/weight.

According to some embodiments of the invention, the unit dosage form further comprises *Scutellaria baicalensis* plant extract at a concentration of about 0.5-2% weight/weight.

According to some embodiments of the invention, the concentration of the plant extract is 1% weight/weight.

According to some embodiments of the invention, the concentration of the Ailanthone is about 0.01-1% weight/weight.

According to some embodiments of the invention, the unit dosage form is in a form selected from the group consisting of an adhesive bandage, a non-adhesive bandage, a wipe, a gauze and a pad.

According to some embodiments of the invention, the composition, delivery system or unit dosage form further comprises a factor selected from the group consisting of an extracellular matrix component, a growth factor, a hormone, an angiogenic factor, a coagulation factor, a cytokine inhibitor, a chemokine inhibitor, an enzyme, a neurotransmitter, a vitamin, a carbohydrate, an ion, an iron chelator, a fatty acid, an anti-microbial agent, an antibiotic, a steroid and an amino acid.

According to some embodiments of the invention, the administering is effected chronically.

According to some embodiments of the invention, the administering is effected at least once a day.

According to some embodiments of the invention, the administering is effected for at least 21 days.

According to some embodiments of the invention, the plant is selected from the group consisting of *Ailanthus altissima, Galla rhois gallnut, Peucedanum praeruptorum, Glycyrrhiza glabra, Cimicifuga raceomosa, Silybum marianum, Sanguisorbae officinalis, Rheum palmatum* and *Scutellaria baicalensis*

According to some embodiments of the invention, the *Ailanthus altissima* consists of *Ailanthi radicis*.

According to some embodiments of the invention, the active ingredient is selected from the group consisting of Ailanthone, Mersosin, Toosendanin, General Ginsenoide, Galic acid, Liquiritin, Praeruptorin A, Tannic acid and Silybin.

According to some embodiments of the invention, the plant comprises *Ailanthi altissima*, the active ingredient comprises Ailanthone.

According to some embodiments of the invention, the agent comprises a plant extract or active ingredient thereof.

According to some embodiments of the invention, the cell comprises a keratinocyte cell.

According to some embodiments of the invention, the cosmetic composition further comprises a moisturizer and an emollient.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-G are graphs depicting inhibition of IL-13 expression by herbal extracts in KU812 cells. KU812 cells were treated with the herbal extracts as described in Example 1, herein below, and the cell culture supernatants were then assayed for IL-13 expression. Values are presented as mean IL-13 concentration (pg/ml)±SD. FIG. 4A test materials: 1—*Glycyrrhiza glabra;* 2—*Saposhnikovia divaricata;* 3—Radix *Tripterygii wilfordii;* 4—*Cimicifuga racemosa;* 5—*Celosia argentea;* 6—Coptis Root. Measured concentrations: Concentration 1—1% (for sample 6—0.05%), Concentration 2—0.1% (for sample 6—0.01%), Concentration 3—0.01% (for sample 6—0.001%); FIG. 4B test materials: 7—*Salviae miltiorrhizae;* 8—*Saururus Chinensis leaves;* 9—*Calendula officinalis;* 10—Gentiana; 11—*Mentha aquatica* L; 12—*Taraxacum officinale*. Measured concentrations: Concentration 1—1% (for sample 10—0.1%), Concentration 2—0.1% (for sample 10—0.01%), Concentration 3—0.01% (for sample 10—0.001%); FIG. 4C test materials: 13—Broom Cypress Fruit; 14—*Anemarrhena asphodeloides;* 15—*Stellaria* dichotoma L. var. *Lanceolata* Root; 16—*Fritillaria verticillate*; 17—*Silybum marianum*; 18—*Actinidia polygama*. Measured concentrations: Concentration 1—1% (for sample 15—0.1%), Concentration 2—0.1% (for sample 15—0.01%), Concentration 3—0.01% (for sample 15—0.001%); FIG. 4D test materials: 19—Phellodendron; 20—*Sapindus mukurossi;* 21—*Radix Sophora flavescents;* 22—*Sanguisorba officinalis;* 23—*Fructus Cnidii;* 24—*Camelia japonica*. Measured concentrations: Concentration 1—1% (for sample 19—0.05%, sample 20—0.01%, sample 21—0.5%), Concentration 2—0.1% (for sample 19—0.01%, sample 20—0.005%), Concentration 3—0.01% (for sample 19, 20—0.001%). FIG. 4E test materials: 25—*Scutellaria baicalensis;* 26—*Rheum palmatum;* 27—Chrysanthemum; 28—Portulaca; A—Peony Bark; B—*Angelica sinensis*. Measured concentrations: Concentration 1—1% (for sample 27 and 28—0.1%), Concentration 2—0.1% (for sample 27 and 28—0.05%), Concentration 3—0.01%. FIG. 4F test materials: C—*Astragalus membranaceus;* D—*Evodia rutaecarpa;* E—*Polygonum cuspidatum;* F—*Liriope platyphylla;* G—*Smilacis glabrae;* H—*Curcuma longa*. Measured concentrations: Concentration 1—1% (for sample D and H—0.1%, samples E and F—0.5%), Concentration 2—0.1% (for sample D—0.05%, sample H—0.01%), Concentration 3—0.01% (sample H—0.001%). FIG. 4G test materials: I—Indigo; J—*Semen Hydnocarpi hainanensi*. Measured concentrations: I and J—1%, 0.1% and 0.01%. Fisetin: 100 µM, 10 µM and 1 µM.

FIG. 5 is a line graph depicting herbal extracts Nos. 136 and 137 which led to in a significant increase in the expression of hBD-3 (see arrows).

FIG. 6 is a line graph depicting herbal extract No. 171 which led to a significant increase in the expression of hBD-3.

FIG. 7 is a line graph depicting herbal extract No. 194 which led to a significant increase in the expression of hBD-3.

FIGS. 14A-E are graphs depicting the stimulation effect of herbal extracts on human beta-defensin 3 (hBD-3) as measured by RT-PCR. Each herbal extract was measured for beta-defensin stimulatory effect [FIGS. 14A-D: FIG. 14A shows the direct effect of *Glycyrrhiza glabra* (No. 1) on the expression of hBD3. FIG. 14B shows the direct effect of *Cimicifuga raceomosa* (No. 2) on the expression of hBD3. FIG. 14C shows the direct effect of *Silybum marianum* (No. 3) on the expression of hBD3 and FIG. 14D shows the direct effect of *Sanguisorbae officinalis* (No. 4) on the expression of hBD3]; FIG. 14E summarizes the results of the stimulation activity of herbal extracts on hBD-3 expression. The test material identification is as follows: 1. *Glycyrrhiza glabra;* 2. *Cimicifuga raceomosa;* 3. *Silybum marianum;* 4. *Sanguisorbae officinalis*.

FIG. 15A the test material identification is as follows: 1. *Glycyrrhiza glabra;* 2. *Cimicifuga raceomosa;* 3. *Silybum marianum;* 4. *Sanguisorbae officinalis*. FIG. 15B the Test material identification: 1% *Ailanthus altissima* with 0.3%: 1. *Glycyrrhiza glabra;* 2. *Cimicifuga raceomosa;* 3. *Silybum marianum;* 4. *Sanguisorbae officinalis*. FIG. 15C the test material identification is as follows: 1% *Galla rhois gallnut* with 0.3% of: 1. *Glycyrrhiza glabra;* 2. *Cimicifuga raceomosa;* 3. *Silybum marianum;* 4. *Sanguisorbae officinalis*.

FIG. 17A depicts anti-microbial activity against ampicillin-resistant *E. coli; * and FIG. 17B depicts anti-microbial activity against *S. aureus*.

FIGS. 32A-E are line grafts depicting the effect of water extract, butyl alcohol extract and ethyl acetate extract of *Ailanthi radicis* on human beta-defensin3 and GAPDH (internal expression control gene) from HaCaT cells. FIG. 32A depict the effect of 10 µl of water (control) on the expression of DEF3 and GAPDH; FIG. 32B depict the effect of 10 µl of *Ailanthi radicis* water extract on the expression of DEF3 and GAPDH; FIG. 32C depict the effect of 10 µl of DMSO (control) on the expression of DEF3 and GAPDH; FIG. 32D depict the effect of 10 µl of *Ailanthi radicis* ethyl acetate extract on the expression of DEF3 and GAPDH; and FIG. 32E depict the effect of 10 µl of *Ailanthi radicis* butyl alcohol extract on the expression of DEF3 and GAPDH.

DESCRIPTION OF SPECIFIC EMBODIMENTS OF THE INVENTION

Figure 1:
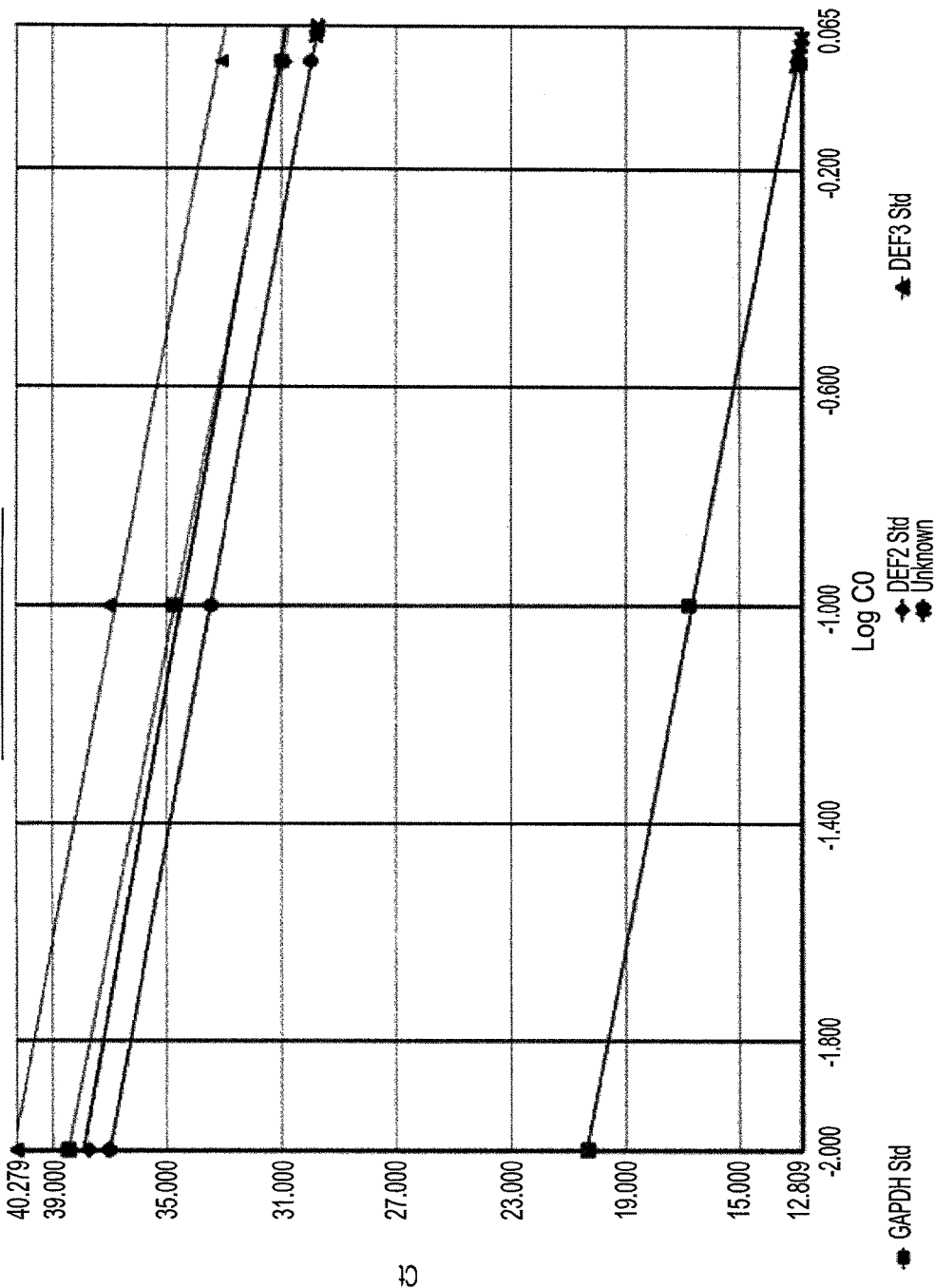
FIG. 1 is a line graph depicting the standard curve for human beta-defensin 3 and GAPDH with successively diluted cDNAs.

The present invention, in some embodiments thereof, relates to plant extracts and, more particularly, but not exclusively, to the use of same for the treatment or prevention of infections including secondary infections of chronic inflammatory diseases.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have developed herbal extract-based compositions for treatment or prevention of infections including for management of secondary infections of chronic inflammatory diseases, such as atopic dermatitis (AD), and which are safe for long-term application. Specifically, the present inventors identified anti-inflammatory herbal extracts which have a stimulating activity on the expression of β-defensins while exhibiting an inhibitory effect on T helper 2 (Th2) cell cytokines.

As is shown hereinbelow and in the Examples section which follows, the present inventors have shown for the first time the dual effect of herbal extracts as stimulators of β-defensins and as inhibitors of IL-13 production. The present inventors have specifically shown that extacts obtained from *Sanguisorbae officinalis, Ailanthus altissima, Galla rhois gallnut, Glycyrrhiza Glabra, Peucedanum praeruptorum* and *Cimicifuga raceomosa* are efficient in upregulating β-defensin expression while downregulating secretion of IL-13 (see Examples 3-4 and 6-7, hereinbelow). The present inventors have further shown the synergistic effect of *Sanguisorbae officinalis* with *Ailanthus altissima* or *Galla rhois gallnut* on stimulation of β-defensins and inhibition of IL-13 production (see Example 8, hereinbelow). Moreover, the present inventors have shown the anti-bacterial effect of *Galla rhois gallnut* against both *S. aureus* and ampicillin-resistant *E. coli* (see Example 9, hereinbelow). The present inventors have further illustrated in a clinical trial the therapeutic efficiency of a cosmetic composition comprising *Sanguisorbae officinalis* root extract, *Ailanthus altissima* extract and a newly formulated cosmetic carrier towards atopic dermatitis (see Example 10, hereinbelow). The results of the clinical trial have shown a significant improvement in the intensity of both objective and subjective parameters (see FIGS. 21-22) as well as in the intensity of the individual symptoms and in the number of patients suffering from the symptoms (see Table 15 and FIG. 25) in subjects affected by mild to severe atopic dermatitis that were treated with the composition comprising *Sanguisorbae officinalis* root extract, *Ailanthus altissima* extract (treatment group) and carrier. Superior activity of the treatment group (42%) vs. carrier (21%) was shown especially in subjects affected by severe atopic dermatitis (SCORAD>50, see FIG. 29). Symptoms characterizing severe atopic dermatitis such as oedema (50% vs. 27%), oozing (86% vs. 39%), excoriation (53% vs. 23%) and lichenification (53% vs. 28%) were improved at higher extent in the treatment group compared to the carrier group (Table 15).

The above results clearly showed superior effect of the treatment group on AD symptoms, particularly on symptoms related to severe AD and to secondary infections. It has been previously shown that the density of *S. aureus* can reach up to $10^7$ colony-forming units/cm$^2$ without clinical signs of infection [see e.g. Goh et al. Int J. Dermatol. (1997) 36(9): 653-7]. Therefore, while no clinical signs of infection were observed in the subjects enrolled in either group of the clinical trial, bacterial colonization most probably existed at least in the severe patients (SCORAD>50). Altogether, the current results substantiate the ability of the two herbal extracts (i.e. *Sanguisorba officinalis* and *Ailanthus*

*altissima*) added to the carrier lotion in treating secondary infections of AD by stimulating beta-defensin and by inhibiting IL-13. The ability to upregulate beta defensin and to downregulate IL-13 provides a platform technology for the treatment of infections such as those associated with chronic inflammation as is the case for AD.

Figure 39A:
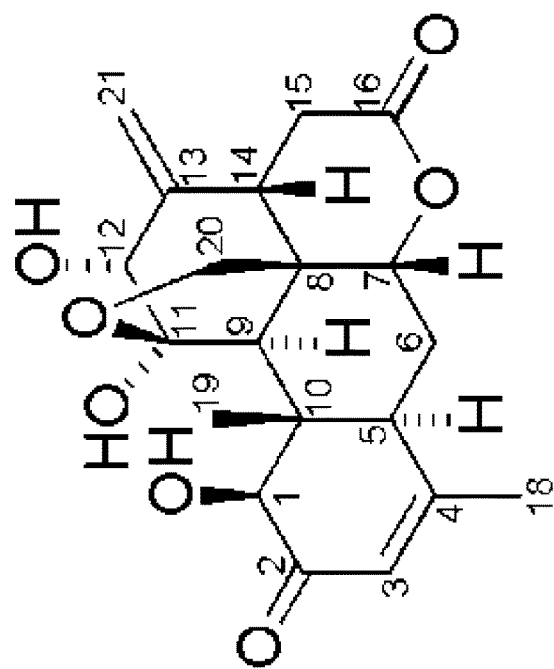
FIGS. 39A-B are illustrations of the structure of the DEF3-stimulating compound, ailanthone, from *Ailanthi radicis* extract.
Figure 39B:
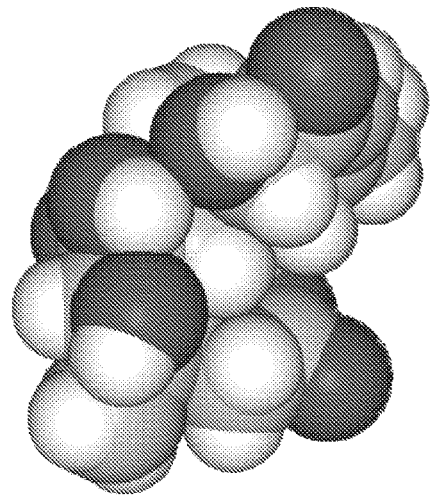

The present inventors have further identified the active ingredient within *Ailanthus altissima*, namely in the bark or the root bark thereof, i.e. *Ailanthi radicis*, which is responsible for expression of β-defensin 3 (DEF3), as ailanthone (see Example 11 and FIGS. 39A-B, hereinbelow). Taken together, these results substantiate the therapeutic and cosmetic value of these herbal extracts and combinations of same for treatment and prevention of infections.

Thus, according to one aspect of the present invention there is provided a method of treating and/or preventing an infection in a subject in need thereof, the method comprising administering to the subject a therapeutically effective amount of each of the compositions which comprise plant extracts or active ingredient thereof as listed below, thereby treating and/or preventing the infection in the subject.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

The term "infection" as used herein refers to a pathological medical condition of any bodily part or tissue in which a pathogenic microorganism causes subsequent tissue inflammation or damage. Examples of infectious diseases which are amenable to treatment by the present compositions include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

According to an embodiment of the present invention, the infection is caused by Gram-negative or Gram-positive bacteria and/or other pathogenic microbes including, without being limited to, *P. aeruginosa, E. coli, Streptococcus pyogenes, Staphylococcus aureus* (e.g. multi-resistant *Staphylococcus aureus*), *Enterococcus faecium* (e.g. vancomycin-resistant *Enterococcus faecium*) or the yeast *Candida albicans*.

According to an embodiment of the present invention, the infection is a skin infection (e.g. a skin wound). Examples of skin infections amenable to treatment by the present compositions include, but are not limited to, bacterial skin infections caused e.g. by *Staphylococcus aureus* or *Streptococcus*, viral skin infections caused e.g. by Herpes Simplex Virus or Herpes Zoster Virus, fungal skin infections and yeast skin infections.

According to a specific embodiment, the present invention contemplates treatment of infectious wounds, such as those occurring as secondary infections of atopic dermatitis.

The term "wound" as used herein refers broadly to injuries to the skin and subcutaneous tissue as well as internal organs initiated in any one of a variety of ways (e.g., wounds afflicted by an infectious organism) and with varying characteristics. Exemplary examples include, but are not limited to, bruises, scrapes, burn wounds, sunburn wounds, incisional wounds, excisional wounds, surgical wounds, necrotizing fasciitis, ulcers, venous stasis ulcers, diabetic ulcers, decubitus ulcers, aphthous ulcers, pressure ulcers, lesions, scars, alopecia greata, dermatitis, allergic contact dermatitis, atopic dermatitis, colitis, berloque dermatitis, diaper dermatitis, dyshidrotic dermatitis, psoriasis, eczema, erythema, warts, anal warts, angioma, cherry angioma, athlete's foot, atypical moles, basal cell carcinoma, Bateman's purpura, bullous pemphigoid, candida, chondrodermatitis helicis, Clark's nevus, cold sores, condylomata, cysts, Darier's disease, dermatofibroma, Discoid Lupus Erythematosus, nummular eczema, atopic eczema, dyshidrotic eczema, hand eczema, Multiforme Erythema Nodosum, Fordyce's Condition, Folliculitis Keloidalis Nuchae, Folliculitis, Granuloma Annulare, Grover's Disease, heat rash, herpes simplex, herpes zoster (shingles), Hidradenitis Suppurativa, Hives, Hyperhidrosis, Ichthyosis, Impetigo, Keratosis Pilaris, Keloids, Keratoacanthoma, Lichen Planus, Lichen Planus Like Keratosis, Lichen Simplex Chronicus, Lichen Sclerosus, Lymphomatoid Papulosis, Lupus of the Skin, Lyme Disease, Lichen Striatus, Myxoid Cysts, Mycosis Fungoides, Molluscum Contagiosum, Moles, Nail Fungus, Necrobiosis Lipoidica Diabeticorum, Nummular Dermatitis, Onychoschizia, Onychomycosis, Pityriasis Lichenoides, Pityriasis Rosea, Pityriasis Rubra Pilaris, Plantar Warts, Poison Ivy, Poison Oak, Pompholyx, Pseudofolliculitis Barbae, Pruritus Ani and Pityriasis Alba.

Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" used herein refers to wounds that encompass Grades I-III; examples of partial thickness wounds include burn wounds, pressure sores, venous stasis ulcers, and diabetic ulcers.

The term "deep wound" used herein is meant to include both Grade III and Grade IV wounds.

The term "chronic wound" used herein refers to a wound that has not healed within thirty days.

The term "healing" in respect to a wound refers to the process of repairing a wound such as by scar formation.

In a specific embodiment, compositions of some embodiments of the present invention promote i.e., accelerate the healing process.

As used herein, the term "preventing" refers to keeping a disease, disorder or condition from occurring in a subject. In some cases the subject may be at risk for developing the disease, but has not yet been diagnosed as having the disease.

Typical subjects that may be treated according to this aspect of the present invention include mammals such as human beings or domesticated animals including, but not limited to, horses (i.e. equine), cattle, goat, sheep, pig, dog, cat, camel, alpaca, llama and yak, male or female, at any age that is in need of treatment or prevention of an infectious disease.

The present invention contemplates treating all types of infections, including primary infections and secondary infections which occur as a result of inflammatory diseases (e.g. chronic inflammatory diseases).

As used herein, the phrase "chronic inflammatory disease" refers to any medical condition which is characterized by persistent inflammation.

Examples of inflammation-associated medical conditions include, but are not limited to, allergic diseases, inflammatory respiratory diseases, inflammatory pulmonary diseases, autoimmune diseases, inflammatory malignant diseases, inflammatory transplantation-related diseases, inflammatory degenerative diseases, inflammatory injuries, inflammatory oral diseases, inflammatory eye conditions, inflammatory skin diseases, diseases associated with hypersensitivity, inflammatory cardiovascular diseases, inflammatory glandular diseases, inflammatory gastrointestinal diseases, inflammatory cutaneous diseases, inflammatory hepatic diseases, inflammatory neurological diseases, inflammatory musculo-skeletal diseases, inflammatory renal diseases, inflammatory systemic diseases, inflammatory connective tissue diseases, inflammatory tumors, necrosis, and/or inflammatory implant-related diseases.

Examples of allergic diseases include, but are not limited to, asthma, hives, urticaria, a pollen allergy, a dust mite allergy, a venom allergy, a cosmetics allergy, a latex allergy, a chemical allergy, a drug allergy, an insect bite allergy, an animal dander allergy, a stinging plant allergy, a poison ivy allergy, anaphylactic shock, anaphylaxis, allergic airway inflammation and a food allergy.

Examples of inflammatory pulmonary diseases include, but are not limited to, asthma, allergic asthma, emphysema, chronic obstructive pulmonary disease and bronchitis.

Examples of inflammatory respiratory diseases include, but are not limited to, acute respiratory infection (caused by e.g. *Chlamydophila pneumonia*).

Examples of inflammatory eye conditions include, but are not limited to, contact lens exposure (caused by e.g. *P. aeruginosa keratitis*).

Examples of inflammatory oral diseases include, but are not limited to, ulcerative lesions.

Examples of hypersensitivities include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, and TH2 lymphocyte mediated hypersensitivity.

Examples of inflammatory cardiovascular diseases include, but are not limited to, occlusive disease, atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease, and anti-helper T lymphocyte autoimmunity.

Examples of inflammatory glandular diseases include, but are not limited to, pancreatic disease and Type I diabetes.

Examples of inflammatory gastrointestinal diseases include, but are not limited to, colitis, ileitis, Crohn's disease, chronic inflammatory intestinal disease, inflammatory bowel syndrome, chronic inflammatory bowel disease, celiac disease, an ulcer, a gastric ulcer, a peptic ulcer, a buccal ulcer, a nasopharyngeal ulcer, an esophageal ulcer, a duodenal ulcer and a gastrointestinal ulcer.

Examples of inflammatory cutaneous diseases include, but are not limited to, acne, autoimmune bullous skin disease, pemphigus vulgaris, bullous pemphigoid, pemphigus foliaceus, contact dermatitis and drug eruption.

Examples of inflammatory hepatic diseases include, but are not limited to, autoimmune hepatitis, hepatic cirrhosis, and biliary cirrhosis.

Examples of inflammatory neurological diseases include, but are not limited to, multiple sclerosis, Alzheimer's disease, Parkinson's disease and myasthenia gravis.

Examples of inflammatory connective tissue diseases include, but are not limited to, autoimmune myositis, primary Sjogren's syndrome, smooth muscle autoimmune disease, myositis, tendinitis, a ligament inflammation, chondritis, a joint inflammation, a synovial inflammation, carpal tunnel syndrome, arthritis, rheumatoid arthritis, osteoarthritis, ankylosing spondylitis, a skeletal inflammation, an autoimmune ear disease, and an autoimmune disease of the inner ear.

Examples of inflammatory renal diseases include, but are not limited to, autoimmune interstitial nephritis and/or renal cancer.

Examples of inflammatory systemic diseases include, but are not limited to, systemic lupus erythematosus, systemic sclerosis, septic shock, toxic shock syndrome, and cachexia.

Examples of inflammatory transplantation-related diseases include, but are not limited to, graft rejection, chronic graft rejection, subacute graft rejection, acute graft rejection hyperacute graft rejection, and graft versus host disease.

Examples of inflammatory tumors include, but are not limited to, malignant tumors, benign tumors, solid tumors, metastatic tumors and non-solid tumors.

Examples of inflammatory injuries include, but are not limited to, an abrasion, a bruise, a cut, a puncture wound, a laceration, an impact wound, a concussion, a contusion, a thermal burn, frostbite, a chemical burn, a sunburn, a desiccation, a radiation burn, a radioactivity burn, a smoke inhalation, a torn muscle, a pulled muscle, a torn tendon, a pulled tendon, a pulled ligament, a torn ligament, a hyperextension, a torn cartilage, a bone fracture, a pinched nerve and a gunshot wound.

Examples of inflammatory skin diseases include, but are not limited to, a skin eczema, a skin ulcer, a bed/pressure sore, a lesion, a dermatitis (e.g. atopic dermatitis, an occupational dermatitis), a poison ivy, an acne, a rosacea and a hive.

According to an embodiment of the present invention, the chronic inflammatory disease is an atopic disease, a contact dermatitis, a nummular dermatitis, a radiation dermatitis, a burn, a non-atopic eczema, a pressure sore, an asthma, a cancer, an eye inflammatory disease, a respiratory infection, an oral infections disease, an allergic airway inflammation, an inflammatory bowl disease (IBD), a Crohn's disease or an ulcerative colitis.

According to a specific embodiment of the present invention, the chronic inflammatory disease is atopic dermatitis (AD).

Regardless of the indication, a therapeutically effective amount of a composition comprising the plant extract or a unit dosage form which comprises the same is administered to the subject.

As used herein, the term "plant extract" refers to any extract obtainable from a plant or any portion thereof. Typically the plant extract comprises the active ingredient/s thereof.

Thus, the plant extract may be obtained from the fruit, the skin or rind of the fruit, the seeds, the bark, the leaves, the roots, the rhizome, the root bark or the stem of a plant or a combination of same.

The plant extracts of the present invention are typically obtained from *Ailanthus altissima, Cimicifuga raceomosa,*

*Galla rhois gallnut, Glycyrrhiza Glabra* (Licorice), *Peucedanum praeruptorum, Sanguisorbae officinalis, Silybum marianum, Saposhnikovia divaricata, Radix Tripterygii wilfordii, Celosia argentea, Coptis Root, Radix Salviae miltiorrhizae, Saururus Chinensis* (e.g. Leaves), *Calendula officinalis, Gentiana, Mentha aquatica* L, Dandelion Root/ *Taraxacum officinale*, Broom Cypress Fruit, *Anemarrhena asphodeloides, Stellaria dichotoma* L. var. *lanceolate*. Root, *Fritillaria verticillate, Actinidia polygama, Phellodendron amurense, Sapindus mukurossi, Radix Sophora flarescents, Cnidium monnieri, Camelia japonica, Scutellaria baicalensis, Rheum palmatum, Chrysanthemum indicum, Portulaca oleracea*, Peony Bark, *Angelica sinensis, Astragalus membranaceus* Root, *Evodia rutaecarpa fruit, Polygonum cuspidatum, Smilax glabra rhizoma, Curcuma longa*, Indigo naturalis, *Semen Hydnocarpi hainanensi, Tripterygii wilfordii, Salviae miltiorrhizae, Camelia japonica, Scutellaria baicalensis, Rheum palmatum, Peonia suffruticasa, Rubi fructus, Lysimachiae foenumgraeci herba, Ailanthi radicis cortex, Peucedani radix, Terminariae fructus, Coptidis rhizome* and *Albizziae cortex* plants.

According to an embodiment of the invention, the plant extract is an aqueous extract, a hydrophilic extract, a non-polar extract or a polar extract.

According to an embodiment of the present invention, the plant extract is obtained from *Sanguisorbae officinalis.*

According to a specific embodiment, the plant extract is obtained from a *Sanguisorba Officinalis* root.

According to an embodiment of the present invention, the plant extract is obtained from *Ailanthus altissima.*

According to an embodiment, the plant extract is obtained from the bark or the root bark of *Ailanthus altissima* (i.e. Ailanthi Cortex). Thus, according to another embodiment, the *Ailanthus altissima* plant extract consists of an *Ailanthi radicis* plant extract.

According to an embodiment of the present invention, the plant extract is obtained from *Galla rhois gallnut.*

According to an embodiment of the present invention, the plant extract is obtained from *Glycyrrhiza Glabra.*

According to an embodiment of the present invention, the plant extract is obtained from *Rheum palmatum.*

According to a specific embodiment, the plant extract is obtained from a *Rheum palmatum* root.

According to an embodiment of the present invention, the plant extract is obtained from *Scutellaria baicalensis.*

According to a specific embodiment, the plant extract is obtained from a *Scutellaria baicalensis* root.

According to an embodiment of the present invention, the plant extract is obtained from *Peucedanum praeruptorum.*

According to an embodiment of the present invention, the plant extract is obtained from *Cimicifuga raceomosa.*

Certain combinations are also contemplated. Such are listed below.

The plant extracts may be further treated to purify those active ingredients such as those having anti-infectious activity. Methods of determining anti-bacterial activity or bactericidal activity are well known in the art and include, without limitation, paper diffusion, disk diffusion, broth dilution, and agar dilution anti-microbial assays (some of which are listed hereinbelow and in the examples section which follows). The active ingredients present in the plant extracts of the present invention include, but are not limited to, Ailanthone, Mersosin, Toosendanin, General Ginsenoide, Galic acid, Liquiritin, Praeruptorin A, Tannic acid and Silybin. Active ingredients may be purified from plant extracts or used synthetically. The concentration may be determined by the above-mentioned assays and the specific ranges provided for ailanthone below can be implemented for other active ingredients.

According to an embodiment, the active ingredient in a plant extract is Ailanthone.

As used herein, the term "Ailanthone" or 11.beta.,20-epoxy-1.beta.,11.alpha.,12.alpha.-trihydroxypicrasa-3,13 (21)-diene-2,16-dione relates to the compound contained in the bark of "tree of heaven" (Japanese name "Shinju" or "Niwaurushi"; *Ailanthus altissima*, Swingle, Simarubaceae), and its derivatives such as described in U.S. Pat. Nos. 4,665,201 and 4,774,342 herein incorporated by reference. The term relates to naturally occurring (plant purified) or synthetic compounds.

According to an embodiment, when the plant comprises *Ailanthi altissima*, the active ingredient comprises Ailanthone.

According to another embodiment, the *Ailanthi altissima* plant extract comprises at least about 0.01%, at least about 0.05%, at least about 0.1%, at least about 0.25%, at least about 0.5%, at least about 1%, at least about 2.5% or at least about 5% Ailanthone.

Specifically contemplated ranges of each of the active ingredients described above (e.g., Ailanthone include 0.01-5%, 0.05-2.5%, 0.05-1%, 0.01-1%).

According to an embodiment compositions which comprise Ailanthone are devoid of *Ailanthus* materials such as cellulose, protein and other secondary metabolites.

Plant extracts are typically divided into polar and non-polar extracts and hydrophilic and hydrophobic extracts.

Thus, the plant extracts may be purified by the use of a polar solvent (i.e. polar extract) such as, without being limited to, ethyl alcohol (ethanol), butyl alcohol (butanol), methanol, water or propanol. The polar extracts of the present invention may comprise any percentage of polar solvent including for example 1-10% polar solvent, 10-20% polar solvent, 20-30% polar solvent, 30-40% polar solvent, 40-50% polar solvent, 50-60% polar solvent, 70-80% polar solvent, 80-90% polar solvent and 90-100% polar solvent.

Alternatively, the plant extracts may be purified by the use of a non-polar solvent (i.e. non-polar extract) such as, without being limited to, isooctane. The non-polar extracts of the present invention may comprise any percentage of non-polar solvent including for example 1-10% non-polar solvent, 10-20% non-polar solvent, 20-30% non-polar solvent, 30-40% non-polar solvent, 40-50% non-polar solvent, 50-60% non-polar solvent, 70-80% non-polar solvent, 80-90% non-polar solvent and 90-100% non-polar solvent.

Typically, hydrophobic molecules tend to be non-polar and thus prefer other neutral molecules and non-polar solvents, alternatively, hydrophilic molecules tend to be polar and dissolve by water and other polar substances.

Thus, the plant extracts of the present invention can be produced by any method known in the art including a polar extract such as a water (aqueous) extract or an alcohol extract (e.g., butanol, ethanol, methanol, hexane, hydroalcohol, see for example Swanson R L et al., 2004, Biol. Bull. 206: 161-72) or a non-polar extract (e.g., isooctane, see for example, Ng L K and Hupe M. 2003, J. Chromatogr A. 1011: 213-9; Diwanay S, et al., 2004, J. Ethnopharmacol. 90: 49-55.

Regardless of the exact solvent employed, plant extracts are typically made by placing a plant sample (e.g., leaves, seeds) in a mortar along with a small quantity of liquid (e.g., 10 ml of water, alcohol or an organic solvent for every 2 grams of plant sample) and grinding the sample thoroughly using a pestle. When the plant sample is completely ground, the plant extract is separated from the ground plant material via, centrifugation, filtering, cation-exchange chromatography, etc., and the collected liquid is further processed if need be (via a concentrating column etc.), active ingredients can be separated from this extract via affinity chromatography, mass chromatography and the like.

An exemplary method, according to some embodiments of the present invention, for obtaining a *Ailanthi radicis* plant extract comprises placing the dried plant sample (e.g., bark or root bark of *Ailanthus altissima*) in boiling water (e.g. for 3 hrs) and then optionally freeze-drying the hot water extract at −60° C. at reduced pressure. Next, the freeze-dried extract may be re-dissolved with a polar extract such as $H_2O$, ethyl acetate (EtOAc) or butyl alcohol (n-BuOH). The collected plant extract may then be further processed if need be (via a concentrating column etc.) and the active ingredients can be separated from this extract via, for example, high-performance liquid chromatography (HPLC) and the like.

According to a specific embodiment, the plant extract of the present invention is an aqueous extract. In order to obtain a purified plant extract (e.g. with reduced levels of organic salts and/or heavy metals and/or starch in the plant extract), the aqueous plant extract is typically further purified using a resin chromatography such as a macroporous resin or other chromatography methods.

Thus, according to another embodiment, there is provided a method of preparing a composition for treating and/or preventing an infection, the method comprising: (a) subjecting a plant to ×1-10 volumes of water to produce an extract of the plant; and (b) reducing the amount of organic salts and/or heavy metals and/or starch in the plant extract using a macroporous resin which results in an elevated content of an active ingredient which is present in the plant extract.

Plant extracts of the present invention can also be obtained from a variety of commercial sources such as, for example, from Crodarom (Crodarom SAS, Chanac, France).

The compositions of the present invention may comprise a single plant extract or may comprise several plant extracts.

Thus, according to one embodiment of the present invention, the composition comprises a *Sanguisorbae officinalis* plant extract and at least one additional plant extract selected from the group consisting of an *Ailanthus altissima* plant extract, a *Galla rhois gallnut* plant extract and a *Glycyrrhiza Glabra* plant extract.

According to another embodiment of the present invention, the composition comprises an aqueous plant extract, wherein the plant is selected from the group consisting of *Galla rhois gallnut*, *Peucedanum praeruptorum* and *Cimicifuga raceomosa*.

According to another embodiment of the present invention, the composition comprises a *Sanguisorbae officinalis* plant extract, an *Ailanthus altissima* plant extract and a *Glycyrrhiza Glabra* plant extract.

According to another embodiment of the present invention, the composition comprises a *Sanguisorbae officinalis* plant extract, an *Ailanthus altissima* plant extract and a *Galla rhois gallnut* plant extract.

According to another embodiment of the present invention, the composition comprises a *Sanguisorbae officinalis* plant extract and an *Ailanthus altissima* plant extract.

According to another embodiment of the present invention, the composition comprises a *Sanguisorbae officinalis* plant extract and a *Galla rhois gallnut* plant extract.

According to another embodiment of the present invention, the composition comprises a *Sanguisorbae officinalis* plant extract and a *Glycyrrhiza Glabra* plant extract.

According to another embodiment of the present invention, the composition comprises a *Sanguisorbae officinalis* plant extract and a *Rheum palmatum* plant extract.

According to another embodiment of the present invention, the composition comprises a *Sanguisorbae officinalis* plant extract and a *Scutellaria baicalensis* plant extract.

According to another aspect of the present invention, the composition comprises an *Ailanthus altissima* plant extract and at least one additional plant extract selected from the group consisting of a *Galla rhois gallnut* plant extract, a *Glycyrrhiza Glabra* plant extract, a *Rheum palmatum* plant extract and a *Scutellaria baicalensis* plant extract.

According to another embodiment of the present invention, the composition comprises an *Ailanthus altissima* plant extract and a *Galla rhois gallnut* plant extract.

According to another embodiment of the present invention, the composition comprises an *Ailanthus altissima* plant extract and a *Glycyrrhiza Glabra* plant extract.

According to another embodiment of the present invention, the composition comprises an *Ailanthus altissima* plant extract and a *Rheum palmatum* plant extract.

According to another embodiment of the present invention, the composition comprises an *Ailanthus altissima* plant extract and a *Scutellaria baicalensis* plant extract.

It will be appreciated that the concentration of each of the plant extracts within the composition may vary. Thus, a concentration of each of the plant extracts within the composition may be in a range of about 0.01 to 10%, 0.05 to 9%, 0.1 to 8%, 0.15 to 7%, 0.2 to 6%, about 0.25 to 5%, about 0.3 to 4%, about 0.4 to 3%, about 0.5 to 2%, about 1 to 2% or about 0.1 to 1%.

According to a specific embodiment, the concentration of the plant extract within the composition is about 0.5 to 2%. According to a further specific embodiment the concentration of the plant extract within the composition is about 1%.

According to another aspect of the present invention, there is provided a composition comprising Ailanthone at a concentration of at least about 0.01% and a cosmetically or a pharmaceutically acceptable carrier.

According to an embodiment, the composition comprising Ailanthone further comprises *Sanguisorbae officinalis* plant extract. Such as at the ranges described herein.

According to an embodiment, the composition comprising Ailanthone further comprises an additional plant extract, such as e.g. a *Galla rhois gallnut* plant extract, a *Glycyrrhiza Glabra* plant extract a *Rheum Palmatum* Root Extract, a *Cnidium Monnieri* Fruit Extract and a *Scutellaria Baicalensis* Root Extract.

According to an embodiment, the composition comprising Ailanthone further comprises Dipotassium Glycyrrhizate.

It will be appreciated that the concentration of Ailanthone within the composition may vary. Thus, a concentration of Ailanthone within the composition may be in a range of about 0.01 to 10%, about 0.01 to 7%, about 0.01 to 5%, about 0.01 to 3%, about 0.01 to 2%, about 0.01 to 1%, about 0.01 to 0.5%, about 0.01 to 0.3%, about 0.01 to 0.2% or about 0.01 to 0.1%.

According to an embodiment, the compositions of the present invention may be formulated for topical, oral, ocular or pulmonary (e.g. for inhalation) administration. Other formulations are described hereinbelow and are within the scope of the invention.

The compositions of the present invention can be administered to the subject per se or in a pharmaceutical or cosmetic composition.

As used herein a "pharmaceutical or cosmetic composition" refers to a preparation of the active ingredients described herein with other chemical components such as physiologically suitable carriers and excipients. The purpose of the composition is to facilitate administration of the active ingredients (e.g., plant extract) to the subject.

As used herein the term "active ingredient" refers to the plant extract compositions accountable for the intended biological effect (i.e., for treatment or prevention of an infection).

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the composition (pharmaceutical composition or cosmetic composition) to further facilitate administration of an active ingredient of the present invention.

Techniques for formulation and administration of drugs may be found in "Remington's Pharmaceutical Sciences," Mack Publishing Co., Easton, Pa., latest edition, which is incorporated herein by reference.

Each of the compositions of the present invention may comprise the plant extracts in a co-formulation or in separate compositions (e.g. two formulations, three formulations etc.). When not co-formulated, administration of the plant extract compositions may be effected concomitantly or sequentially.

In any case, the compositions may be formulated for numerous types of administrations.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the composition in a local rather than systemic manner, for example, by injecting the composition including the active ingredient (e.g., plant extracts) and a physiologically acceptable carrier directly into a tissue region of a patient (e.g. into a healthy skin that surrounds the infected skin)

Suitable routes of administration of the compositions may, for example, include ocular (e.g., to the eye), topical (e.g., to a keratinous tissue, such as the skin, hair, nail, scalp), transdermal, subdermal, pulmonary and oral (e.g., by mouth) administrations.

According to an embodiment, the composition of the present invention is administered topically, pulmonary (e.g. via inhalation), orally or ocularly.

As used herein the phrase "oral administration" refers to administration of the composition of the present invention by mouth e.g. in the form of a liquid, a solution, a tablet, a capsule or an elixir.

As used herein the phrase "dermal administration" refers to applying or spreading the composition of the present invention onto the surface of the body, i.e. skin, scalp, hair, nails and the like, preferably on the surface affected by the infection.

As used herein the phrase "transdermal administration" refers to administration of the compositions of the present invention across the skin for systemic administration (e.g. via transdermal patches or by transdermal implants). The transdermal administration is typically effected in close proximity to the site of infection, however, transdermal administration may be carried out in any anatomical location as see fit by one of ordinary skill in the art.

As used herein the phrase "subdermal administration" refers to administering the compositions of the present invention under the skin (i.e. completely buried in the skin, e.g. via subdermal implants). The subdermal administration is typically effected in close proximity to the site of the infection, however, subdermal administration may be carried out in any anatomical location as see fit by one of ordinary skill in the art.

Compositions of the present invention may be manufactured by processes well known in the art, e.g., by means of conventional mixing, dissolving, granulating, dragee-making, levigating, emulsifying, encapsulating, entrapping or lyophilizing processes.

Compositions for use in accordance with some embodiments of the invention thus may be formulated in conventional manner using one or more physiologically acceptable carriers comprising excipients and auxiliaries, which facilitate processing of the active ingredients into preparations which, can be used cosmetically or pharmaceutically. Proper formulation is dependent upon the route of administration chosen.

For injection, the active ingredients of the composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the composition can be formulated readily by combining the active compounds with carriers (e.g. pharmaceutically acceptable carriers) well known in the art. Such carriers enable the composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The composition of some embodiments of the invention may also be formulated in rectal compositions such as suppositories or retention enemas, using, e.g., conventional suppository bases such as cocoa butter or other glycerides.

Compositions suitable for use in context of some embodiments of the invention include compositions wherein the active ingredients are contained in an amount effective to achieve the intended purpose.

As used herein the phrase "therapeutically effective amount" refers to an amount of an active ingredient (i.e. plant extract composition or an active ingredient thereof, as described above) effective in preventing or treating an infection. The therapeutically effective amount of the composition of the present invention is also effective in down-regulating secretion of a Th2 type cytokine (e.g. IL-4, IL-5, IL-6, IL-10, IL-13, etc.) from a cell of the subject (e.g. basophilic cell, see e.g. Examples 3 and 6 of the Examples section which follows). The therapeutically effective amount of the composition of the present invention is further effective in upregulating (e.g. stimulating) expression of a human beta-defensin (e.g. human beta-defensin 3) in a cell of the subject (e.g. keratinocyte cell, see e.g. Examples 4 and 7 of the Examples section which follows). Furthermore, the therapeutically effective amount of the composition of the present invention may comprise an anti-bacterial activity (e.g. against *S. aureus* and ampicillin-resistant *E. coli*, see e.g. Example 9 of the Examples section which follows).

According to an embodiment, the therapeutically effective amount of Ailanthone comprises a concentration of at least about 0.01%, at least about 0.05%, at least about 0.1%, at least about 0.25%, at least about 0.5%, at least about 1%, at least about 2.5% or at least about 5%, or a range of about 0.01 to 10%, about 0.01 to 7%, about 0.01 to 5%, about 0.01 to 3%, about 0.01 to 2%, about 0.01 to 1%, about 0.01 to 0.5%, about 0.01 to 0.3%, about 0.01 to 0.2% or about 0.01 to 0.1%.

Determination of a therapeutically effective amount is well within the capability of those skilled in the art, especially in light of the detailed disclosure provided herein.

For any preparation used in the method of the invention, the therapeutically effective amount or dose can be estimated initially from in vitro assays. For example, a therapeutically effective amount may be evaluated in-vitro by assaying upregulated (i.e. increased) expression of a human beta-defensin in a cell (e.g. keratinocyte cell line expressing beta-defensin) by e.g. PCR (e.g. real time PCR). Alternatively, a therapeutically effective amount may be evaluated in-vitro by assaying down-regulated (i.e. decreased) secretion of a Th2 type cytokine (e.g. IL-13) from a cell (e.g. basophilic cell line secreting IL-13) by e.g. antibodies (e.g. IL-13 specific monoclonal antibodies).

In addition, a dose can be formulated in tissue cultures systems (e.g. ex-vivo systems) or in animal models to achieve a desired concentration or titer. Such information can be used to more accurately determine useful doses in humans. For example, a therapeutically effective amount can be evaluated in-vivo by determining the level of inflammation before and after administration of the composition in a subject affected by an inflammatory state [e.g. by use of a blood test such as a complete blood count (CBC), by observation of skin wounds and so forth].

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity of the condition (e.g., the area, depth and degree of the infection) and the responsiveness of the subject to treatment, dosing can be of a single or a plurality of administrations, with course of treatment lasting from several days to several weeks, several months or several years, or until cure is effected or diminution of the infection is achieved. Alternatively, the compositions are administered in order to prevent occurrence of an infection in a subject at risk of developing an infection (e.g. a subject suffering from a chronic inflammatory disease). The compositions may be administered for prolonged periods of time (e.g. several days, several weeks, several months or several years) as to prevent occurrence of an infection.

According to an embodiment of the present invention, the compositions of the present invention are administered at least once a day. According to another embodiment, the compositions are administered twice a day, three times a day or more.

According to an embodiment of the present invention, administering is effected chronically.

According to another embodiment, administering is effected for at least about 10 days, 12 days, 14 days, 16 days, 18 days, 21 days, 24 days, 27 days, 30 days, 60 days, 90 days or more.

The amount of a composition to be administered will, of course, be dependent on the subject being treated, the severity of the affliction, the manner of administration, the judgment of the prescribing physician, etc.

The compositions of the present invention may be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an ampule, a dispenser, an adhesive bandage, a non-adhesive bandage, a wipe, a baby wipe, a gauze, a pad and a sanitary pad.

The unit dosage form according to the teachings of the present invention may comprise *Sanguisorbae officinalis* plant extract at a concentration of about 0.5-5% weight/weight, about 0.5-2% weight/weight or according to a specific embodiment about 1% weight/weight.

The unit dosage form according to the teachings of the present invention may further comprise *Ailanthus altissima* plant extract at a concentration of about 0.5-5% weight/weight, about 0.5-2% weight/weight or according to a specific embodiment about 1% weight/weight.

The unit dosage form according to the teachings of the present invention may further comprise *Glycyrrhiza Glabra* plant extract at a concentration of about 0.5-5% weight/weight, about 0.5-2% weight/weight or according to a specific embodiment about 1% weight/weight.

The unit dosage form according to the teachings of the present invention may further comprise *Galla rhois gallnut* plant extract at a concentration of about 0.5-5% weight/weight, about 0.5-2% weight/weight or according to a specific embodiment about 1% weight/weight.

The unit dosage form according to the teachings of the present invention may further comprise *Rheum palmatum* plant extract at a concentration of about 0.5-5% weight/weight, about 0.5-2% weight/weight or according to a specific embodiment about 1% weight/weight.

The unit dosage form according to the teachings of the present invention may further comprise *Scutellaria baicalensis* plant extract at a concentration of about 0.5-5% weight/weight, about 0.5-2% weight/weight or according to a specific embodiment about 1% weight/weight.

The unit dosage form according to the teachings of the present invention may comprise *Ailanthus altissima* plant extract at a concentration of about 0.5-5% weight/weight, about 0.5-2% weight/weight or according to a specific embodiment about 1% weight/weight.

The unit dosage form according to the teachings of the present invention may comprise *Glycyrrhiza Glabra* plant extract at a concentration of about 0.5-5% weight/weight, about 0.5-2% weight/weight or according to a specific embodiment about 1% weight/weight.

The unit dosage form according to the teachings of the present invention may comprise *Galla rhois gallnut* plant extract at a concentration of about 0.5-5% weight/weight, about 0.5-2% weight/weight or according to a specific embodiment about 1% weight/weight.

The unit dosage form according to the teachings of the present invention may comprise *Sanguisorbae officinalis* plant extract at a concentration of about 0.5-5% weight/weight, about 0.5-2% weight/weight or according to a specific embodiment about 1% weight/weight, *Ailanthus altissima* plant extract at a concentration of about 0.5-5% weight/weight, about 0.5-2% weight/weight or according to a specific embodiment about 1% weight/weight and *Glycyrrhiza Glabra* plant extract at a concentration of about 0.5-5% weight/weight, about 0.5-2% weight/weight or according to a specific embodiment about 1% weight/weight.

The unit dosage form according to the teachings of the present invention may comprise *Sanguisorbae officinalis* plant extract at a concentration of about 0.5-5% weight/weight, about 0.5-2% weight/weight or according to a specific embodiment about 1% weight/weight, *Ailanthus altissima* plant extract at a concentration of about 0.5-5% weight/weight, about 0.5-2% weight/weight or according to a specific embodiment about 1% weight/weight and *Galla rhois gallnut* plant extract at a concentration of about 0.5-5% weight/weight, about 0.5-2% weight/weight or according to a specific embodiment about 1% weight/weight.

The unit dosage form according to the teachings of the present invention may comprise a unit dosage form selected from the group consisting of a topical, an oral, a pulmonary or an ocular unit dosage form comprising Ailanthone at a concentration of at least about 0.01% weight/weight, about 0.01-1% weight/weight, about 0.01-2% weight/weight, about 0.01-3% weight/weight, about 0.01-4% weight/weight or about 0.01-5% weight/weight.

The quantity of active compound in a unit dose of preparation may be varied or adjusted according to the particular application.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

Since the compositions of the present invention are utilized in vivo, the compositions are preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Additional factors may be incorporated into the compositions of the present invention (i.e., plant extracts as described hereinabove). These include, but are not limited to, extracellular matrix components (e.g. vitronectin, laminin, collagen, elastin), growth factors (e.g. FGF 1, FGF 2, IGF 1, IGF 2, PDGF, EGF, KGF, HGF, VEGF, SDF-1, GM-CSF, CSF, G-CSF, TGF alpha, TGF beta, NGF and ECGF), growth factors [e.g. erythropoietin, fibroblast growth factor, franulocyte-colony stimulating factor (G-CSF) and granulocyte-macrophage colony stimulating factor (GM-CSF)], hormones (e.g., insulin, growth hormone (GH), CRH, Leptin, Prolactin and TSH), angiogenic factors (e.g., angiogenin and angiopoietin), coagulation and anticoagulation factors [e.g., Factor I, Factor XIII, tissue factor, calcium, vWF, protein C, protein S, protein Z, fibronectin, antithrombin, heparin, plasminogen, low molecular weight heparin (Clixan), high molecular weight kininogen (HMWK), prekallikrein, plasminogen activator inhibitor-1 (PAI1), plasminogen activator inhibitor-2 (PAI2), urokinase, thrombomoduline, tissue plasminogen activator (tPA), alpha 2-antiplasmin and Protein Z-related protease inhibitor (ZPI)], cytokine inhibitors (e.g. Cyclosporin A; Alpha-2-Macroglobulin, Pentamidine, Pentoxifylline, Dexamethasone), chemokine inhibitors (e.g. Peptide 3, NR58.3-14-3), enzymes (e.g. endoglycosidases, exoglycosidases, endonucleases, exonucleases, peptidases, lipases, oxidases, decarboxylases, hydrases, chondroitinase, chondroitinase ABC, chondroitinase AC, hyaluronidase, keratanase, heparanases, heparanase splice variance, collagenase, trypsin, catalases), neurotransmitters, neuropeptides (e.g. substance P), vitamins (e.g., D-biotin, Choline Chloride, Folic acid, Myo-inositol, Niacinamide, D-Pantothenic acid, Calcium salts, Pyridoxal.HCl, Pyrodixine.HCl, Riboflavin, Thiamine.HCl, Vitamin B12, vitamin E, vitamin C, vitamin D, vitamin B1-6, vitamin K, vitamin A and vitamin PP), carbohydrates (e.g. Mono/Di/Polysacharides including glucose, mannose, maltose and fructose), ions, chelators (e.g. Fe chelators, Ca chelators), antioxidants (e.g., Vitamin E, Quarcetin, superoxide scavengers, Superoxide dismutase, H2O2 scavengers, free radicals scavengers, Fe scavengers), fatty acids (e.g., Triglycerides, Phospholipids, Cholesterols, free fatty acids and non free fatty acids, fatty alcohol, Linoleic acid, oleic acid and lipoic acid), antibiotics (e.g., Penicillins, Cephalosporins and Tetracyclines), amino acids (e.g., essential and non essential (from A-Z) especially glutamine and arginine), salts (e.g., prurivat salts and sulfate salts), sulfates (e.g. Calcium Sulfate), steroids (e.g., androgens, estrogens, progestagens, glucocorticoids and mineralocorticoids), analgesics, anesthetics, anti-bacterial agents, anti-yeast agents, anti-fungal agents, anti-viral agents, pro-biotic agents, anti-protozal agents, anti-pruritic agents, anti-dermatitis agents, anti-emetics, anti-inflammatory agents, anti-hyperkeratolyic agents, antiperspirants, anti-seborrheic agents, antihistamine agents, hypoxia inducible factors (e.g. HIF-1 alpha and beta and HIF-2), catecholamines (e.g., Epinephrine and Norepinephrine), Nucleosides and Nucleotides (e.g., Purins and Pyrimidines), Prostaglandins (e.g. Prostaglandin E2), Leucotriens, Erythropoietins (e.g. Thrombopoietin), Proteoglycans (e.g. Heparan sulfate, keratan sulfate), Hydroxyapatites [e.g. Hydroxyapatite $(Ca_{10}(PO_4)_6(OH)_2)$], Haptoglobins (Hp1-1, Hp2-2 and Hp1-2), Superoxide dismutases (e.g. SOD 1/2/3), Nitric Oxides, Nitric Oxide donors (e.g. nitroprusside, Sigma Aldrich, St. Louis, Mo., USA, Glutathione peroxidases, Hydrating compounds (e.g. vasopressin), cells (e.g. Platelets), cell medium (e.g. M199, DMEM/F12, RPMI, Iscovs), serum (e.g. human serum, fetal calf serum, fetal bovine serum), buffers (e.g., HEPES, Sodium Bicarbonate), detergents (e.g., Tween), disinfectants, herbs, fruit extracts, vegetable extracts (e.g. cabbage, cucumber), flower extracts, additional plant extracts, flavinoids (e.g. pomegranate juice), spices, leafs (e.g. Green tea, Chamomile), Polyphenols (e.g. Red Wine), honey, lectins, microparticles, nanoparticles (lyposomes), micelles, calcium carbonate (CaCO3, e.g. precipitated calcium carbonate, ground/pulverized calcium carbonate, albacar, PCC, GCC), calcite, limestone, crushed marble, ground limestone, lime, and chalk (e.g. whiting chalk, champagne chalk, french chalk).

According to a specific embodiment, the compositions of the present invention do not comprise beta-defensins.

The present formulation may also contain ingredients, substances, elements and materials containing, hydrogen, alkyl groups, aryl groups, halo groups, hydroxy groups, alkoxy groups, alkylamino groups, dialkylamino groups, acyl groups, carboxyl groups, carboamido groups, sulfonamide groups, aminoacyl groups, amide groups, amine groups, nitro groups, organo selenium compounds, hydrocarbons, and cyclic hydrocarbons.

The present formulation may be combined with substances such as benzol peroxide, vasoconstrictors, vasodilatators, salicylic acid, retinoic acid, azelaic acid, lactic acid, glycolic acid, pyreuric acid, tannins, benzlidenecamphor and derivatives thereof, alpha hydroxyis, surfactants.

Compositions of some embodiments of the present invention may be bioconjugated to polyethylenglycol (e.g. PEG, SE-PEG) which preserves the stability (e.g., against protease activities) and/or solubility (e.g., within a biological fluid such as blood, digestive fluid) of the active ingredients (i.e. plant extract compositions of the present invention) while preserving their biological activity and prolonging its half-life.

In addition to the pharmaceutically effective amount of an agent disclosed herein, the compositions of this aspect of the present invention also include a dermatologically or a cosmetic acceptable carrier.

The phrases "dermatologically acceptable carrier or diluent" or "cosmetically acceptable carrier or diluent", refer to a carrier which is suitable for topical application onto the skin, i.e., keratinous tissue, has good aesthetic properties, is compatible with the active agents of the present invention and any other components, and is safe and non-toxic for use in mammals.

It will be appreciated that the carrier (e.g. cosmetically acceptable carrier, pharmaceutically acceptable carrier) of the present invention may comprise ingredients (e.g. plant extracts) which aid in treatment of a medical condition (e.g. atopic dermatitis).

Thus, the carrier of some embodiments of the present invention comprises at least one plant extract.

According to one embodiment, the plant extract within the carrier comprises a *Rheum Palmatum* Root Extract, a *Cnidium Monnieri* Fruit Extract and/or a *Scutellaria Baicalensis* Root Extract.

According to an embodiment, the carrier may further comprise Dipotassium Glycyrrhizate.

According to one embodiment, the cosmetic carrier comprising a *Rheum Palmatum* Root Extract, a *Cnidium Monnieri* Fruit Extract, a *Scutellaria Baicalensis* Root Extract and Dipotassium Glycyrrhizate.

In order to enhance the percutaneous absorption of the active ingredients (e.g., plant extracts of the present invention), one or more of a number of agents can be added to the pharmaceutical or cosmetic compositions including, but not limited to, dimethylsulfoxide, dimethylacetamide, dimethylformamide, surfactants, azone, alcohol, acetone, propylene glycol and polyethylene glycol.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion, a soap, a paste, an emulsion, a gel, a spray or an aerosol.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Examples of suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986), each of which is fully incorporated by reference in its entirety.

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form.

The compositions of the present invention can be formulated in any of a variety of forms utilized by the pharmaceutical or cosmetic industries for skin application including solutions, lotions, sprays, creams, ointments, salves, gels, oils, wash, shampoos, conditioners etc., as further described below.

The pharmaceutical or cosmetic compositions of the present invention may be formulated viscous enough to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The compositions of the subject invention, including but not limited to lotions and creams, may comprise a dermatologically or cosmetically acceptable moisturizers and/or emollient. As used herein, "emollient" refers to a material useful for the prevention or relief of dryness, as well as for the protection of the skin. Wide varieties of suitable emollients are known and may be used herein. See, e.g., Sagarin, Cosmetics, Science and Technology, 2nd Edition, Vol. 1, pp. 3243 (1972), which contains numerous examples of materials suitable as an emollient and is fully incorporated herein by reference. An exemplary emollient is glycerin. Additional emollients which may be used include, but are not limited to, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, lauric, isostearic, palmitic, and the like. Emollients also include fatty alcohols having ten to twenty carbon atoms, such as cetyl, myristyl, lauryl, isostearyl, stearyl and the like.

According to an embodiment, the cosmetic composition of the present invention comprises a *Sanguisorbae officinalis* plant extract, an *Ailanthus altissima* plant extract, a *Rheum Palmatum* Root Extract, a *Cnidium Monnieri* Fruit Extract, a *Scutellaria Baicalensis* Root Extract and Dipotassium Glycyrrhizate.

According to an embodiment, the cosmetic composition further comprises a moisturizer and an emollient.

The composition of the present invention may also include additional components which are added, for example, in order to enrich the compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

As mentioned above, the compositions of the present invention can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

It will be appreciated that compositions of the present invention can be used in combination with other currently practiced therapies such as, without being limited to, photo/light therapy [e.g., light therapy for inflammatory dermatitis] and antibiotic therapy (e.g. local or systemic).

According to another embodiment of the present invention, there is provided a method of identifying an agent having inflammatory modulator properties, the method comprising: (a) contacting the agent with a cell; and (b) assaying secretion of a human beta-defensin from the cell, wherein an upregulation in the beta-defensin secretion following the contacting is indicative that the agent has an inflammatory modulator properties.

According to an embodiment, the agent comprises a plant extract or active ingredient thereof.

As used herein, the term "upregulating" refers to the increased levels of RNA and/or protein or to DNA copy number of human beta-defensins in a cell which results in an increased secretion of the beta-defensin from the cell.

Typically, the level of the human beta-defensins is increased from the level of same in cells not treated with the plant extracts. Determining the level of human beta-defensins in cells not treated with plant extracts is preferably effected along-side to detect an elevated expression.

It will be appreciated that any cell which naturally expresses human beta-defensin or which was genetically modified to express beta-defensin may be used according to the present teachings for assaying upregulated (i.e. increased) expression of human beta-defensin (e.g. human beta-defensin 3, beta-defensin 2 or beta-defensin 1). According to a specific embodiment the cell is epithelial cells (e.g. keratinocyte cell).

Any method known in the art for detecting expression of a human beta-defensin polynucleotide or polypeptide may be used in accordance with the present teachings.

Thus, for example, RNA detection methods such as Northern blot analysis, reverse-transcribed PCR(RT-PCR) [e.g., a semi-quantitative RT-PCR, quantitative RT-PCR using e.g., the Light Cycler™ (Roche)], RNA in situ hybridization (RNA-ISH), in situ RT-PCR stain and oligonucleotide microarray analysis [e.g., using the Affymetrix microarray (Affymetrix®, Santa Clara, Calif.)] may be used.

According to a specific embodiment, real-time PCR is used for assaying secretion of a human beta-defensin from a cell.

Alternatively, the presence and/or level of the human beta-defensin amino acid sequence (i.e. human beta-defensin protein) can be determined using a human beta-defensin specific antibody via the formation of an immunocomplex [i.e., a complex formed between the human beta-defensin antigen (a human beta-defensin amino acid sequence) present in the biological sample and the human beta-defensin specific antibody] as, for example, by ELISA or by western blot analysis.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Development of an In-vitro Model Suitable for Evaluation of IL-13 Inhibition

Materials and Experimental Procedures
Culture of KU812 Cells
KU812 cells (human basophilic cells, ATCC CRL-2099™) were seeded into culture flasks using RPMI supplemented with 10% fetal bovine serum (FBS), and either 50 gentamicin and 50 amphotericin B or pen/strep. The seeded cells were incubated at 37±2° C. at 5±1% $CO_2$, with the culture media changed 2-3 times per week until a sufficient number of cells have grown.

Extracting Process (of Test Material)
Herbs were chosen according to quality inspection (differentiation and authentication of the raw materials, heavy metal analysis, pesticide residue check and active ingredient content analysis).
Sliced herbal material was homogenized with x10 volume of water, and extracted for 2 hours at 80° C. with stirring. The extraction was repeated three times using the same procedure, and the three extractions were mixed together. The homogenate was collected, filtered through a 400-mesh screen, concentrated (80° C., 0.1 MPa), and then centrifuged at 10000 r/min for 20 min.
The extracts were purified by macroporous resin and then concentrated to a volume as needed. Quality inspection for the extracts was assayed according to quality standard (natural character, relative density, pH value, heavy metal analysis, microbiological assay, active ingredient content determination).

Test Material Cytotoxicity Prescreen—MTS Assay
For use in the assay, the cells were seeded into 96-well plates (approximately 0.1 to $0.2 \times 10^6$ cells per well) in 100 µl of cell culture media without phenol red. Next, test material (1000 µl) prepared in cell culture media at 2× its final concentration was added to each well to bring the final volume of the culture to 200 µl. The plates were incubated for 24 hours at 37±2° C. and 5±1% $CO_2$. After the incubation, 20 µl of a 20:1 solution of MTS:PMS (Promega) were added to each well and the plates were returned to the incubator for an additional period of 4 hours. The plates were then read at 490 nm using a plate reader.

IL-13 Release Assay
Prior to use in the IL-13 release assay, the KU812 cells were cultured for two days in RPMI media without FBS. After this two-day incubation, RPMI with FBS was used for the IL-13 assay.
KU812 cells were seeded into 96-well plates (approximately 0.2 to $0.3 \times 10^6$ cells per well) in 100 µl of RPMI. Next, test material (100 µl) prepared in cell culture media at 2× its final concentration was added to each well, and the cells were incubated for approximately 6 hours at 37±2° C. and 5±1% $CO_2$. After this pretreatment period, 10 µl of a concentrated stock solution containing PMA and ionomycin were added to each well (20 ng/ml PMA and 1 µM ionomycin final concentration in the culture) and the plates were incubated overnight at 37±2° C. and 5±1% $CO_2$. The cell culture supernatant was then assayed for IL-13.

IL-13 ELISA (RayBiotech)
A series of standards were prepared (0-40 pg/ml) and 100 µl of each of these standards were dispensed into two wells (duplicates) in the 96-well plates. Subsequently, 25 µl of each cell culture supernatant sample and 100 µl of Diluent B were added to additional wells (the samples were diluted with Diluent B to bring their levels of IL-13 within the range of the standard curve) and the plates were incubated for two and a half hours at room temperature. After the incubation the plates were washed three times with wash buffer. Once the last wash was removed, 100 µl of a biotin-conjugated detection antibody were added. After incubating the plates for one hour at room temperature the plates were washed again as described above. HRP-streptavidin (100 µl) was then added to each well and the plates were incubated for 45 minutes at room temperature. Once the last wash was removed, 100 µl of substrate solution (hydrogen peroxide+tetramethylbenzidine as a chromagen) were added to each well. Once a sufficient level of color development occurred, 50 µl of stop solution (2N sulfuric acid) were added to each well and the plates were read at 460 nm.

Calculations
Cell Viability Assay (MTS Assay)
The mean absorbance of the wells not treated with test material was determined and used to represent 100% viability (Untreated). This value was then used to determine the viability of the wells treated with the test materials (Treated) using the following equation: ((Treated)/(Untreated))×100

IL-13 ELISA Analysis
For the IL-13 ELISA assay, the absorbance values for the known standards were used to generate a standard curve. The values for the unknown samples were then determined from this standard curve.

Results
Development of Cell-based Assay
A KU812 human basophilic culture model was used by the present inventors to assess the ability of the herbal extracts to exert an effect on IL-13 release. In the assay system used herein, KU812 cells were pretreated with the test materials for approximately 6 hours, and then with the test materials still present, the cells were stimulated with both phorbol myristate acetate (PMA) and the calcium ionophore ionomycin. After the addition of PMA and ionomycin, the cells were incubated overnight. On the following day the cell culture supernatant was assayed for IL-13 release.

Immune Cells as Model: KU812 Basophils
The cytokines IL-4 and IL-13 are produced by many cell types such as T cells, mast cells and basophils. Although it has long been thought that IL-4 is derived solely from CD4+ T cells, recent in vitro studies have clearly shown that human basophils account for most of the IL-4 and IL-13 generated in cultures by peripheral blood leukocytes [Higa S. et al., J Allergy Clin Immunol (2003) 111 (6): 1299-1306]. There is also increasing evidence for the role of basophils in the pathogenesis of atopic diseases such as bronchial asthma, atopic dermatitis and atopic rhinitis.

Basophils are a small population of peripheral blood leukocytes containing cytoplasmic granules that stain with basophilic dyes. Basophils and mast cells share several biochemical and functional properties, e.g., the expression of the high affinity receptor for IgE, and the capacity for release of histamine and other mediators upon activation. Mature basophils are typically found in the circulation, although they can be found in inflamed tissues. Mast cells, on the other hand, are found exclusively in the tissue.

The cross-linking of mast cells and basophils with specific antigens leads to the release of inflammatory mediators and cytokines such as IL-4, IL-13, and IL-5 that are key molecules related to IgE production, TH2 differentiation and allergic inflammation.

Relying on this information, the present inventors decided to work with KU812 cells, a human basophilic cell line established from a patient with basophilic leukemia in blast crisis.

KU812 Differentiation

KU812 cells are immature basophil precursor cells and also serve as a model for basophil differentiation. Differentiation of KU812 cells induces several changes, including increase of total histamine content, increased granulation, and expression of high-affinity receptors for IgE.

Different factors have been shown to differentiate the KU812 cell line into basophil-like cells [Nilsson G. et al., Immunology (1994) 81: 73-78; Fukuda T. et al., Blood (1987) 70: 612]. Several cytokines can induce its differentiation into basophil-like cells, including TNF-α, IL-6, IL-3, and IL-4. Differentiation was seen when KU812 cells were cultured with a combination of sodium butyrate and conditioned media from the human T-cell line Mo.3. Also, conditioned media from cultured peripheral blood mononuclear cells (PBMC) from atopic individuals induce differentiation of KU812 cells. The factor(s) in the conditioned media supernatant responsible for this effect has/have not yet been characterized. It has also been shown that KU812 cells may undergo differentiation in the absence of exogenous factors, under serum-free conditions.

The present inventors used KU812 human basophilic cells as a model cell type to find herbs that inhibit IL-13 expression. In their effort to calibrate an appropriate system for analysis, the present inventors discovered that after two days under serum-free conditions, KU812 cells expressed higher levels of IL-13, probably due to differentiation of the cells. The present inventors have therefore decided to use serum-free conditions before adding the stimulators and the herbal extracts.

Cytokines

Defensins (hBD) are produced by human skin keratinocytes upon injury or inflammation and are down-regulated by cytokines produced by mast cells, basophils and type-2 helper cells. It is well established that AD lesions are associated with increased expression of IL-4 and IL-13 [Albanesi C. et al., J. Immunol. (2007) 179(2): 984-992]. Cytokines suppress both hBD-2 and hBD-3 mRNA expression [Albanesi C. et al., supra]. Thus, IL-4 and IL-13 may account for the low expression of defensin in these lesions. In order to expand the understanding of defensin expression, the present inventors tested the inhibitory effects of the herb extracts on IL-4 and IL-13 expression levels in KU812 human basophilic cells.

Since the functions of IL-13 overlap considerably with those of IL-4, components that inhibit IL-13 usually also inhibit IL-4 expression. The present inventors therefore decided to test the inhibitory effect of the herb extracts on IL-4 expression using KU812 cells. Inventors measured very little expression of IL-4 following stimulation with PMA and Ionomycin (data not shown). A literature survey revealed that some signals employed by priming factors such as IL-3 favor the production of IL-13 rather than IL-4 [Higa et al., J Allergy Clin Immunol (2003) 111(6): 1299-1306]. Therefore, the present inventors continued by measuring only IL-13 expression.

Positive Controls

The present inventors chose to use two substrates as positive controls: Fisetin and Dexamethasone. Fisetin was previously shown to suppress the induction of IL-4, IL-13 and IL-5 mRNA expression by A23187-stimulated KU812 cells [Higa et al (2003), supra]. In the present results, the inhibition of fisetin was significant, however, the inhibition percentages were relatively low. Inventors therefore added dexamethasone as a positive control that exhibited high and significant inhibition percentages. Dexamethasone was previously shown to reduce inflammation and depress the immune system possibly by inhibition of IL-4 and IL-13 production by T cells and also by basophils [Shimizu et al., Clin Exp Allergy (1998) 28(4): 497-503].

Example 2

Screening Herbal Extracts for Stimulating Activity on Beta-Defensin Expression, Using Epidermal Cells (Keratinocytes: HaCaT Cells)

Materials and Experimental Procedures

Keratinocyte Cell Line (HaCaT)

The keratinocyte cell line was used. HaCaT cells were seeded into culture 75 T-flasks using DMEM (GIBCO) supplemented with 10% FBS (GIBCO) and antibiotics (GIBCO). The cells were incubated at 5% $CO_2$ and 37° C., with the culture media changed when confluence (% ratio of growth surface to plate surface) reached ~90%. To screen the extracts, extract (0.3 ml) was added to the supernatant of cultured HaCaT cells (~90 to 95% confluence) and the cells were incubated for 48 h.

Real-time PCR Analysis of Human Beta-Defensin 3 Expression

Total RNA Isolation

Total RNA was isolated with TRIZOL (Invitrogen Life Technologies) according to recommendations of the manufacturer. The RNA was precipitated with ethanol and re-suspended in diethyl pyrocarbonate H2O. The RNA from HaCaT cells was re-purified once to obtain RNA of adequate purity. The RNA concentration was determined by spectrophotometer and the total RNA obtained was converted to total cDNA only after the integrity of the RNA was confirmed by electrophoresis on an agarose gel.

Real-time PCR Analysis cDNA was synthesized from 200 ng purified RNA using iScript cDNA synthesis kit (Bio-Rad) according to the instructions of the manufacturer. Human beta-defensin 3 expression, together with GAPDH expression, was analyzed using AB Taqman MasterMix (Applied Biosystems, Part No.: 4369016, USA). The primers for human beta-defensin 3 and GAPDH were inventoried primers for Taqman Gene Expression Assays.

Figure 2:
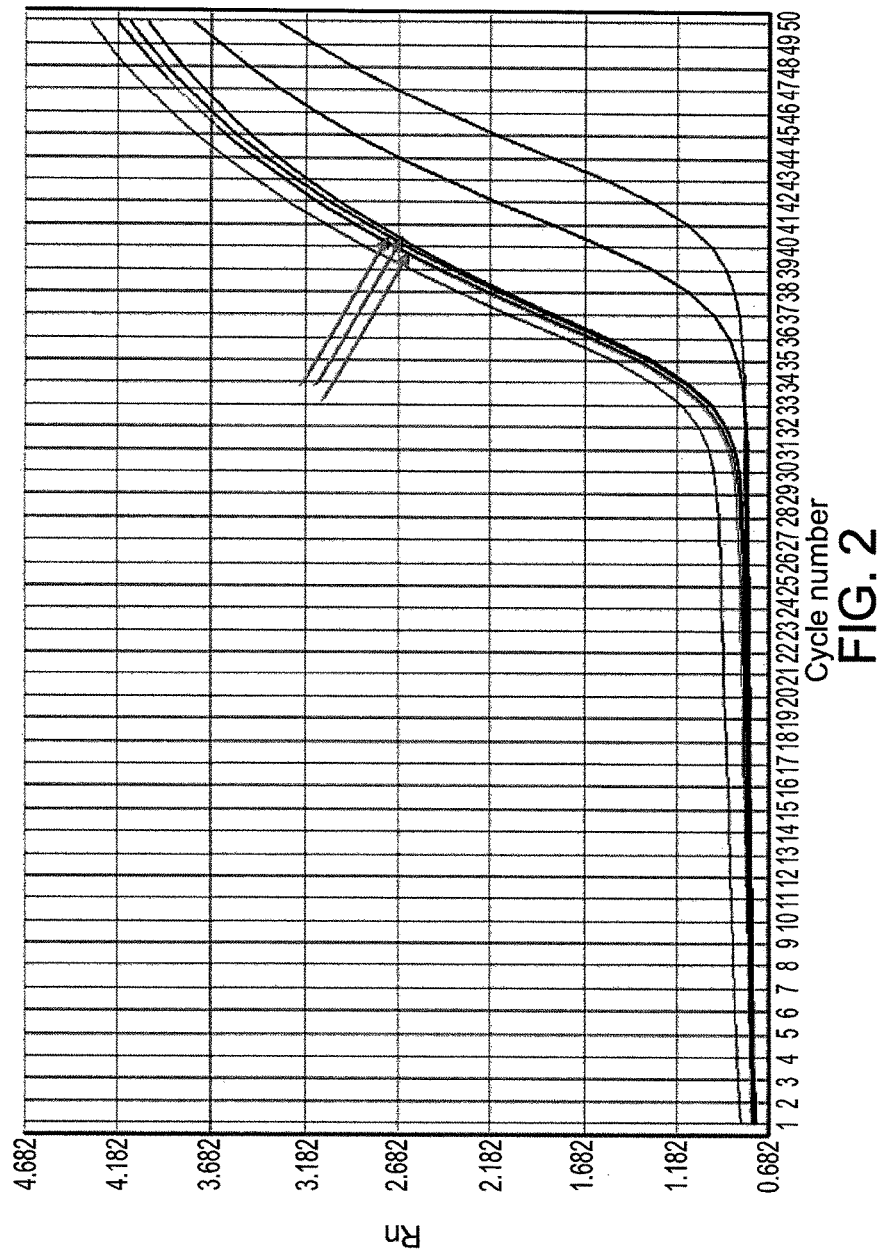
FIG. 2 is a line graph depicting real-time PCR analysis of human beta-defensin 3, using untreated HaCaT keratinocyte cells (n=3).
Figure 3A:
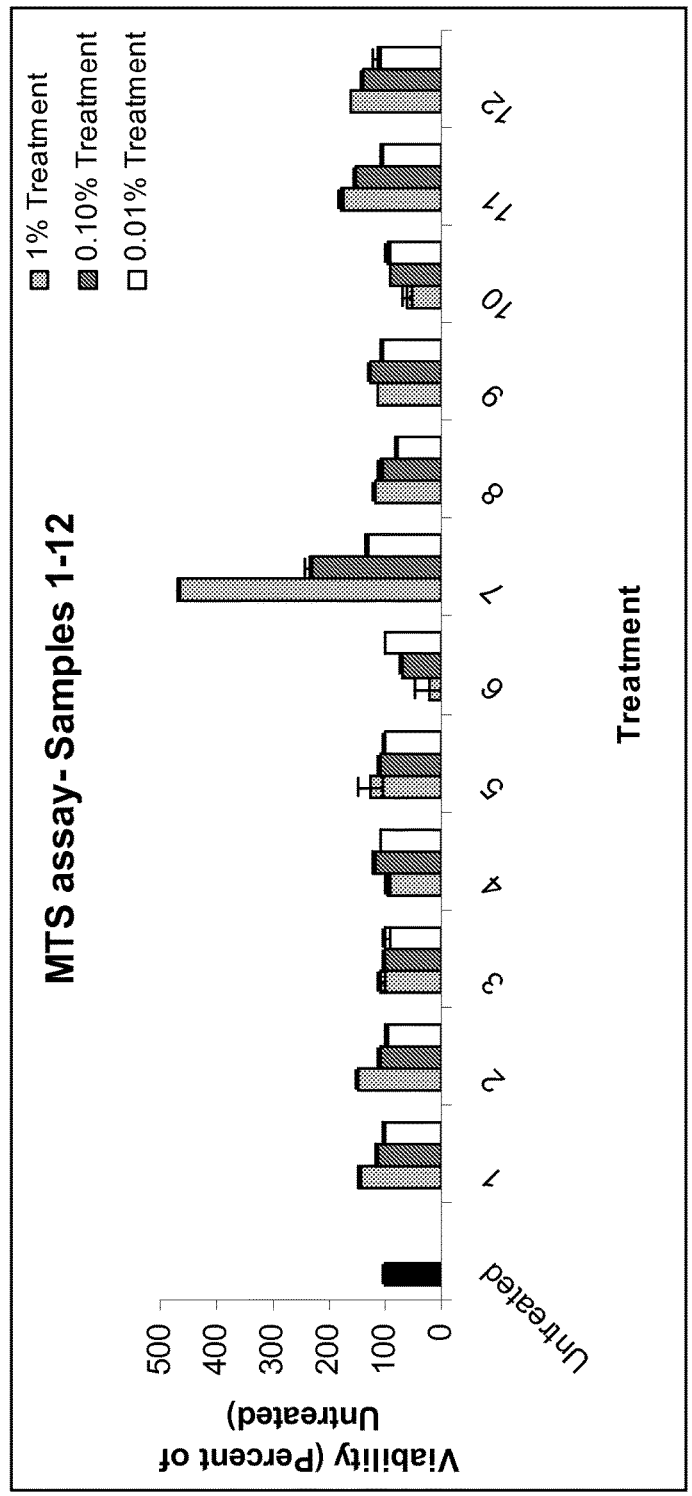
FIGS. 3A-D are graphs depicting percentages of cell viability as measured by MTS assay. KU812 cells were incubated with the herbal extracts (1%, 0.1% or 0.01% as indicated) for 24 h. Fisetin was measured at concentrations of 100, 10 and 1 µM. The plates were read at 490 nm and cell viability was calculated as a percentage of untreated cells (100% viability)±SD. Test material identification is as indicated in Table 1, below.
Figure 3B:
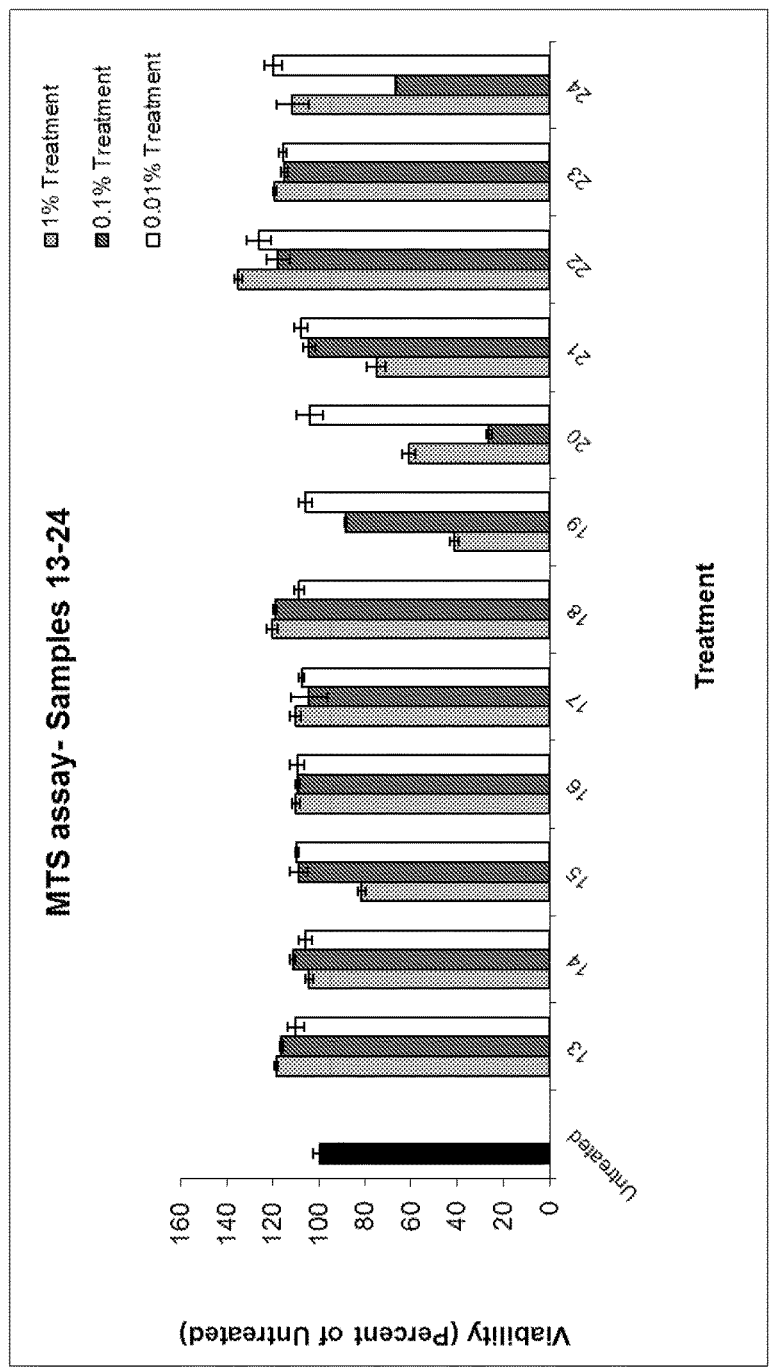
Figure 3C:
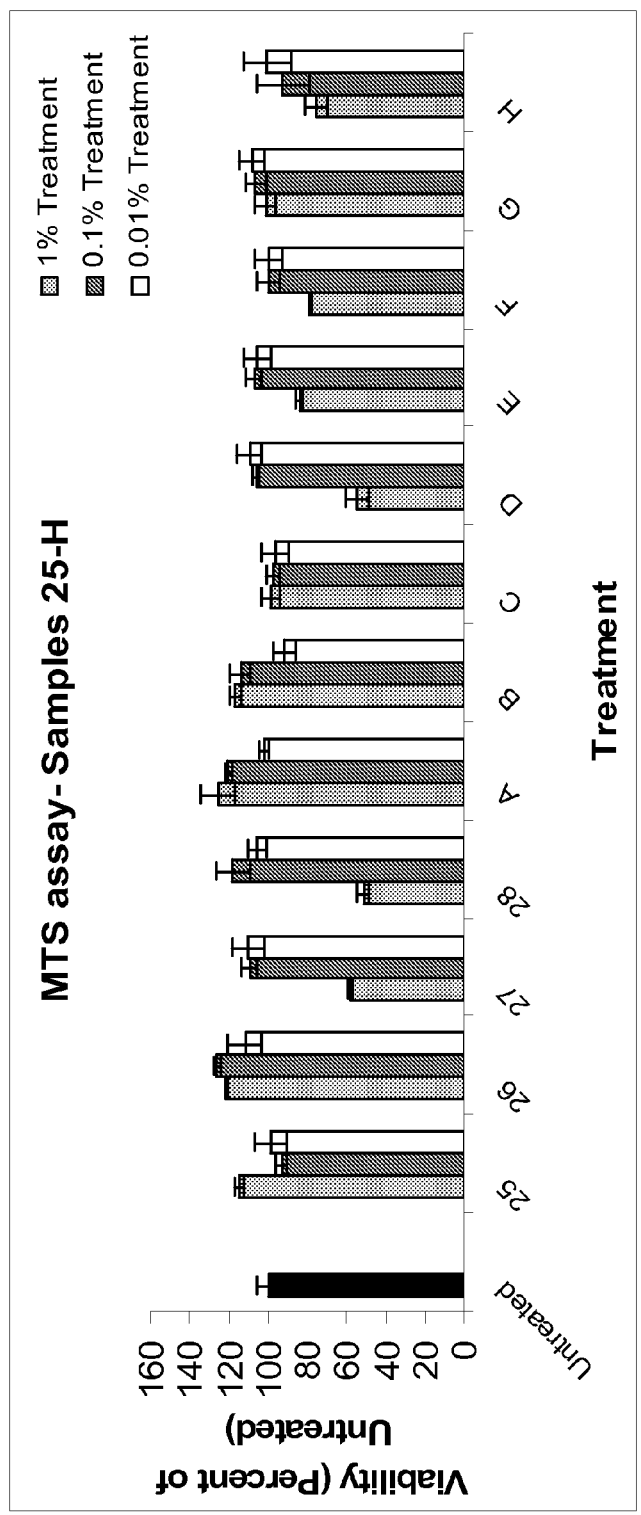
Figure 3D:
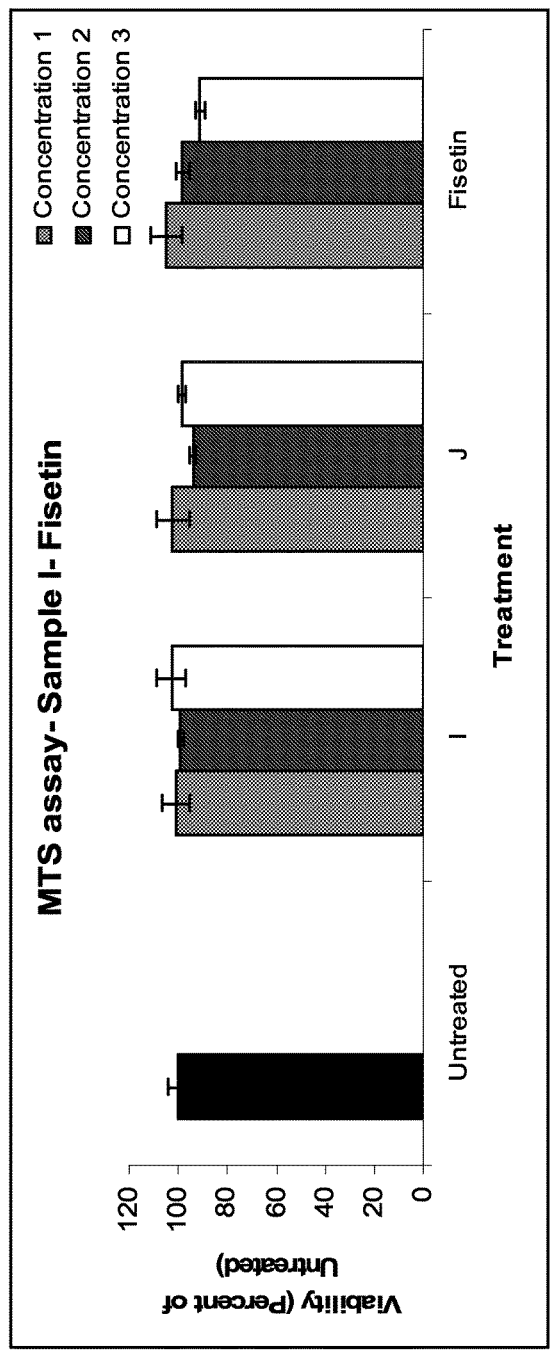
Figure 4A:
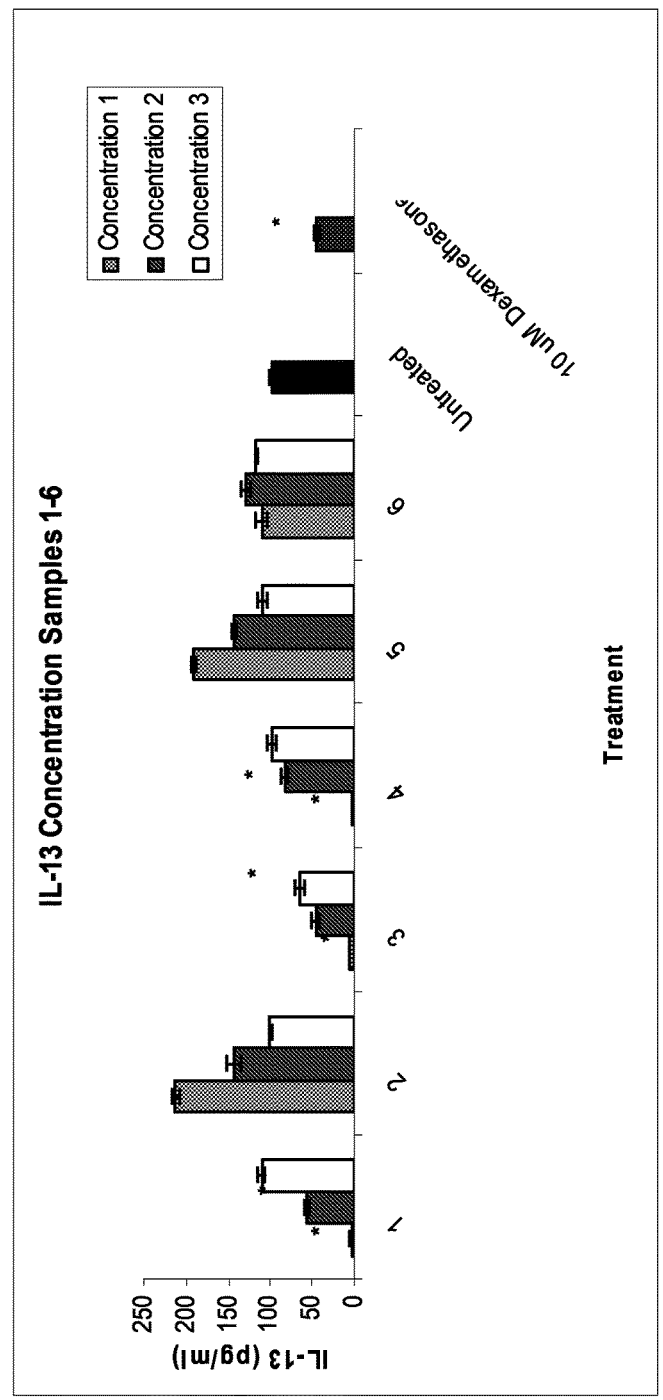
Figure 4C:
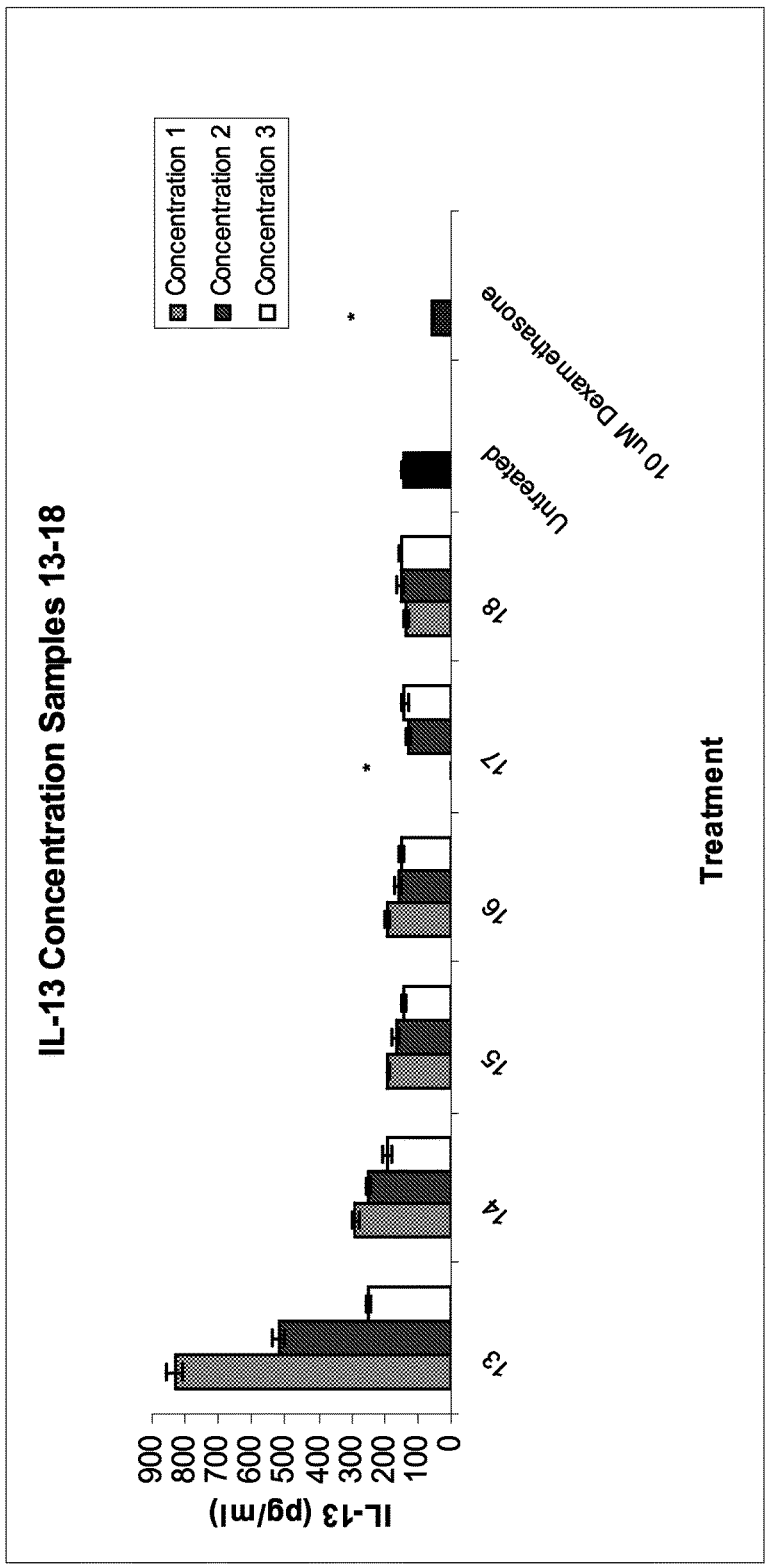
Figure 4D:
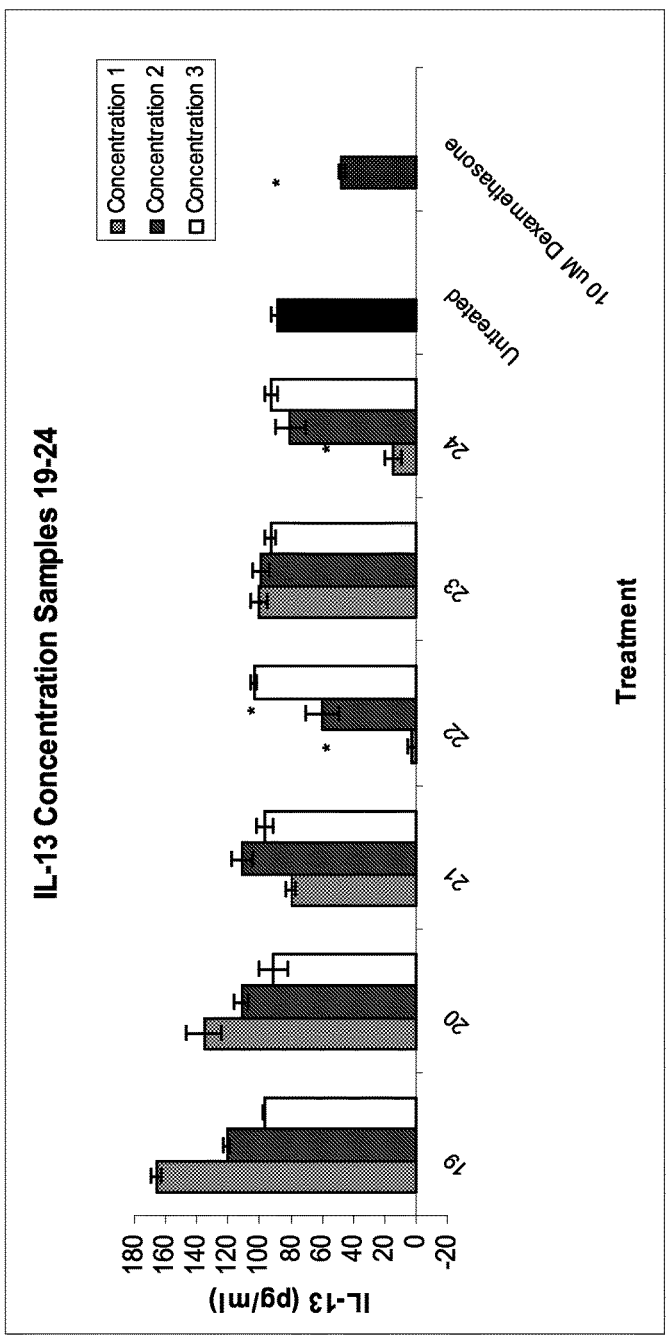
Figure 4E:
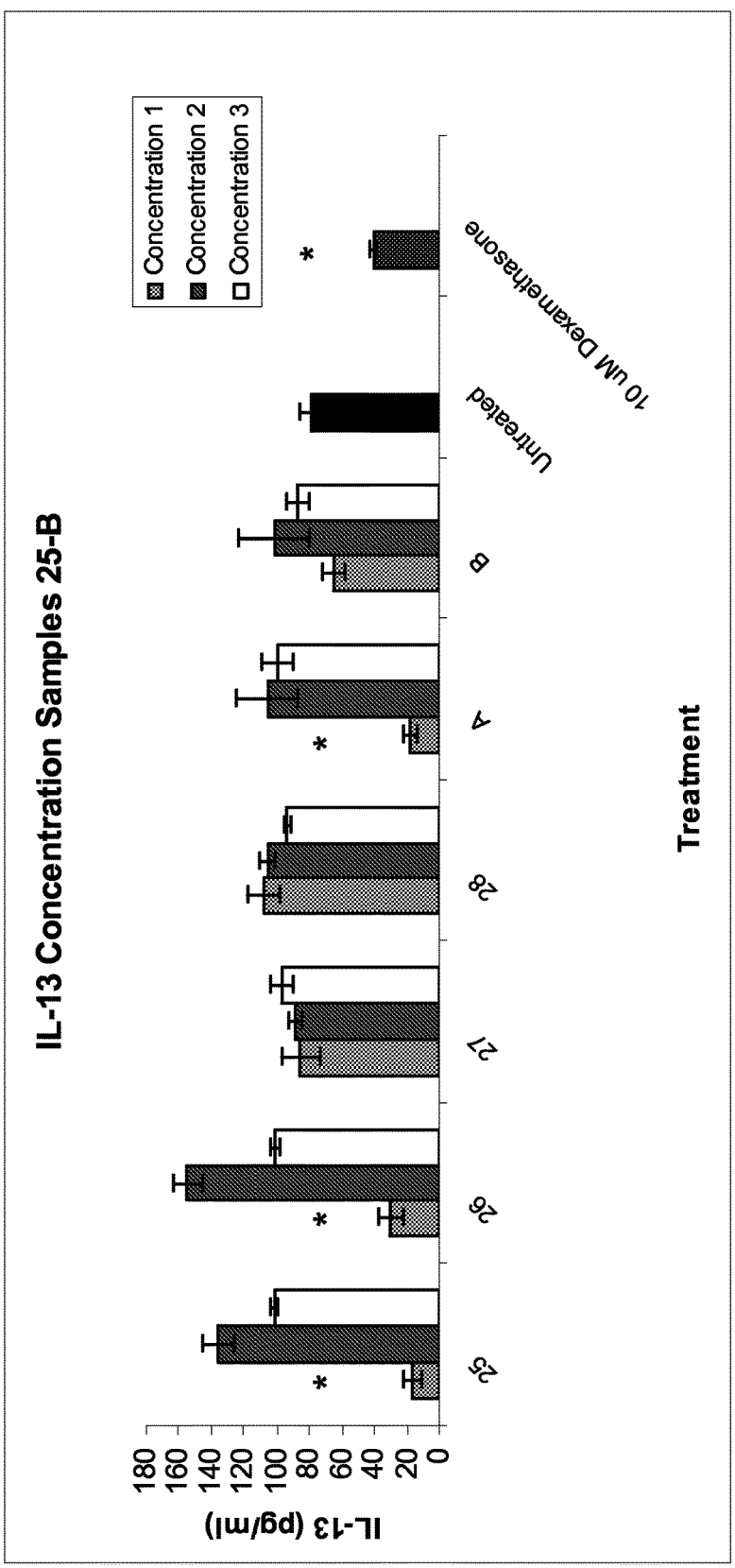
Figure 4G:
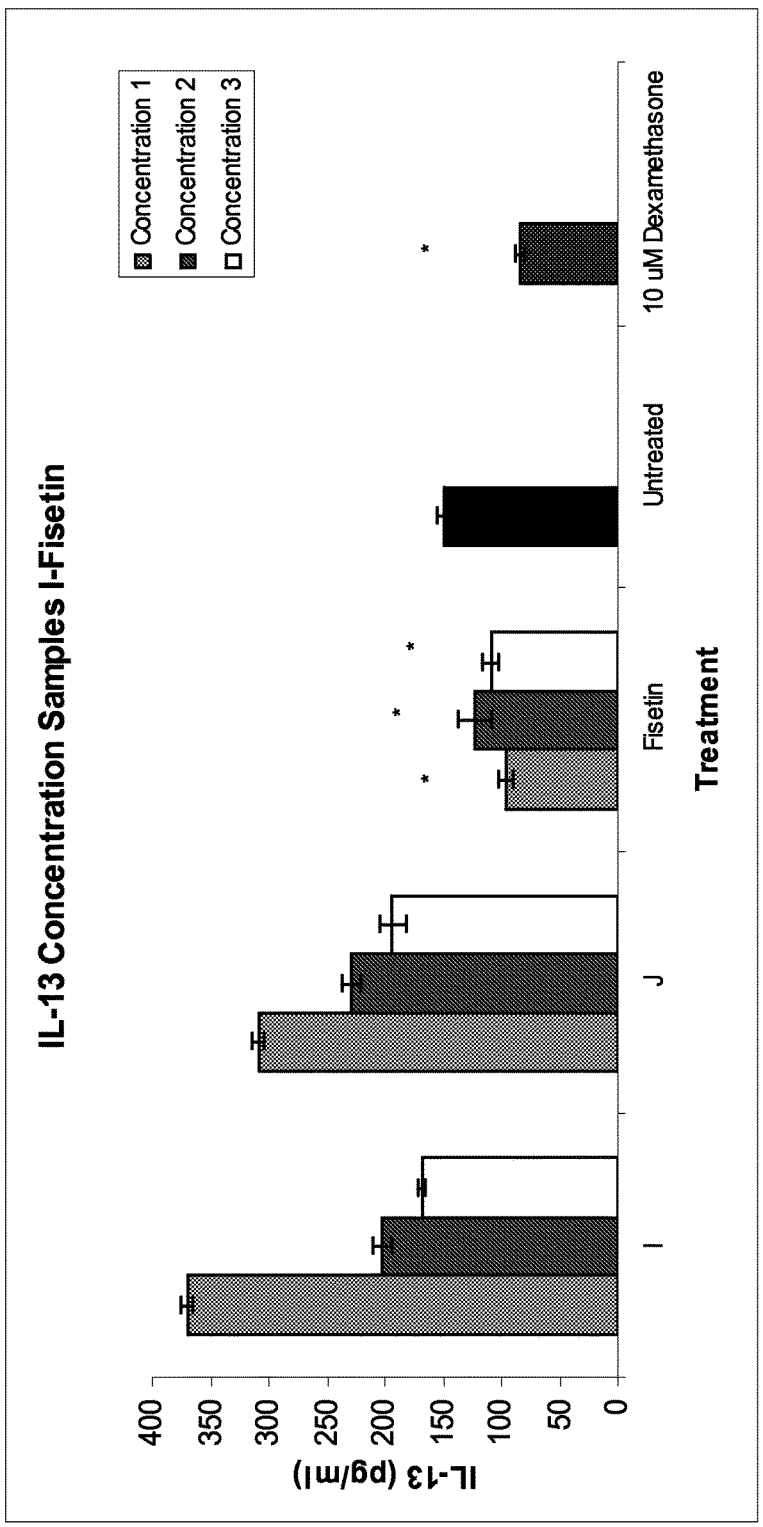
Figure 8:
FIG. 8 is a line graph depicting herbal extracts Nos. 232 and 246 which led to a significant increase in the expression of hBD-3.
Figure 9:
FIG. 9 is a line graph depicting herbal extract No. 362 which led to a significant increase in the expression of hBD-3.

Amplification was performed at 40 cycles (95° C., 30 s) followed by additional cycles (58° C., 30 s) in ABI Real-time PCR 7500 (Applied Biosystems). Data were analyzed by real-time PCR system software. The relative expression of each extract was calculated, adjusting for the real-time PCR of GAPDH expression (GAPDH normalization). The expression standards obtained 100-, 10-, and 1-fold diluted cDNA were confirmed in each real-time PCR experiment (see FIG. 1). The control test with untreated HaCaT cells showed this real-time PCR to be very sensitive and reliable using HaCaT cells (see FIG. 2).

Extracting Process

Herbs were chosen according to quality inspection (differentiation and authentication of the raw materials, heavy metal analysis, pesticide residue check and active ingredient content analysis).

Sliced herbal material was homogenized with x10 volume of water, and extracted for 2 hours at 80° C. with stirring. The extraction was repeated three times using the same procedure, and the three extractions were mixed together. The homogenate was collected, filtered through a 400-mesh screen, concentrated (80° C., 0.1 MPa), and then centrifuged at 10000 r/min for 20 min.

The extracts were purified by macroporous resin and then concentrated to a volume as needed. Quality inspection for the extracts was assayed according to quality standard (natural character, relative density, pH value, heavy metal analysis, microbiological assay, active ingredient content determination).

Results

Stimulation of human beta-defensins was examined by the present invention, this was based on previous scientific reports which showed that human beta-defensins, especially isoforms 2 and 3, serve as important antimicrobial barriers in human skin. Reduced expression of human beta-defensins in the skin of patients with atopic dermatitis causes the abnormal colonization of atopic dermatitis-related microorganisms such as *Staphylococcus aureus*. Although reduced expression of both isoforms is related to atopic dermatitis, several recent scientific reports have shown that human beta-defensin isoform 3 plays a major role in the pathology of atopic dermatitis. Human beta-defensin isoform 3 shows a broad spectrum of anti-microbial activity and has strong activity at physiological concentrations against *S. aureus* by itself [Harder et al., Nature (1997) 387: 861; Harder et al., J Biol Chem (2001) 276: 5707-13], while hBD-2 requires the presence of LL-37 to kill *S. aureus* [Xuejun Chenba et al., J. Dermatol. Science (2005) 40(2), 123-132].

Example 3

Screening Herbal Extracts for IL-13 Inhibition, Using KU812 Basophilic Cells

Materials and Experimental Procedures
See Example 1, hereinabove.
Results
MTS Results Different herbal extracts (see Table 1, below) were used to establish a range of safe concentrations for the test materials to use in the IL-13 inhibition assay. The results of the MTS assays performed are presented in FIGS. 3A-D. Values represent percentages of viability relative to the control (Untreated). These results were used to establish a range of safe concentrations for the test materials used in the IL-13 inhibition assay. Test material identification is as depicted in Table 1.

TABLE 1

Test material identification and analysis

| Test material identification | Herb name | pH value | Residue after evaporation (%) | Total microbial count |
|---|---|---|---|---|
| 1 | *Glycyrrhiza glabra* (Licorice) | 4.08 | 13.7 | 0 |
| 2 | *Saposhnikovia divaricata* | 3.29 | 24.4 | 0 |
| 3 | *Radix Tripterygii wilfordii* | 3.51 | 4.4 | 0 |
| 4 | *Cimicifuga racemosa* | 3.59 | 8 | 0 |
| 5 | *Celosia argentea* | 4.79 | 2.4 | 0 |
| 6 | Coptis Root | 3.27 | 13.3 | 0 |
| 7 | *Radix Salviae miltiorrhizae* | 3.31 | 31.2 | 0 |
| 8 | *Saururus Chinensis* (Leaves) | 2.42 | 17.2 | 0 |
| 9 | *Calendula officinalis* | 2.97 | 14.1 | 0 |
| 10 | Gentiana | 2.36 | 9 | 0 |
| 11 | *Mentha aquatica* L | 3.33 | 7.9 | 0 |
| 12 | Dandelion Root/*Taraxacum officinale* | 3.31 | 12.1 | 0 |
| 13 | Broom Cypress Fruit | 4.02 | 7.6 | 0 |
| 14 | *Anemarrhena asphodeloides* | 2.57 | 21.6 | 0 |
| 15 | *Stellaria dichotoma* L. var. *lanceolata*. Root | 3.63 | 25.5 | 0 |
| 16 | *Fritillaria verticillata* | 3.68 | 6.1 | 0 |
| 17 | *Silybum marianum* | 3.25 | 5.6 | 0 |
| 18 | *Actinidia polygama* | 4.02 | 16.7 | 0 |
| 19 | *Phellodendron-* Water Extract | 5.06 | 16.34 | 0 |
| 20 | *Sapindus mukurossi-* Water Extract | 5.16 | 24.9 | 0 |
| 21 | *Radix Sophora flarescents-* Water extract | 4.15 | 22.35 | 0 |
| 22 | *Sanguisorba officinalis* (DiYu)- Water extract | 4.02 | 21.28 | 0 |
| 23 | *Fructus Cnidium* | 3.86 | 10.76 | 0 |
| 24 | *Camelia japonica* | 2.94 | 25.3 | 0 |
| 25 | *Scutellaria baicalensis-* Water extract | 3.54 | 23.24 | 0 |
| 26 | *Rheum palmatum-* Water Extract | 4.68 | 21.23 | 0 |
| 27 | *Chrysanthemum-* Water Extract | 3.96 | 22.49 | 0 |
| 28 | *Portulaca-* Water Extract | 4.87 | 26.75 | 0 |
| A | Peony Bark | 2.78 | 17.9 | 0 |
| B | *Angelica sinensis* | 3.06 | 29.1 | 0 |
| C | *Astragalus membranaceus* Root | 3.06 | 22.2 | 0 |
| D | *Evodia rutaecarpa* fruit | 3.14 | 12.4 | 0 |
| E | *Polygonum cuspidatum* | 2.94 | 12.8 | 0 |
| F | *Liriope platyphylla* | 2.9 | 23.6 | 0 |
| G | *Smilax glabra rhizoma* | 2.71 | 6.9 | 0 |
| H | *Curcuma longa* | 4.17 | 5.9 | 0 |
| I | *Indigo naturalis* | 9.23 | 0.1 | 0 |
| J | *Semen Hydnocarpi hainanensi* | 4.14 | 2.7 | 0 |

IL-13 Inhibition Results

The test material concentrations tested were determined according to the MTS results (presented above). The results of the IL-13 inhibition assays performed are presented in FIGS. 4A-G and are summarized in Table 2, below, and show that several herbal extracts significantly reduce the amount of IL-13 release, including for example, *Glycyrrhiza glabra*, *Cimicifuga racemosa* and *Silybum marianum*. Dexamethasone was used as a positive control at a concentration of 10 μM.

Summary

The present inventors tested the inhibitory effect of different herbal extracts on IL-4 expression using KU812 cells. The purpose of this study was to determine if the test materials could inhibit IL-13 release from KU812 cells stimulated with PMA and ionomycin. Several herbal extracts were observed to significantly reduce the amount of IL-13 release, including for example, *Glycyrrhiza glabra*,

*Cimicifuga racemosa* and *Silybum marianum*. The percentage of IL-13 inhibition by the herbal extracts is presented in Table 2, below.

TABLE 2

Percentages of IL-13 inhibition by the herbal extracts in KU812 cells

| Herb name | No. | 1% | 0.01% | 0.001% |
|---|---|---|---|---|
| Glycyrrhiza glabra | 1 | 97.67% | 43.22% | — |
| Tripterygii wilfordii | 3 | 93.9% | 53.34% | 33.2% |
| Cimicifuga racemosa | 4 | 96.76% | 16.09% | 0.3% |
| Salviae miltiorrhizae | 7 | 76.58% | — | — |
| Silybum marianum | 17 | 98.65% | 10.8% | 1.2% |
| Sanguisorba officinalis | 22 | 97.5% | 31.9% | — |
| Camelia japonica | 24 | 84.2% | 8.85% | — |
| Scutellaria baicalensis | 25 | 79% | — | — |
| Rheum palmatum | 26 | 62.26% | — | — |
| Peonia suffruticasa | A | 76.98% | — | — |
| Angelica sinensis* | B | 18.74% | — | — |
| Polygonum cuspidatum | E | 18.74% (concentration 0.5%) | — | — |
| Fistein** | | 35.69% | 17.3% | 26.52% |
| Dexamethasone | 10 µM | 52% | | |

*Slight reductions (not significant)
**Fistein was measured at concentrations of 100 µM, 10 µM and 1 µM Example 4

Screening Herbal Extracts for Stimulation of Human Beta-Defensin 3

Materials and Experimental Procedures
See Example 2, hereinabove.
Results
400 herbal extract were tested in the present study. Of these only six herbal extracts showed remarkable stimulating effect on human beta-defensin-3 (hBD-3) when considering its direct effect before or after GAPDH normalization. Thus, although almost all tested herbal extracts showed no significant effect on hBD-3 expression, six herbal extracts showed stimulating effects when measured at a concentration of 0.33%, as shown in FIGS. 5-9.

Figure 10:
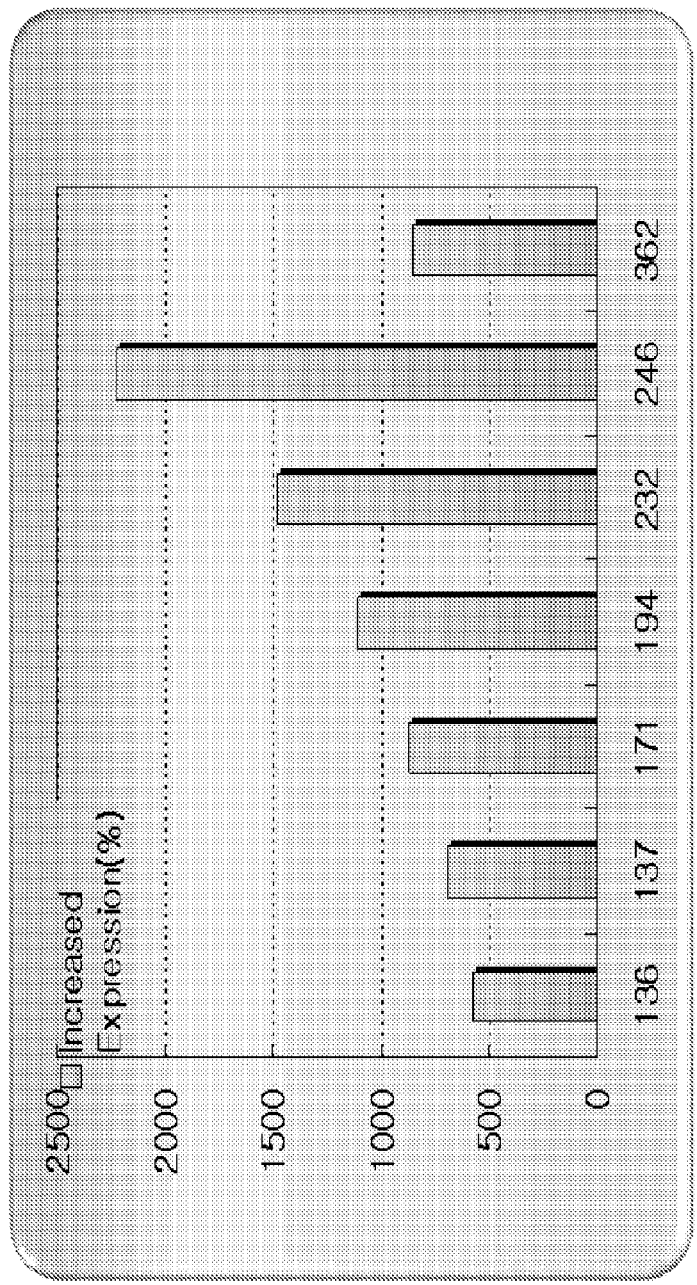
FIG. 10 is a bar graph depicting the stimulating effect of six herbal extracts (as indicated) on hBD-3 expression.

Herbal extracts Nos. 136 and 137 showed stimulation percentages of 573±48% and 693±182%, respectively, as shown in FIG. 5. Interestingly, No. 136 is *Rubi fructus*, which grows in China, and No. 137 is *Rubi fructus*, which grows in Korea. The herbal extracts that exhibited stimulation effect of hBD-3 are: *Lysimachiae foenumgraeci herba, Ailanthi radicis cortex, Galla rhois, Peucedani radix*, and *Albizziae cortex* (Nos. 171, 194, 232, 246, and 362, respectively). The summarized stimulating effect and statistical values of these six herbal extracts on hBD-3 is listed in Table 3, below, and in FIG. 10 (the six herbal extracts identified were tested three times and the statistical mean values were calculated).

TABLE 3

Summarized stimulating effect of six herbal extracts on hBD-3 expression

| No. | Herb name | 1th Test (%) | 2th Test (%) | 3th Test (%) | Mean ± SD | Viability |
|---|---|---|---|---|---|---|
| 136(*) | Rubi fructus | 524 | 575 | 619 | 573 ± 48 | down |
| 137(*) | Rubi fructus | 900 | 559 | 619 | 693 ± 182 | — |

TABLE 3-continued

Summarized stimulating effect of six herbal extracts on hBD-3 expression

| No. | Herb name | 1th Test (%) | 2th Test (%) | 3th Test (%) | Mean ± SD | Viability |
|---|---|---|---|---|---|---|
| 171 | Lysimachiae foenumgraeci herba | 831 | 702 | 1082 | 872 ± 193 | — |
| 194 | Ailanthi radicis cortex | 868 | 1042 | 1420 | 1110 ± 282 | down |
| 232 | Galla rhois | 1744 | 1203 | 1502 | 1483 ± 271 | down |
| 246 | Peucedani radix | 2912 | 1859 | 1903 | 2225 ± 596 | down |
| 362 | Albizziae cortex | 853 | 933 | 792 | 859 ± 71 | — |

(*)Nos. 136 and 137 are the same plants grow in China and Korea, respectively.

Example 5

Extraction Processes Optimization of the Identified Herbal Extracts

Figure 11:
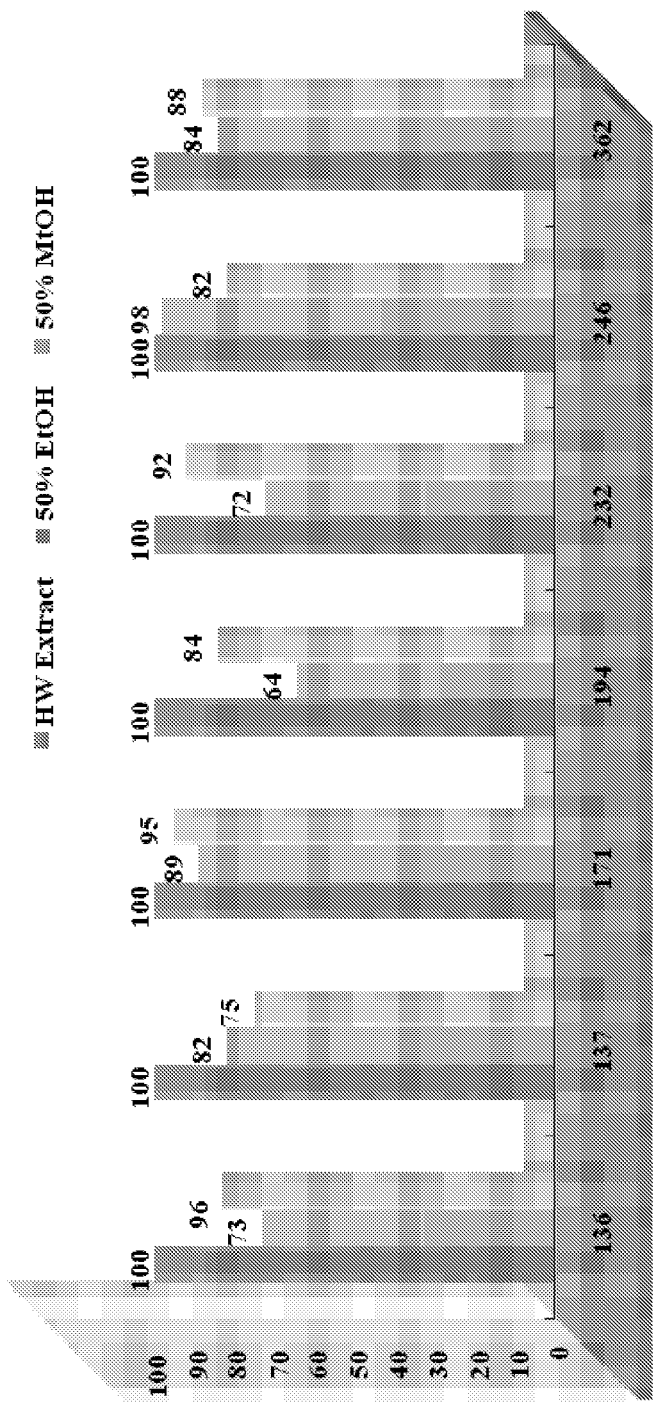
FIG. 11 is a bar graph depicting the comparison of hBD-3 stimulation by herbs (as indicated) extracted with hot water (HW), 50% EtOH and 50% MtOH.

Materials and Experimental Procedures
Extraction of Active Ingredients from Herbal Extracts
To test the effects of solvents commonly used for extraction, the present inventors extracted the indicated herbal sources in hot water, in 50% EtOH, or in 50% MtOH.
Results
Comparison of Different Extraction Solvents for hBD-3 Stimulation
To identify more effective ways to extract the active ingredients from the identified herbal extracts, the present inventors compared hBD-3 stimulation by the selected herbs using three different extraction solvents: 50% EtOH, 50% MtOH, and 100% distilled water. Stimulation was calculated by normalization of the values from the control groups of each solvent. As shown in FIG. 11, human beta-defensin 3 stimulation by herbal extracts Nos. 136, 137, 171, 194, 232, 246 and 362 was highest using hot water extracts. Other solvents (50% of EtOH and MtOH) showed relatively high activities, but lower (65% to 95%) than water extraction.

Example 6

Screening Herbal Extracts Having Stimulating Activity on Beta-Defensin Expression for their Activity as IL-13 Inhibitors, Using KU812 Basophilic Cells Materials and Experimental Procedures
See Example 1, hereinabove.
Results
Following the primary in-vitro studies the present inventors found 10 herbal extracts that inhibited IL-13 expression (as measured by ELISA) and 6 herbal extracts that stimulated beta-defensin 3 expression (as measured by RT-PCR).
Next, the present inventors had chosen the herbal extracts that exhibited the most significant activities in both categories. Herbal extracts that may exhibit toxicity (such as *Radix Tripterygii Wilfordii*) or herbal extracts that are not known for human application and have no INCI names were eliminated (such as *Terminariae Fructus*) although they had exhibited significant activities.
To choose the final herbal mixture, the present inventors tested the activity of herbal extracts that exhibited IL-13 inhibition for their ability to stimulate beta-defensin and herbal extracts that exhibited defensin stimulation for their ability to inhibit IL-13 release. Inventors also measured synergistic effect between herbal extracts in both assays (ELISA and RT-PCR). Seven herbal extracts were chosen (as described in Table 4, below).

TABLE 4

Herbal extracts

| Herbal extracts that exhibited IL-13 inhibition | Herbal extracts that exhibited beta-defensin stimulation |
|---|---|
| *Glycyrrhiza glabra* (Licorice) Root Extract | *Ailanthus altissima* extract |
| *Cimicifuga raceomosa* (Black cohosh) | *Galla rhois gallnut* Extract (*Galla chinensis*) |
| *Silybum marianum* | *Peucedanum praeruptorum* (*Peucedanti Radix*) |
| *Sanguisorbae officinalis* (*Radix Sanguisorbee*) | |

MTS Results

Figure 12:
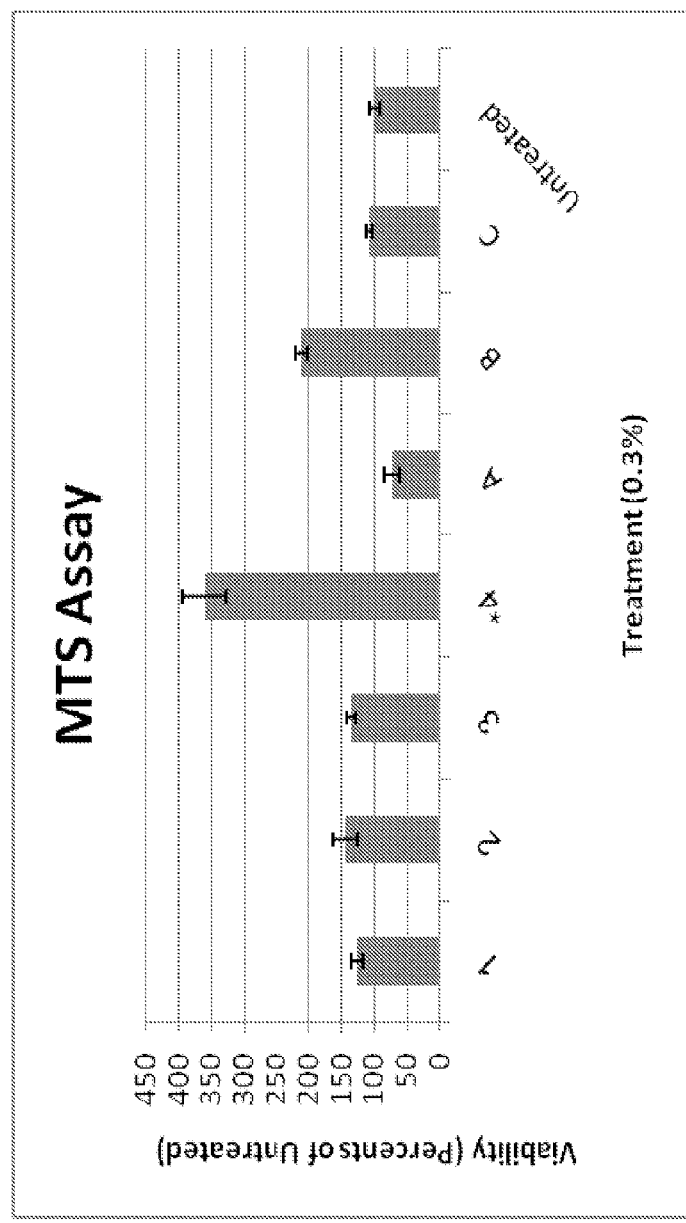
FIG. 12 is a bar graph depicting the percentages of cell viability as measured by MTS assay. KU812 cells were incubated with the herbal extracts (0.3%) for 24 h. The plates were read at 490 nm and cell viability was calculated as a percentage of untreated cells (100% viability)±SD. Of note, samples 4 and B—the test material may have reacted with the MTS solution. Microscopic examination did not show any signs of excessive cell proliferation or cytotoxicity. The test material identification is as follows: 1. *Glycyrrhiza glabra;* 2. *Cimicifuga raceomosa;* 3. *Silybum marianum;* 4. *Sanguisorbae officinalis;* A. *Ailanthus altissima;* B. *Galla rhois gallnut;* C. *Peucedanum praeruptorum*.

Herbal extracts that exhibited beta-defensin stimulation activity in the primary in-vitro study (see Example 4 and Table 4, above) were measured for cell viability in MTS assay, to evaluate safe concentration for the test materials to use in the IL-13 inhibition assay. The results of the MTS assay performed are presented in FIG. 12. Values represent percentages of viability relative to the control (Untreated).

IL-13 Inhibition Results

Figure 13:
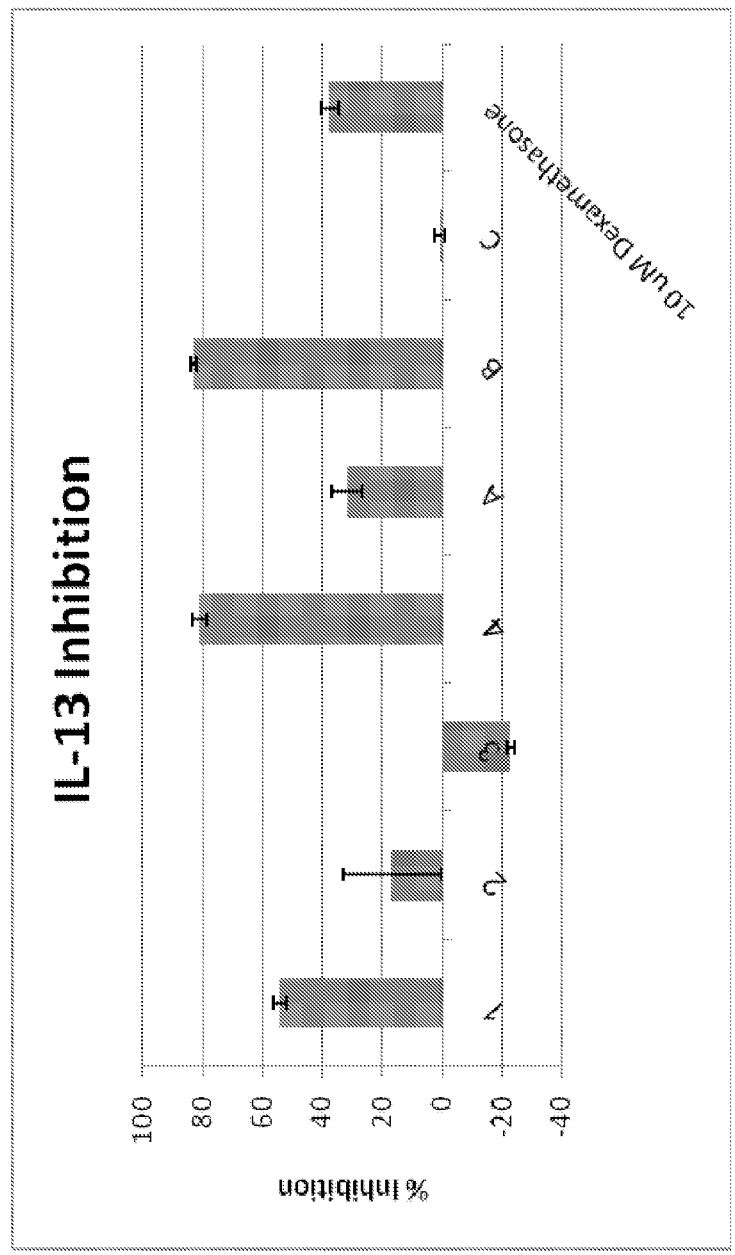
FIG. 13 is a bar graph depicting inhibition of IL-13 expression by herbal extracts in KU812 cells. KU812 cells were treated with the herbal extracts (0.3%) as described in Example 1, hereinbelow, and the cell culture supernatants were then assayed for IL-13 release. Values are presented as mean IL-13 concentration (pg/ml)±SD. The test material identification is as follows: 1. *Glycyrrhiza glabra;* 2. *Cimicifuga raceomosa;* 3. *Silybum marianum;* 4. *Sanguisorbae officinalis;* A. *Ailanthus altissima;* B. *Galla rhois gallnut;* C. *Peucedanum praeruptorum*.
Figure 14E:
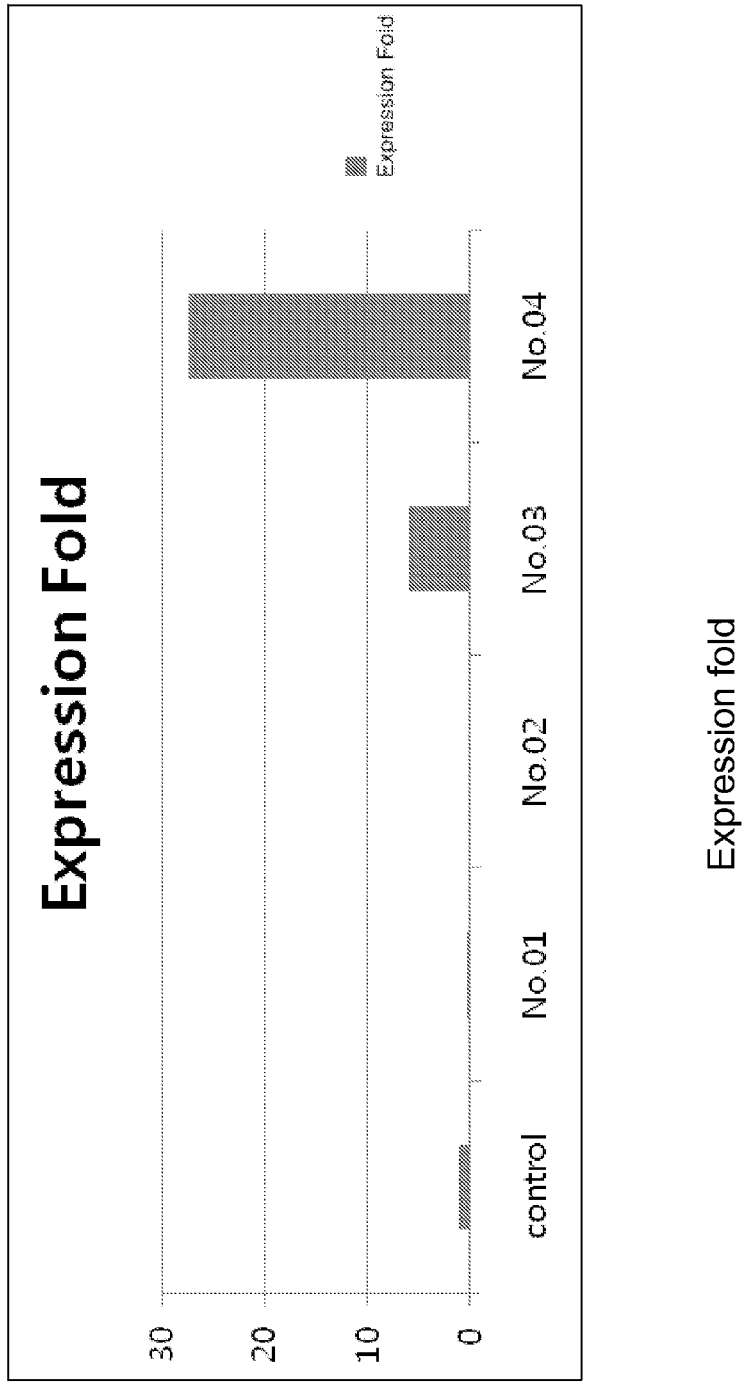

Herbal extracts that exhibited beta-defensin stimulation activity in the primary in-vitro study (see Example 4 and Table 4, above) were measured for their ability to inhibit IL-13 release. The results for the IL-13 inhibition assay performed are presented in FIG. 13 and show that both *Ailanthus altissima* and *Galla rhois gallnut* exhibit IL-13 inhibitory activity. The concentration of the test materials tested was respectively to MTS results (0.3%). Dexamethasone was used as a positive control at a concentration of 10 µM.

Summary

The purpose of this study was to determine if the test materials that were found to stimulate beta-defensin expression in keratinocyte cells could also inhibit IL-13 release from KU812 cells stimulated with PMA and ionomycin. The herbal extracts *Ailanthus altissima* and *Galla rhois gallnut* exhibited significant IL-13 inhibition activity.

Among the herbal extracts that exhibited IL-13 inhibition in the first study, *Glycyrrhiza glabra* (Licorice) and *Sanguisorbae officinalis* exhibited the most significant inhibition also in this assay.

Example 7

Screening Herbal Extracts Having Inhibitory Effect on IL-13 for their Activity as Human Beta-Defensin 3 Stimulators Materials and Experimental Procedures
See Example 2, hereinabove.
Results Among the four herbal extracts that exhibited significant IL-13 inhibition in the first study (see Example 3, above), two extracts had also shown stimulating effect on human beta-defensin-3 (hBD-3) when considering their direct effect before and after GAPDH normalization (measured by RT-PCR), namely *Silybum marianum* and *Sanguisorbae offici-*

*nalis*. *Glycyrrhiza glabra* (Licorice) and *Cimicifuga raceomosa* extracts didn't show any significant effect. *Sanguisorbae officinalis* extract exhibited the most significant stimulation effect on beta-defensin stimulation (FIGS. 14A-D). The values are summarized in FIG. 14E and in Table 5, below. 3.

TABLE 5

The effect of herbal extracts on hBD3
(after GAPDH normalization)

| | Test sample | | | | |
|---|---|---|---|---|---|
| | control | No. 1 | No. 2 | No. 3 | No. 4 |
| Expression fold | 1 | 0.072685 | 0 | 5.867937 | 27.43561 |

The test material identification is as follows: 1. *Glycyrrhiza glabra*; 2. *Cimicifuga raceomosa*; 3. *Silybum marianum*; 4. *Sanguisorbae officinalis*.

Summary

The purpose of this study was to determine if the test materials that were found to inhibit IL-13 release in the first study (see Example 3, above) could also stimulate beta-defensin 3 expression from keratinocytes (HaCaT cells). In the first study (see Example 3, above), four herbal extracts were shown to significantly reduce the amount of IL-13 release. Among them, *Silybum marianum* also displayed stimulation effect on beta-defensin 3 (5.87 fold) and *Sanguisorbae officinalis* exhibited the most significant stimulatory effect (27.4 fold) on beta-defensin 3.

Example 8

Synergism Between Herbal Extracts

Materials and Experimental Procedures
See Examples 1 and 2, hereinabove.
Results Synergistic effect between herbal extracts was measured by ELISA for IL-13 inhibition activity and by RT-PCR for defensin-3 stimulation activity.

Figure 15A:
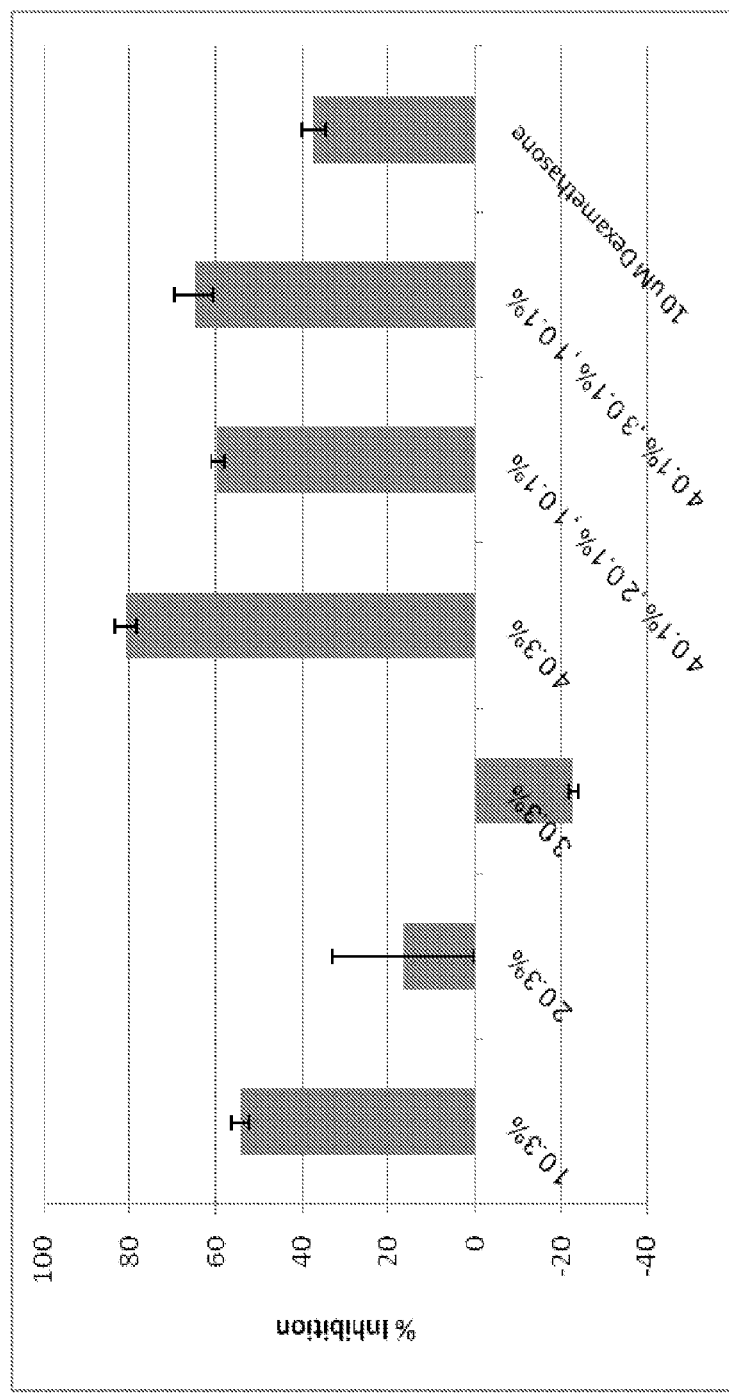
FIGS. 15A-C are bar graphs depicting the synergistic effect between herbal extracts. Herbal extracts were measured for synergistic effect on IL-13 inhibition (KU812 cells, ELISA) (FIG. 15A) or for beta-defensin 3 stimulatory effect (HaCaT cells, RT-PCR) (FIGS. 15B-C). 4 herbal extracts were measured for synergistic effect with 1% *Ailanthi radicis* cortex (FIG. 15B) or with (1%) *Galla Rhois* (FIG. 15C).

Reduction in IL-13 release was observed with the following herb combinations: 1+2+4 (1. *Glycyrrhiza glabra*; 2. *Cimicifuga raceomosa*; 4. *Sanguisorbae officinalis*) and 1+3+4 (1. *Glycyrrhiza glabra*; 3. *Silybum marianum*; 4. *Sanguisorbae officinalis*) —when the test materials present were at a total concentration of 0.3%. However, when compared to the inhibition of each herbal extract alone, no significant synergistic effect was demonstrated (FIG. 15A). When the concentrations of the test materials were reduced to 0.01% (either alone or in combination with one another), a significant reduction in IL-13 release was not observed (data not shown).

Figure 15B:
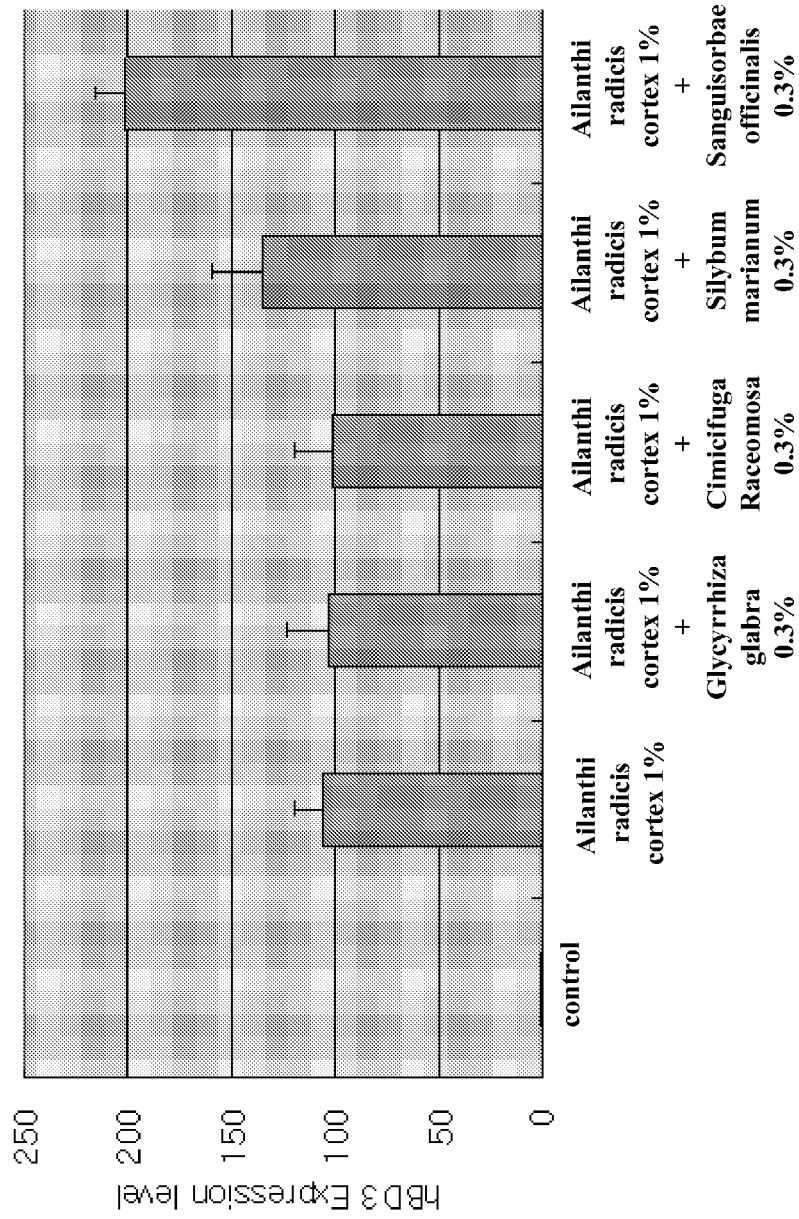
Figure 15C:
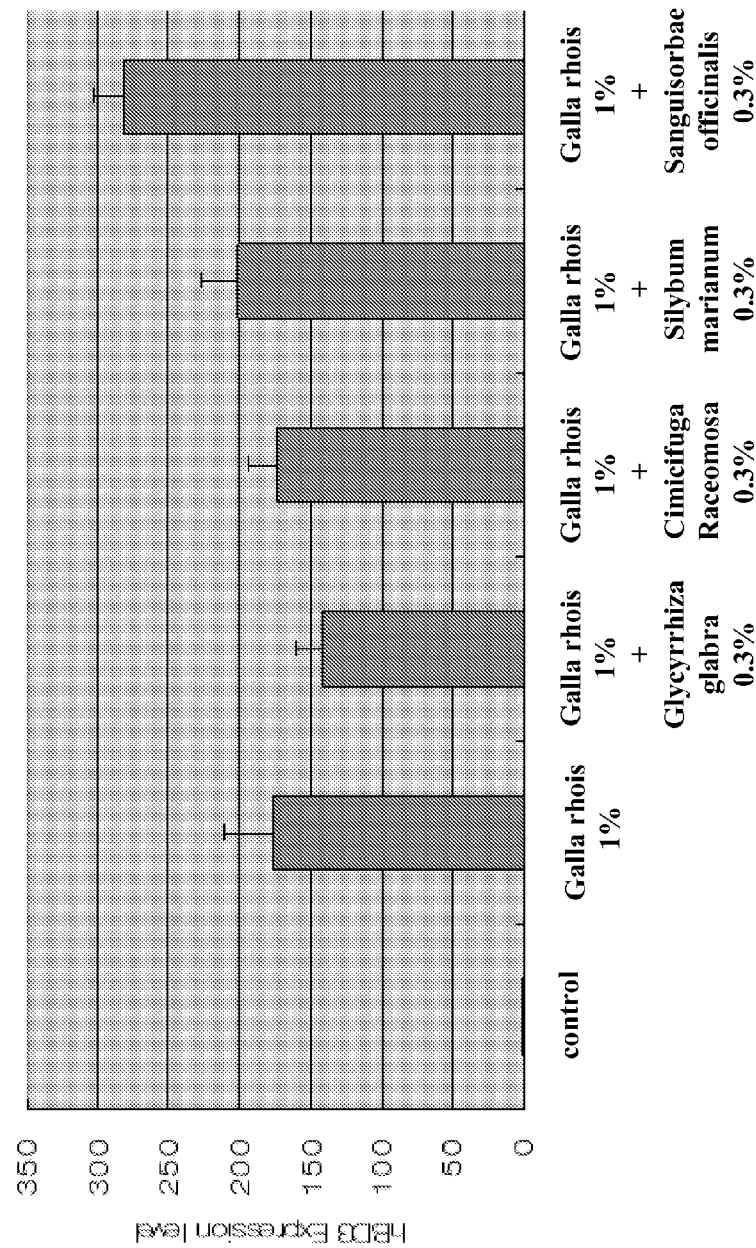

Synergistic effect of herbal extracts on stimulation of beta-defensin 3 is shown in FIGS. 15B and 15C. *Sanguisorbae officinalis* extract has shown synergistic effect with *Ailanthus altissima* (FIG. 15B) and also with *Galla rhois gallnut* (FIG. 15C).

Summary

The purpose of this study was to determine if the test materials comprise synergistic activity on IL-13 inhibition or beta-defensin 3 stimulatory activities. Herbal mixtures were tested for their ability to inhibit IL-13 release in KU812 cells. The mixtures inhibited IL-13 release. When measured for stimulation of beta-defensin 3 expression in keratinocytes HaCaT cells, synergism between (1%) *Ailanthus* altissima with (0.33%) Sanguisorbae officinalis was shown. The activity of Ailanthus altissima was elevated by 2 fold with the addition of 0.33% Sanguisorbae officinalis extract. Synergism was shown also between (1%) Galla rhois and (0.33%) Sanguisorbae officinalis. The stimulation activity of (1%) Galla rhois was elevated by the addition of Sanguisorbae officinalis from 175% to 280%.

Example 9

Extracts Optimization

Materials and Experimental Procedures

Enrichment of the Active Ingredients/Resin Chromatography

As described in Example 2, hereinabove.

IL-13 Inhibition

As described in Example 1, hereinabove.

Beta-Defensin Stimulation

As described in Example 2, hereinabove.

Anti-microbial Activity of the Herbal Extracts

Herbal extracts were screened for their anti-microbial activity against S. aureus and ampicillin-resistant E. coli using the paper diffusion anti-microbial assay as was previously described. In short, 0.2 ml (2 mg/ml) of 25 selected herbal water extracts were loaded on paper discs. E. coli resistance was confirmed by the addition of diluted ampicillin at concentrations of 0-50 µg/ml. The discs were loaded on agar plates with an agar overlay containing S. aureus and Amp-resistant E. coli. The anti-microbial activities were examined by the appearance of a transparent zone (killing zone) around the disc.

Results

Active Ingredient Enrichment in Plant Extracts

Enrichment of the active ingredient as taught by the present invention takes advantage of macroporous resins which effectively absorb, enrich and purify the active ingredients in herbal extracts. This procedure removes organic salts and heavy metals, and also removes large quantities of starch, thus, improving product stability, expanding product shelf-life and resulting in better activities of the extract. Resins with different porous structure parameters (pore size, pore ratio, and specific surface areas) and different polarities (non-polarity, weak polarity, medium polarity, and strong polarity) are used.

Extract Enrichment—Resin Chromatography

Herbal extract efficacy is mostly dependent on the concentration of active ingredients. Commercial production of very concentrated extracts is a complicated process which frequently results in sediments and complicated standardization. Resin chromatography, on the other hand, results in a reduced concentration of impurities (residue after evaporation) and high levels of active ingredients relevant to the treatment, which allows high biological efficacy and better standardization.

The present inventors have therefore developed an extraction method using macrospore resin for the herbal extracts that exhibited high efficacy as IL-13 inhibitors and/or as defensin stimulators. The herbal extracts and their active ingredients that were chosen as markers are presented in Table 6, below. The herbal extracts that were found initially as IL-13 inhibitors were already optimized by resin chromatography in the in-vitro studies described above and presented in FIGS. 14A-E and 15A-C.

TABLE 6

Herbal extracts active ingredients (markers)

| Herb | Marker (Active ingredient) |
|---|---|
| Ailanthus altissima cortex | Ailanthone, Mersosin, Toosendanin |
| Cimicifuga raceomosa | General Ginsenoide |
| Galla rhois gallnut | Galic acid, Tannic Acid |
| Glycyrrhiza glabra | Liquiritin |
| Peucedanum praeruptorum | Praeruptorin A |
| Sanguisorbae officinalis | Tannic acid |
| Silybum marianum | Silybin |

Optimization of herbal extracts that exhibit high efficacy as defensin stimulators and/or as IL-13 inhibitors. Marker and resin type were chosen for each herbal extract.

IL-13 Inhibition Before and after Extract Optimization

Herbs that were initially found as beta-defensin stimulators were also optimized using resin chromatography and their ability to inhibit IL-13 release was detected and compared to the activity of the extracts prior to optimization. Comparison between herbal extracts ability to inhibit IL-13 before and after optimization with resin chromatography is presented in FIG. 16 and in Table 7, below. Thus, the results show that resin chromatography elevated the biological activity of herbal extracts (by 2 fold for Ailanthus altissima extract, 1.13 fold for Galla rhois gallnut extract and by 36 fold for Peucedanum praeruptorum extract).

Figure 16:
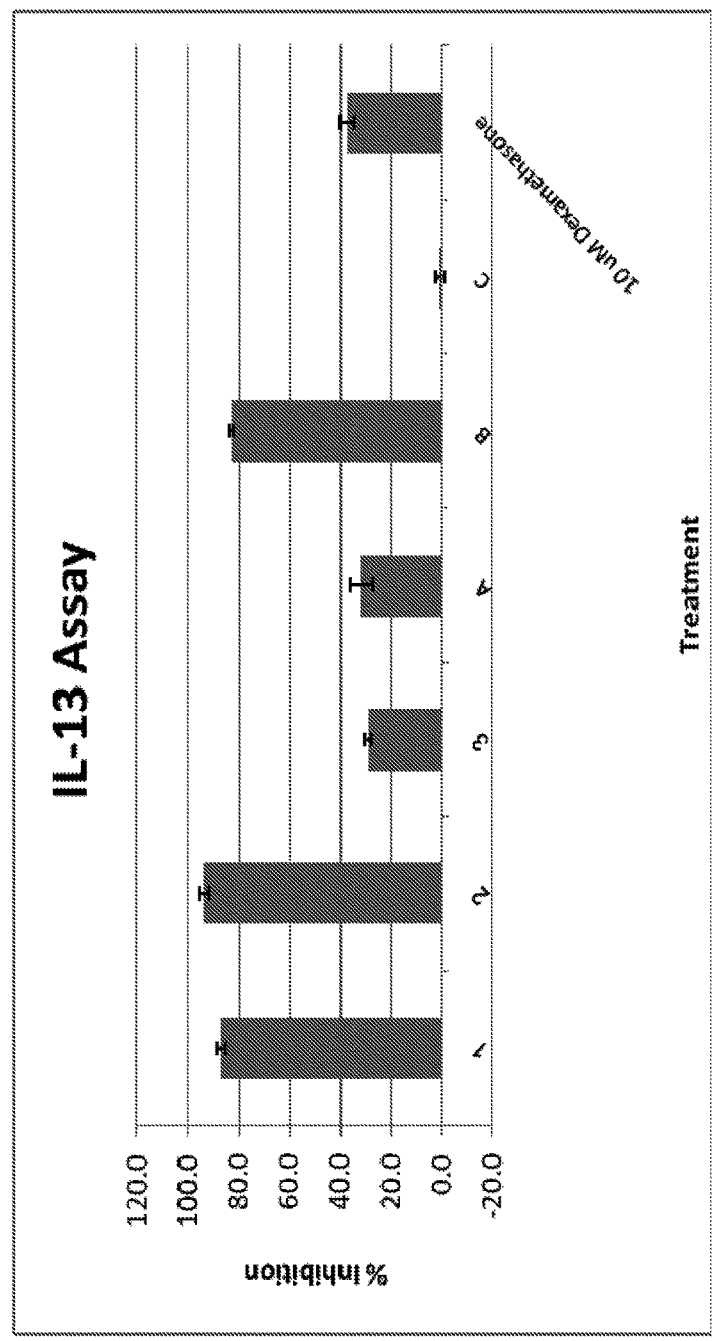
FIG. 16 is a bar graph depicting IL-13 inhibitory activity of herbal extracts before (A-C) and after (1-3) resin chromatography. Herbal extracts were measured in 0.3% for their ability to inhibit IL-13. The test material identification before and after chromatography optimization respectively: A, 1—*Ailanthus altissima;* B, 2—*Galla rhois gallnut;* C, 3—*Peucedanum praeruptorum*.

TABLE 7 comparison of herbal extracts IL-13 inhibition activity before and after chromatography optimization. Extracts numbers/ letters according to FIG. 16 are noted

| Herbal extract | % Inhibition of IL-13 before optimization | % Inhibition of IL-13 after optimization |
|---|---|---|
| Ailanthus altissima | 31.8% (A) | 87% (1) |
| Galla rhois gallnut | 83% (B) | 93.6% (2) |
| Peucedanum praeruptorum | 0.8% (C) | 28.8% (3) |

Anti-microbial Activity of the Herbal Extracts

Figure 17B:
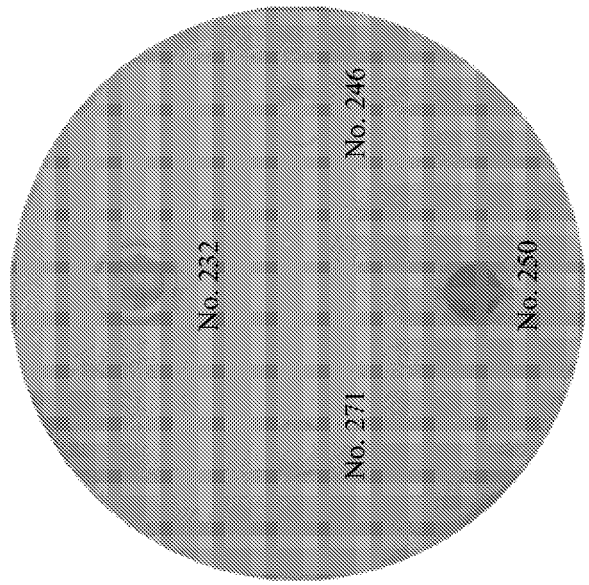
FIGS. 17A-B are photographs depicting the anti-microbial activity of Galla Rhois extract (No. 232).
Figure 17A:
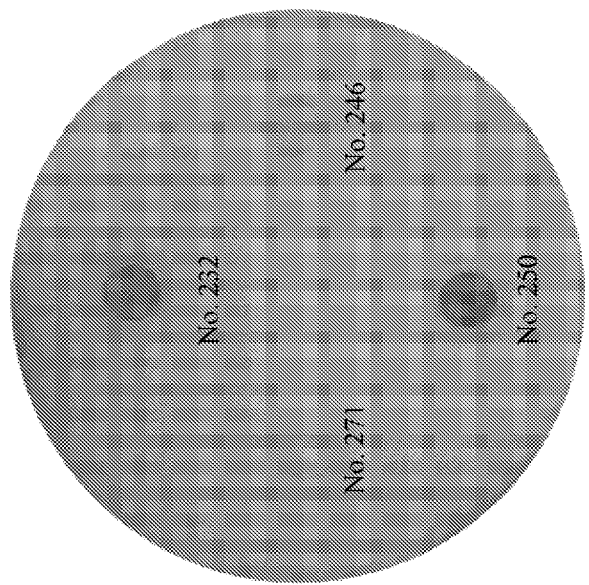

Herbal extracts were further screened for their anti-microbial activity against S. aureus and ampicillin-resistant E. coli. The present inventors used the paper diffusion anti-microbial assay to test 25 selected herbal extracts. First, E. coli resistance was confirmed by the addition of diluted ampicillin at concentrations of 0-50 mg/ml. As expected, the ampicillin-resistant E. coli showed strong survival even after treatment with 50 mg/ml of ampicillin. Next, S. aureus and ampicillin-resistant E. coli were tested for growth in the presence of herbal extracts (see Table 8, below, and FIGS. 17A-B). As shown in Table 8 and in FIGS. 17A-B, Galla rhois gallnut and Terminariae fructus extracts exhibited strong anti-microbial activities against both S. aureus and ampicillin-resistant E. coli while Coptidis rhizome extract inhibited only E. coli.

TABLE 8 comparison of the anti-microbial activity of herbal extracts

| No. | Name of herbs | Against S. aureus | Against E. coli (Amp-resistance) |
|---|---|---|---|
| Positive control | 50 ug/ml Amp | ++++++ | + |

TABLE 8-continued comparison of the anti-microbial activity of herbal extracts

| No. | Name of herbs | Against *S. aureus* | Against *E. coli* (Amp-resistance) |
|---|---|---|---|
| Positive control | 5 ug/ml Amp | ++++ | − |
| Positive control | 0.5 ug/ml Amp | ++ | − |
| Negative control | D.W. | − | − |
| No. 2 | *Terminariae Fructus* | ++ | ++ |
| No. 232 | *Galla Rhois* | + | + |
| No. 352 | *Coptidis Rhizoma* | − | +++ |

Final Herbal Mixture

The extracts that exhibited the most significant activity as IL-13 inhibitors and/or as defensin stimulators were chosen for the development of the final product.

The herbal extracts that exhibited significant stimulation on beta-defensin were: *Ailanthus altissima, Galla rhois gallnut* and *Peucedanum praeruptorum*. Both, *Ailanthus altissima* and *Galla rhois gallnut* also exhibited significant IL-13 inhibitory activity.

The herbal extracts that exhibited the most significant IL-13 inhibitory activity in the primary assay were: *Glycyrrhiza glabra, Cimicifuga raceomosa, Silybum marianum* and *Sanguisorbae officinalis*. *Sanguisorbae officinalis* had also shown significant beta-defensin 3 stimulation activity and also exhibited synergistic effect with *Ailanthus altissima* and *Galla rhois gallnut* extracts.

Thus, the final herbal mixture of the present teachings comprises: *Ailanthus altissima, Sanguisorbae officinalis, Glycyrrhiza glabra* and *Cimicifuga raceomosa*.

Certificate of Analysis (CoA)

A certificate of analysis (CoA) was made for the herbal extracts containing the final mixture. The main characteristics of the herbal extracts are presented in Table 9, below.

The CoA represent values of active ingredient (marker), residue after evaporation and pH for each herbal extract following extract optimization using macroporous resin chromatography. Heavy metals exhibited values≤20 ppm for all herbal extract. Microbiological tests were perform for each extract while total count were <$10^2$/g, mold & yeast<$10^2$/g and Salmonela and *E. coli* form were found negative for all the herbal extracts tested.

TABLE 9

CoAs for the final herbal extracts in the mixture

| Nature of Test | *Ailanthus altissima* | *Sanguisorbae officinalis* | *Glycyrrhiza glabra* | *Cimicifuga raceomosa* |
|---|---|---|---|---|
| Characteristics | | | | |
| Appearance | Sticky liquid | Sticky liquid | Sticky liquid | Sticky liquid |
| Color | Dark brown | Dark brown | Dark brown | Dark brown |
| Odor | Characteristic herbal | Characteristic herbal | Characteristic herbal | Characteristic herbal |
| Density at 25° C., g/ml | 1.02 | 1.04 | 1.02 | 1.02 |
| pH Value | 6.1 | 5.4 | 6.1 | 5.7 |
| Tests | | | | |
| Heavy metals, | ≤20 ppm | <20 ppm | <20 ppm | <20 ppm |
| Residue after evaporation | 14.2% | 26.1% | 18.2% | 19.3% |
| Assay HPLC | Ailanthone/Mersosin 0.75 mg/ml/ Toosendanin 0.01 mg/ml | Gallic acid 0.04 mg/ml/ Tannic Acid 62.3 mg/ml | Liquiritin 4.1 mg/ml | General Ginsenoside 51.6 mg/ml |
| Microbiological Tests | | | | |
| Total Plate Count | <$10^2$/g | <10/g | <10/g | <10/g |
| Yeasts and Molds | <$10^2$/g | <10/g | <10/g | <10/g |
| *Salmonella* | Negative in 1 g | Negative in 1 g | Negative in 1 g | Negative in 1 g |
| *E. coliform* | Negative in 1 g | Negative in 1 g | Negative in 1 g | Negative in 1 g |

Product Formulation

The present inventors developed O/W formulation containing the chosen herbal extract/s mixture. In addition to the herbal extract efficacy, the formulation was developed to moisturize dry skin related to atopic dermatitis patients, therefore, the formulation also contained emollients and moisturizers substances.

The product was designated to have a pH of approximately five, a level similar to normal skin. Topical products containing normal skin pH support the integrity of the stratum corneum, and the formation and maturation of the lipid lamellae. The pH value has an important role in atopic dermatitis patients, particularly with respect to skin barrier function and colonization with *Staphylococcus aureus*.

Example 10

Clinical Trials

Materials and Experimental Procedures

SCORAD

The degree of AD was evaluated by SCORAD INDEX, a clinical tool used to assess the extent and severity of eczema (SCORing Atopic Dermatitis), as previously described [Oranje A P et al., Br J. Dermatol. (2007) 157(4):645-8; Oranje A P, Curr Probl Dermatol. (2011) 41:149-55]. SCORAD is typically used by dermatologists before and after treatment to determine whether the treatment has been effective.

The parameters of the SCORAD are:

Extent

To determine extent, the sites affected by eczema are typically shaded on a drawing of a body. The rule of 9 is used to calculate the affected area (A) as a percentage of the whole body, as follows: Head and neck 9%, Upper limbs 9% each, Lower limbs 18% each, Anterior trunk 18%, Back 18% and 1% each for genitals, each palm and the back of each hand.

The score for each area is added up. The total area is 'A', which has a possible maximum of 100%.

Intensity

A representative area of eczema is selected. In this area, the intensity of each of the following signs is assessed as none (0), mild (1), moderate (2) or severe (3), as follows: Redness, Swelling, Oozing/crusting, Scratch marks, Skin thickening (lichenification) and Dryness (this is assessed in an area where there is no inflammation).

The intensity scores are added together to give 'B' (maximum 18).

Subjective Symptoms

Subjective symptoms i.e., itch and sleeplessness, are each scored by the patient or relative using a visual analogue scale where 0 is no itch (or no sleeplessness) and 10 is the worst imaginable itch (or sleeplessness). These scores are added to give 'C' (maximum 20).

Total Score

The SCORAD for an individual is A/5+7B/2+C

Composition for Clinical Trial

The subjects who participated in the clinical trial (see further details herein below) received treatment with either carrier, a product which contains herbal extracts that reduce pruritus and moisturizers that hydrate the skin to enable a treatment of mild and moderate AD symptoms, or with treatment lotion which on top of the ingredients used in the carrier lotion also contains two additional herbal extracts: *Sanguisorba officinalis* root extract and *Ailanthus altissima* extract (see Table 10 for an exemplary treatment lotion formulation used in a clinical trial). The carrier lotion also contain two extracts that inhibited IL-13

TABLE 10

An exemplary treatment body lotion formulation

| INCI Name | INCI 9th. Ed page no. | CAS No. |
|---|---|---|
| Aqua | 1795 | 7732-18-5 |
| Petrolatum | 12th Ed. 1983 | 8009-03-8 |
| Glycerin | 666 | 56-81-5 |
| *Butyrospermum Parkii* (Shea Butter) | 12th Ed. 365 | 68920-03-6 |
| Mineral Oil | 12th Ed. 1597 | 8012-95-1 |
| Caprylic/Capric Triglyceride | 252 | 65381-09-1 |
| Cetearyl Alcohol & Cetearyl Glucoside Cetyl Alcohol & Stearyl Acetate & | 12th Ed. 476 12th Ed. 479 12th Ed. 2663 | 8005-44-5 — 822-23-1 |
| Oleyl Acetate & | 12th Ed. 1719 | 693-80-1 |
| Acetylated Lanolin Alcohol | 12th Ed. 15 | 61788-49-6 |
| Cetyl Alcohol | 12th Ed. 492 | 36653-82-4 |
| Cetearyl Ethylhexanoate | 12th Ed. 478 | — |
| Cetearyl Alcohol | 12th Ed. 476 | 8005-44-5 |
| Dipotassium Glycyrrhizate | 545 | 68797-35-3 |
| Ceramide 3 & | 12th Ed. 461 | 100403-19-8 |
| Ceramide 6 II & | 12th Ed. 462 | 100403-19-8 |
| Ceramide 1 & | 12th Ed. 460 | 100403-19-8 |
| Phytosphingosine & | 12th Ed. 2014 | 544-62-1 |
| Cholesterol & | 12th Ed. 523 | 57-88-5 |
| Sodium Lauroyl Lactylate & | 12th Ed. 2546 | 133557-75-0 |
| Carbomer & | 12th Ed. 429 | 9003-01-4 |
| Xanthan Gum | 12th Ed. 2975 | 11138-66-2 |
| Glyceryl Stearate & | 12th Ed. 1080 | 123-94-4 |
| PEG-100 Stearate | 12th Ed. 1944 | 9004-99-3 |
| *Rheum Palmatum* Root Extract | 2067 | 90106-27-7 |
| *Cnidium Monnieri* Fruit Extract | 12th Ed. 626 | 484-12-8 |
| *Scutellaria Baicalensis* Root Extract | 12th Ed. 2444 | 94279-99-9 |
| *Sanguisorba Officinalis* Root Extract | | 84787-71-3 |
| *Ailanthus Altissima* Extract | | 90131-67-2 |
| Dehydroacetic Acid & | 12th Ed. 749 | 520-45-6 |
| Benzyl Alcohol | 12th Ed. 271 | 100-51-6 |
| Sucrose Stearate | | 25168-73-4 |
| Dimethicone | 12th Ed. 814 | 9006-65-9 |
| Pentadecalactone & | 12th Ed. 1960 | 106-02-5 |
| Triethyl Citrate | 12th Ed. 2806 | 77-93-0 |
| Xanthan Gum | 12th Ed. 2975 | 11138-66-2 |
| Potassium sorbate | 12th Ed. 2177 | 590-00-1 |
| Tocopheryl Acetate | 12th Ed. 2778 | 58-95-7 |
| Lactic Acid | 12th Ed. 1378 | 50-21-5 |
| Hyaluronic Acid | 12th Ed. 1177 | 9004-61-9 |

Subjects

Inclusion Criteria:

The inclusion criteria for participating in the present clinical trial was as follows: male and females above 18 years of age; diagnosis of atopic dermatitis must meet Hanifin's criteria (at least 3 basic features and at least 3 minor features); atopic dermatitis has been, in the opinion of the inventors, stable for the past 7 days; no new flare ups in the last 5 days; able to apply the study product at least twice a day (each morning and evening) for a 21 days period; subjects that agreed not to change their lifestyle during the study period (including their usual body hygiene product (soap), the number of baths and showers per day, the laundry detergent and fabric softener used to wash the clothes); subjects that agreed to use only the test product during the study period' and subjects who were willing to sign an informed consent.

Exclusion Criteria:

The exclusion criteria for the present clinical trial was as follows: subject had another dermatological disease/condition that could interfere with clinical evaluation including infected atopic dermatitis lesions; subject had a previous history of allergy to cosmetic products or any ingredients of the tested formulations; subject had received any topical or systemic immunomodulators for atopic dermatitis (such as pimecrolimus or tacrolimus) or steroids within 14 days of Day 0; subject had received phototherapy within 28 days of Day 0; extended sun exposure time during the trial; subject had used any experimental treatment within 14 days of Day 0; and pregnant or lactating females.

Participation was voluntary. The inventors provided a copy of the informed consent form to each enrollee.

The subjects underwent 3 scheduled clinic visits during the study:
1. Screening evaluation/baseline (Day 0)
2. Follow up visits—Day 7, Day 14
3. Completion Visit—Day 21

(Flexibility of ±2 days was permitted due to patient availability).

On Day 7, Day 14 and Day 21 (±2 days), the subjects returned to the clinic for evaluation. The following assessments were made: Extent, edema, erythema, pruritus, lichenification, oozing, insomnia and dryness. Based on these measurements SCORAD was calculated and secondary infection assessments were performed.

On the first and on the final visit, TEWL and Skin Hydration testing were performed.

The study was carried out in accordance with international standards, which meet regulations relating to Good Clinical Practice (GCP).

All patients were informed about the aims, methods, anticipated benefits, potential hazards and confidentiality of data. Candidates were also told that they are free to refuse participation at any time.

Patient Evaluation

Primary Outcome Measure:

SCORAD including graded AD symptoms: extent, edema, oozing, excoriation, lichenification, erythema, pruritus, dryness and insomnia [Time Frame: Day 0, Day 7, Day 14 and Day 21].

Secondary Outcome Measures:
1. TEWL and Hydration testing [Time Frame: Day 0 and day 21]
2. Number and grading of secondary infections
3. Number of Adverse Events [Time Frame: Day 0, Day 7, Day 14, and Day 21]

Results

Baseline Demographic and AD Characteristics

A total of 50 subjects participated in the study (i.e. two studies were conducted simultaneously one comprising 30 subjects treated with the treatment lotion and 20 subjects were treated with the carrier lotion, see summary in Table 11, below). Thirty patients were treated with treatment lotion and 20 patients were treated with the carrier for 21 days. Mean age was similar in both groups. Although there were gender differences between both groups (Table 11), the baseline AD severity in both groups, as measured by SCORAD, was similar (Table 12, below). Moreover, proportion of subpopulations of AD patients with severe symptoms (SCORAD>50) was also identical in both groups (25% in carrier group and 26.7 in treatment group) (see Table 12, below).

TABLE 11

Demographic characteristics of both groups

| Characteristic | Control (carrier group) | Treatment (treatment group) |
|---|---|---|
| Number | 20 | 30 |
| Age, y (SD) | 45 (13) | 48 (15) |
| Female, No. (%) | 5 (25) | 28 (93) |
| Male, No. (%) | 15 (75) | 2 (7) |

TABLE 12

Baseline values of SCORAD

| Severity of AD | Control (carrier group) | Treatment (treatment group) |
|---|---|---|
| Total SCORAD | | |
| Number of subjects | 20 | 30 |
| SCORAD (SD) | 41 (12) | 42 (12) |
| Mild to Moderate SCORAD <50 | | |
| Number of subjects (%) | 15 (75%) | 22 (73.3%) |
| SCORAD (SD) | 33 (9) | 37 (9) |
| Severe SCORAD >50 | | |
| Number of subjects (%) | 5 (25%) | 8 (26.7%) |
| SCORAD (SD) | 53 (3) | 57 (4) |

Analysis of SCORAD Results

Figure 18:
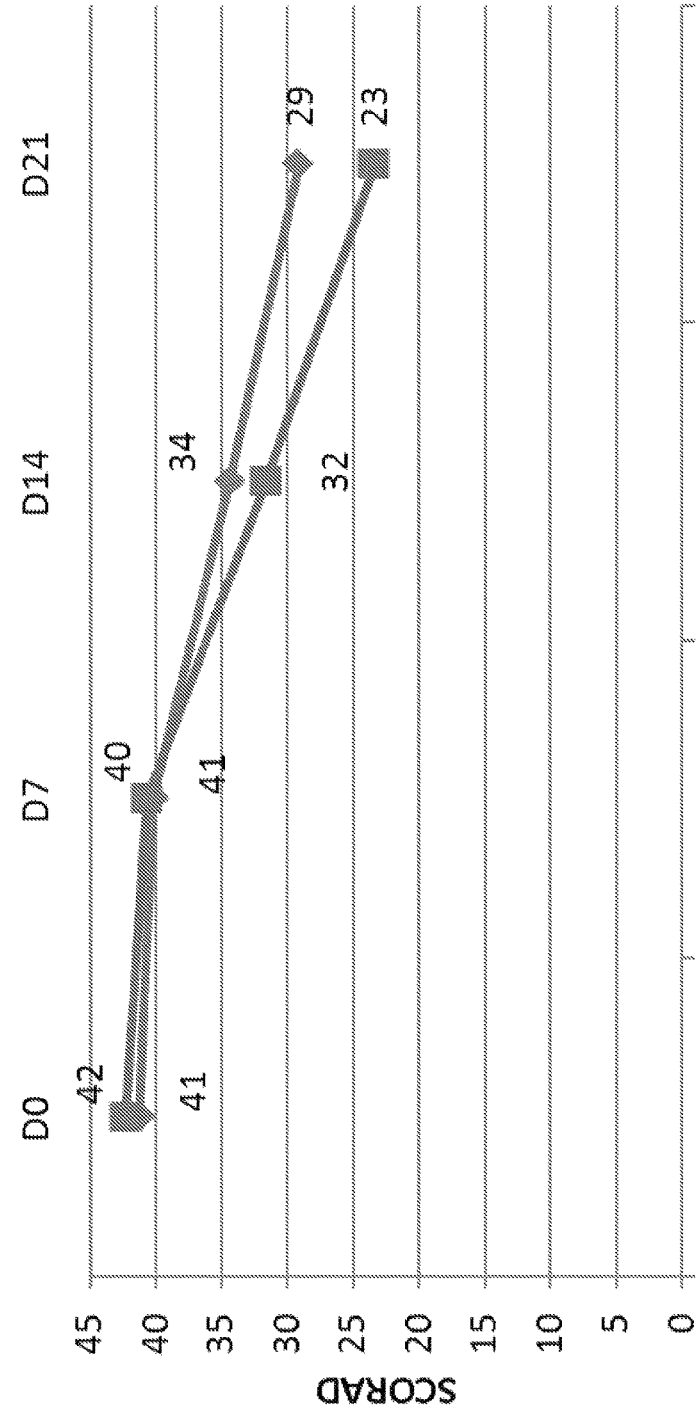
FIG. 18 is a line graph depicting SCORAD reduction over time in carrier (depicted by diamond) and treatment (composition comprising *Sanguisorba officinalis* and *Ailanthus altissima*, depicted by square) treated subjects (assessed on days 0, 7, 14 and 21).

A significant difference was observed between SCORAD of carrier and treatment groups on Days 14 and 21 (for both p<0.001) as compared to baseline values (see FIG. 18), indicating efficient reduction of AD appearance by both preparations.

No overall difference in SCORAD between the groups was found. After 3 weeks, the mean score of the treatment group was slighter lower than in carrier group (p=0.087). However, closer analysis by individual parameters, as shown below, discloses significant changes.

Analysis of SCORAD Main Components

Figure 19:
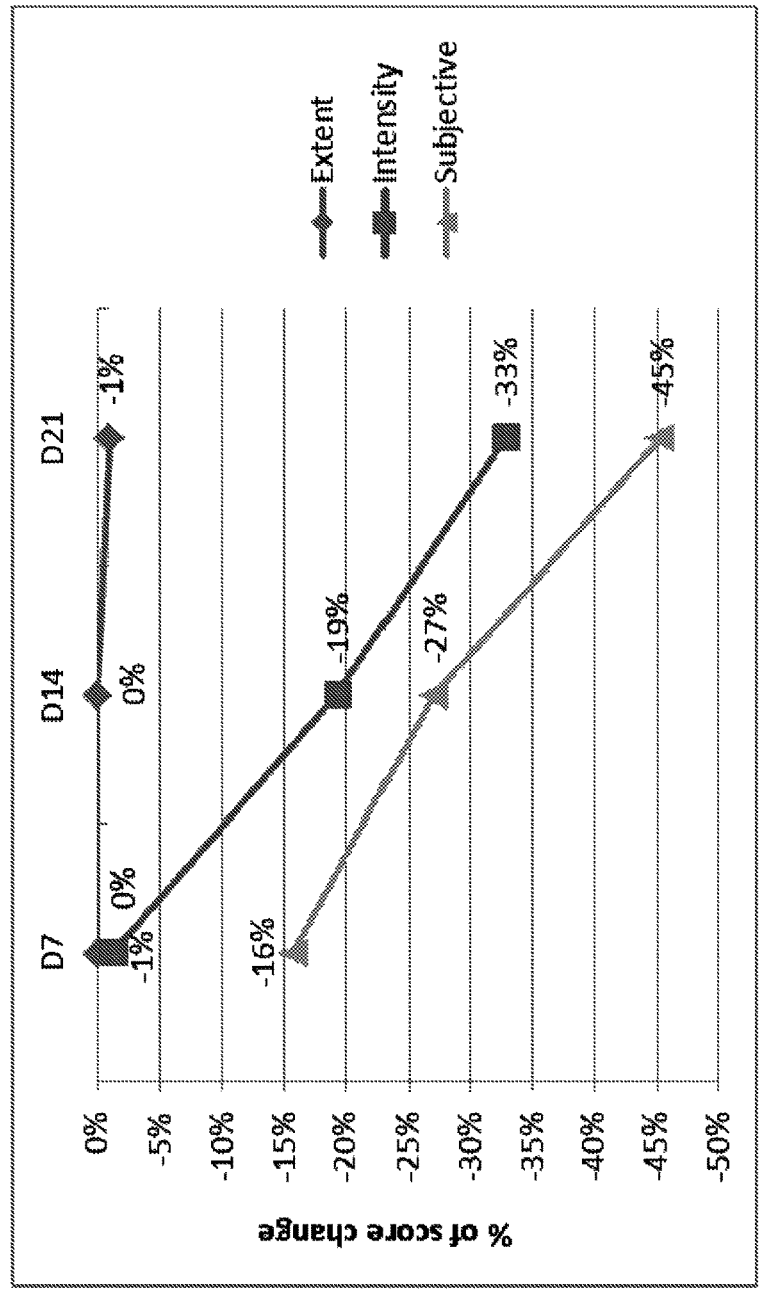
FIG. 19 is a line graph depicting the effect of the SCORAD components (extent, intensity and subjective) on the total score in the carrier treated group (on days 7, 14 and 21).
Figure 20:
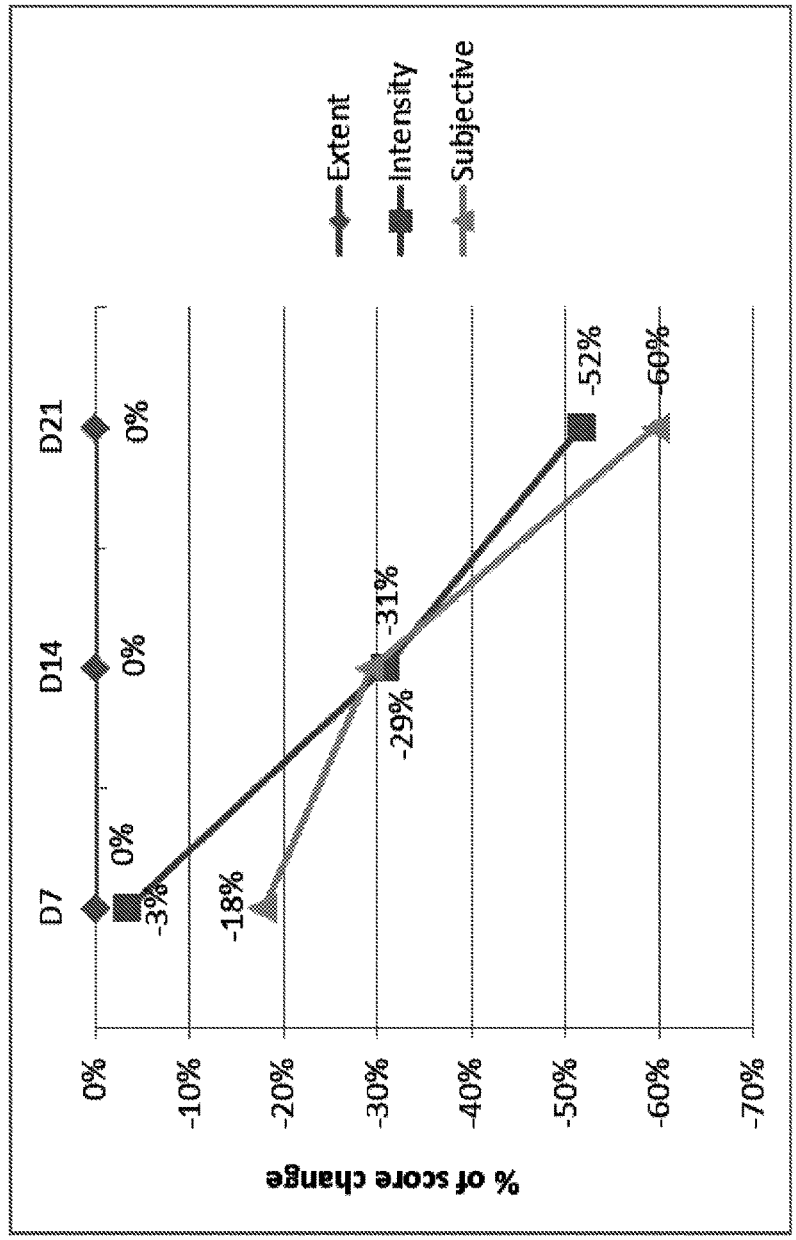
FIG. 20 is a line graph depicting the effect of the SCORAD components (extent, intensity and subjective) on the total score in the treatment group (composition comprising *Sanguisorba officinalis* and *Ailanthus altissima*, on days 7, 14 and 21).

The main SCORAD components (extent, intensity, subjective) were examined separately in carrier and treatment groups for contribution to the significant total SCORAD decline over the time (FIGS. 19 and 20, respectively).

The graph in FIG. 19 demonstrates stability of the extent parameter in carrier group during the study. This component does not affect the change in the total SCORAD score. On the other hand, the change in intensity and subjective parameters on Days 14 and 21 was highly significant (p<0.001 and p<0.01, respectively) when compared to baseline.

The same results were obtained in the treatment group (see FIG. 20). The extent did not contribute to the change in the total SCORAD value. Intensity and subjective parameters significantly declined on Days 14 and 21 (for both p<0.001) when compared to the baseline.

Intensity parameter is a sum of scores of six AD symptoms. Overall difference in intensity parameter and, particularly, the difference between the groups on Day 21, was highly significant (FIG. 21, p<0.01).

Figure 22:
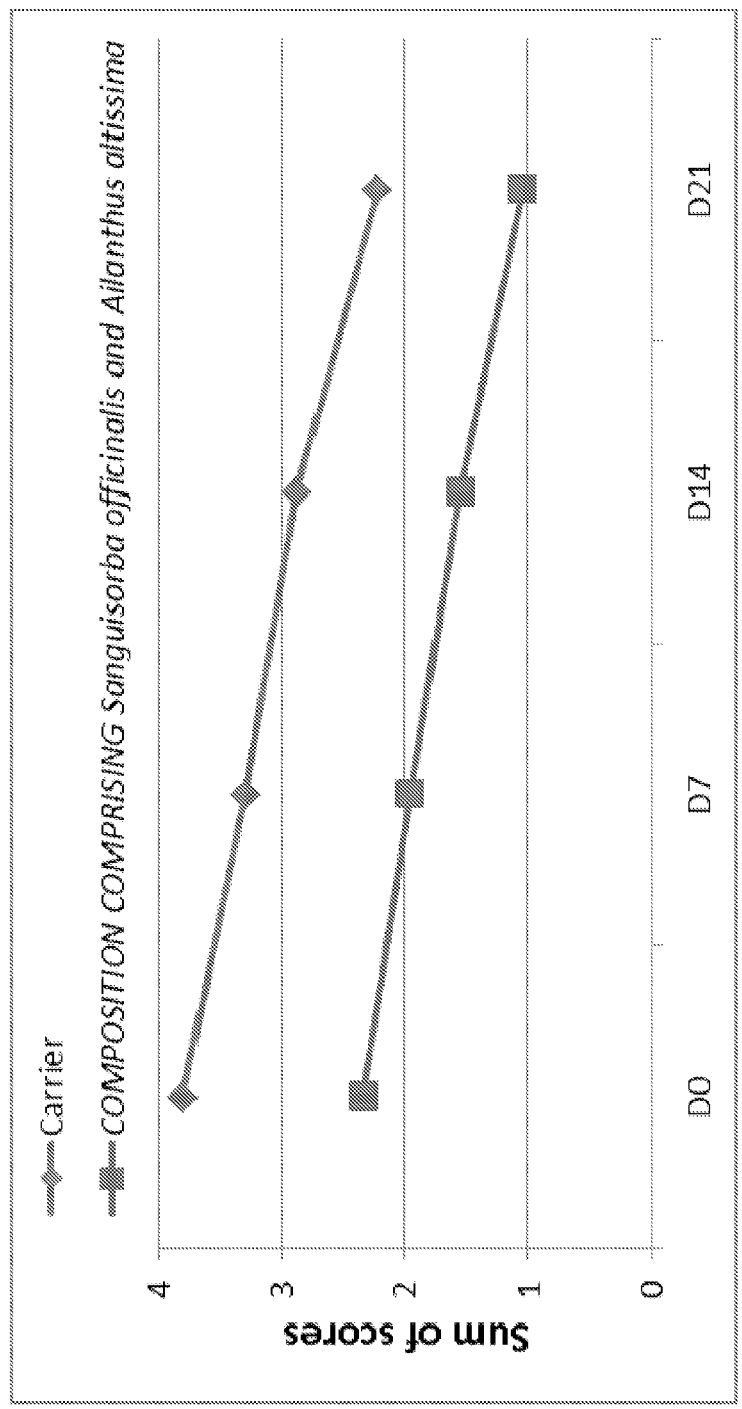
FIG. 22 is a line graph depicting a comparison between the carrier and treatment groups: reduction of subjective scores over time (assessed on days 0, 7, 14 and 21).

In contrast, no differences were observed between the groups in the subjective parameters, composed of the score sum of pruritus and insomnia symptoms, as assessed by subjects (FIG. 22).

Taken together these results show that the change in intensity and subjective parameters on Days 14 and 21 was highly significant in each group when compared to its baseline. The extent remained stable in both groups during the study, thus diminishing a significance of the total SCORAD decline. Although no significant change in the extent parameter was found, the lesions severity in each of the measured areas decreased significantly, as shown by reduction in intensity parameter.

Figure 21:
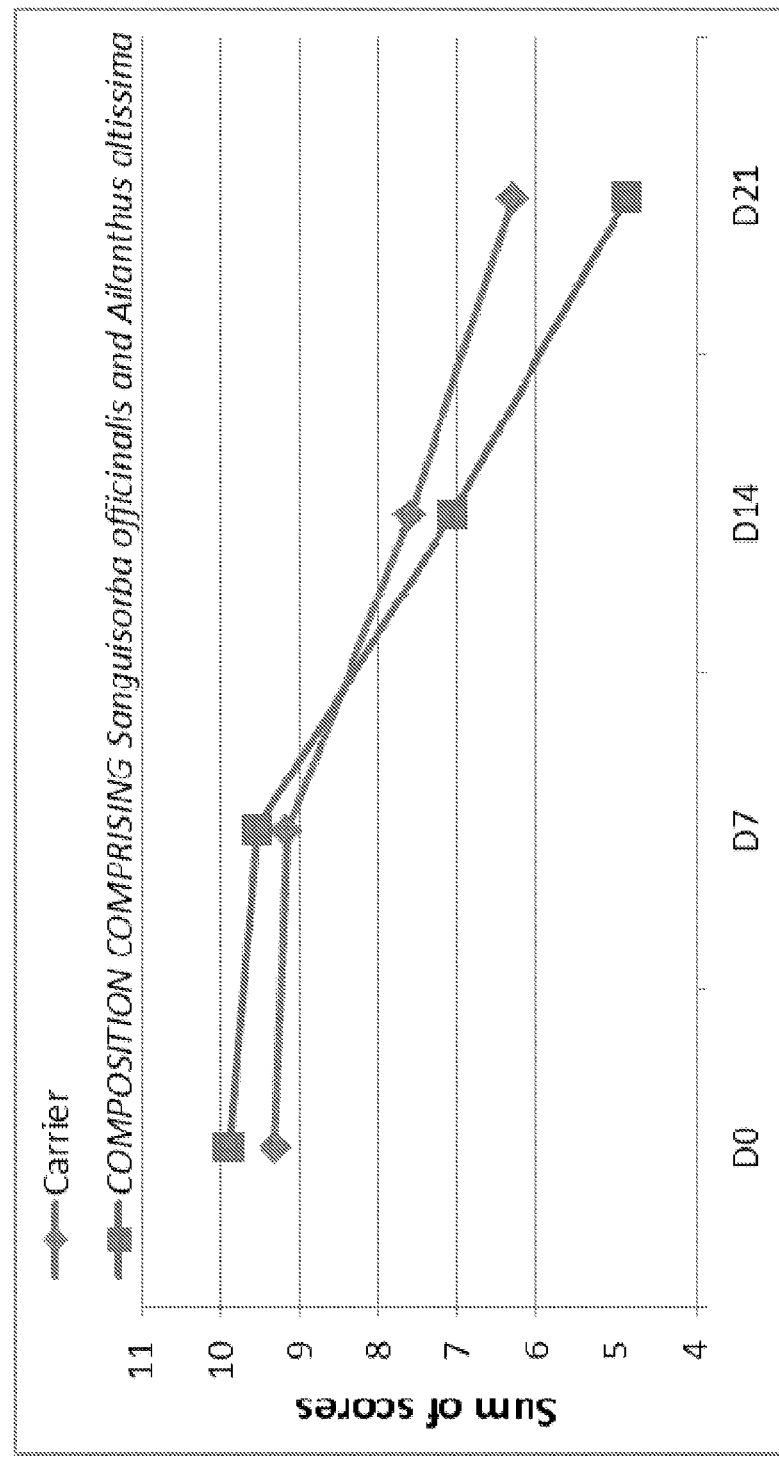
FIG. 21 is a line graph depicting a comparison between the carrier and treatment groups: intensity reduction over time (assessed on days 0, 7, 14 and 21).

Comparison between the groups after 21 days revealed a higher significant reduction in intensity following treatment with the treatment body lotion (52% versus 32% in carrier group, FIG. 21). No significant difference was observed in relative reduction of subjective parameter (55% in treatment versus 42% in carrier group, FIG. 22).

Analysis of Intensity Individual Components

Figure 23:
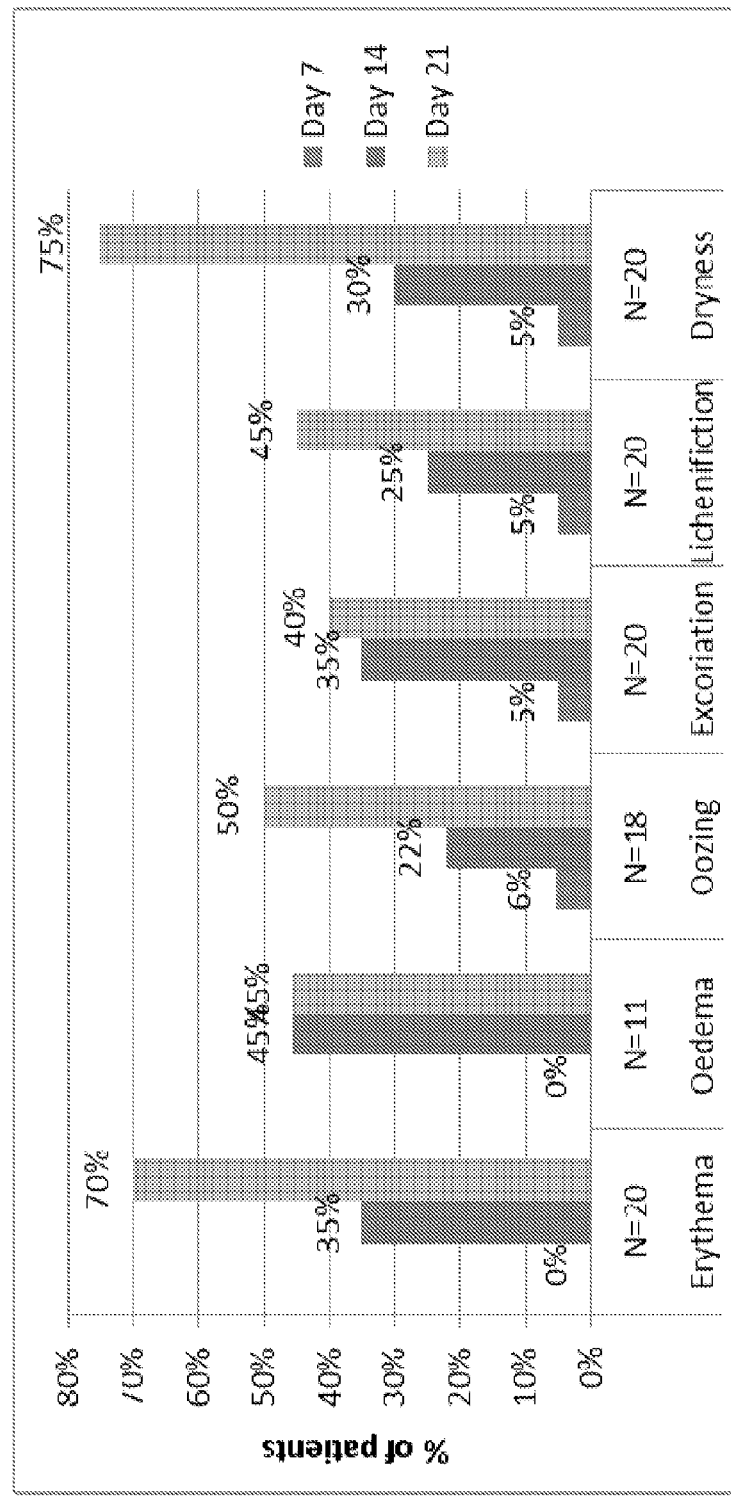
FIG. 23 is a bar graph depicting the percent of patients with improved symptoms in the carrier group (on days 7, 14 and 21).

Higher resolution analysis of individual intensity components (erythema, oedema, oozing, excoriation, lichentification and dryness) showed that a substantial percentage of AD patients experienced a significant improvement in the symptoms in both treatment groups. The analysis was made based only on the data taken from subjects whom experienced the symptoms. As illustrated in the results, two common symptoms in mild-moderate AD, erythema and dryness, have been improved in more than 70% of patients (FIG. 23).

The difference between scores of oozing, excoriation, lichenification and dryness was significantly different from baseline on Day 21 (see Table 13, below, p<0.01). The score of erythema significantly improved also on Day 14 (p<0.02).

TABLE 13

Change in scores (mean %) of individual symptoms in the carrier group

|        | Erythema | Oedema | Oozing | Excoriation | Lichenifiction | Dryness |
|--------|----------|--------|--------|-------------|----------------|---------|
| Day 7  | 0%       | 0%     | −3%    | 3%          | 3%             | 2%      |
| Day 14 | 18%      | 27%    | 17%    | 25%         | 15%            | 13%     |
|        | P < 0.02 |        |        |             |                |         |
| Day 21 | 34%      | 27%    | 39%    | 23%         | 28%            | 34%     |
|        | P < 0.001|        | P < 0.01 | P < 0.001 | P < 0.001    | P < 0.001 |

Figure 24:
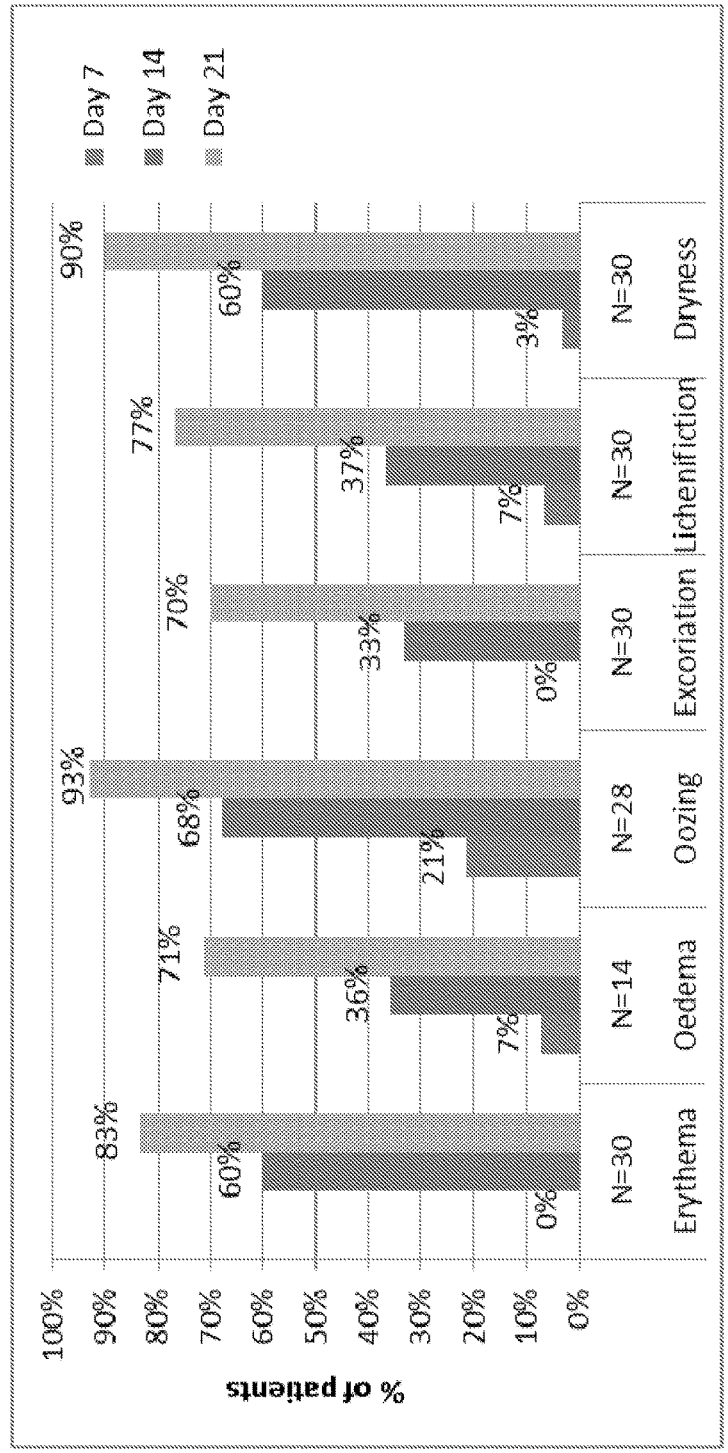
FIG. 24 is a bar graph depicting the percent of patients with improved symptoms in the treatment group (on days 7, 14 and 21).

Treatment body lotion was more effective than carrier body lotion, significantly reducing all the symptoms in more than 70% of patients after 21 days (FIG. 24).

Interestingly, that oozing symptom, associated with secondary infections, was improved by 86% in 93% of the subjects (see FIG. 24 and Table 14, below). The difference between scores on Day 14 and Day 21 versus baseline was highly significant (p<0.001) in all the symptoms except Oedema, which was significantly different only on Day 21 (p<0.02).

TABLE 14

Change in scores (mean %) of individual symptoms in the treatment group

|        | Erythema | Oedema | Oozing | Excoriation | Lichenifiction | Dryness |
|--------|----------|--------|--------|-------------|----------------|---------|
| Day 7  | 0%       | 2%     | 16%    | 0%          | 3%             | 1%      |
| Day 14 | 27%      | 23%    | 52%    | 22%         | 22%            | 26%     |
|        | P < 0.001|        | P < 0.001 | P < 0.008 | P < 0.003   | P < 0.001 |
| Day 21 | 37%      | 50%    | 86%    | 53%         | 53%            | 40%     |
|        | P < 0.001| P < 0.02 | P < 0.001 | P < 0.02 | P < 0.001    | P < 0.001 |

Figure 25:
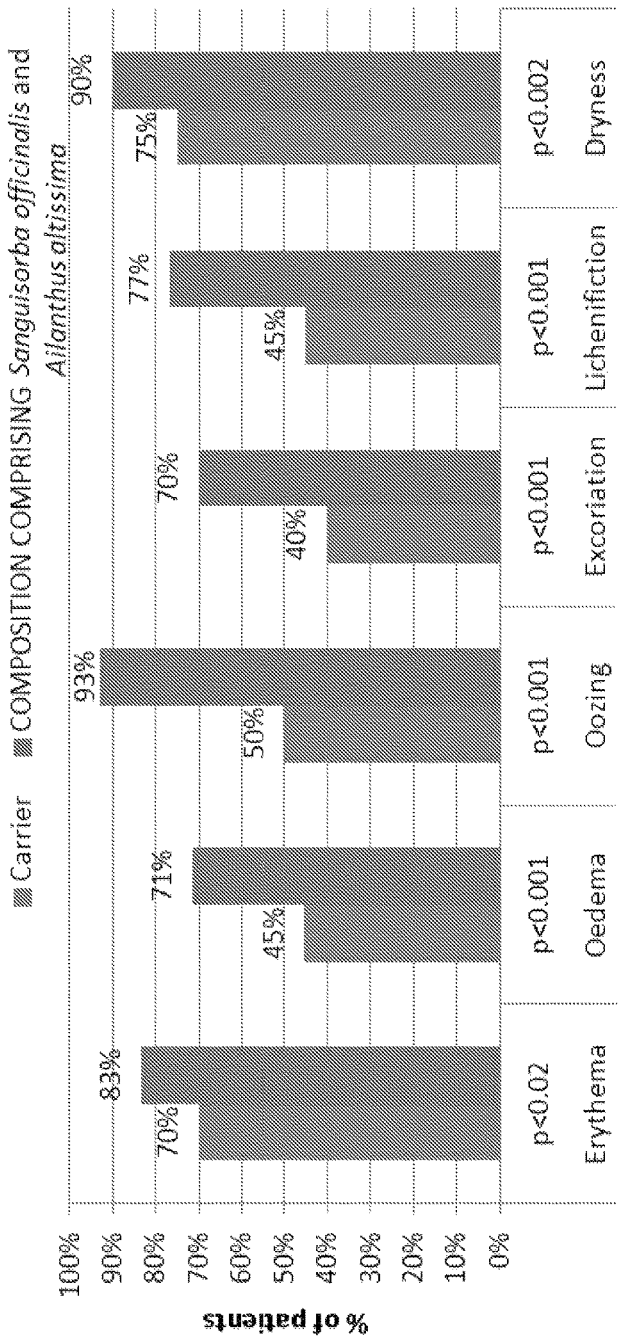
FIG. 25 is a bar graph depicting the percent of patients with improved symptoms in the treatment and carrier groups after 21 days of treatment.

A comparison between carrier and treatment groups revealed a vastly superior reducing effect of treatment body lotion on severity of AD symptoms. Significantly higher number of AD patients experienced improvement in AD condition, as assessed by the present inventors (FIG. 25).

Treatment group exhibited substantially higher degree of oozing improvement as compared to the carrier counterpart (see Table 15, below).

Thus, the most significant benefit of the treatment body lotion versus carrier was demonstrated in intensity reduction of oedema (50% versus 27%), oozing (86% versus 39%), excoriation (53% versus 23%) and lichenification (53% versus 28%), following 21 days of treatment (see Table 15).

Analysis of Subjective Individual Components

The analysis was made based only on the data taken from subjects whom indicated that they experienced the symptoms.

Figure 26:
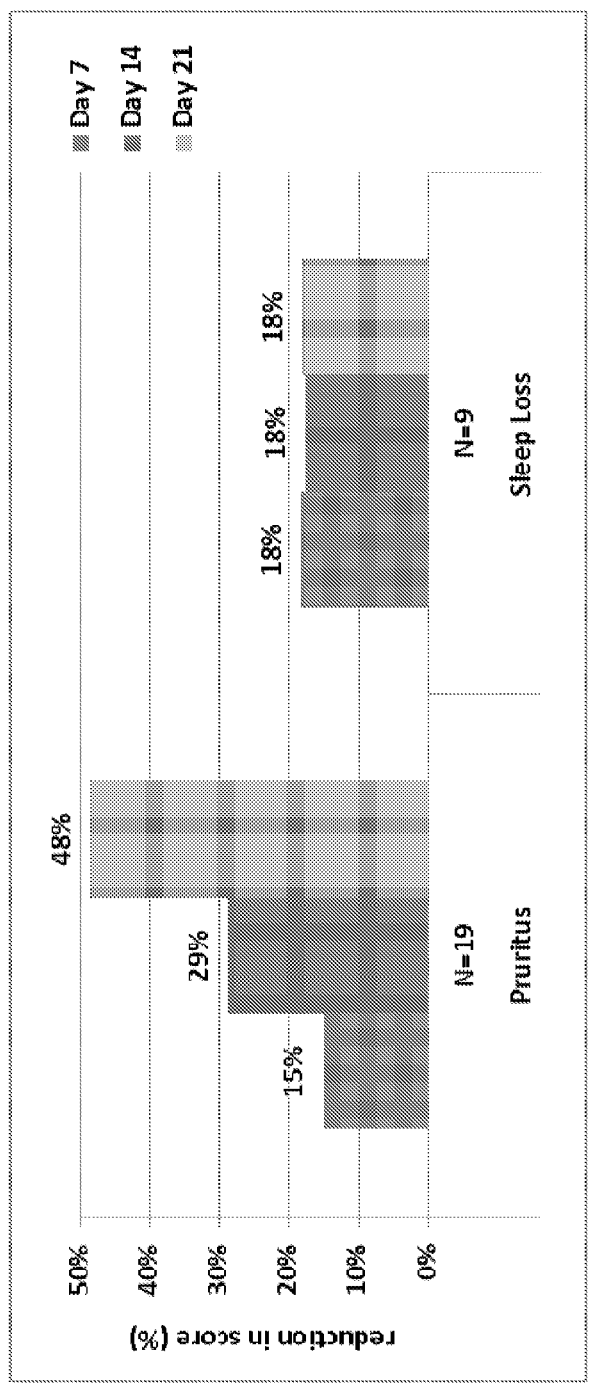
FIG. 26 is a bar graph depicting reduction in pruritus and sleep loss in the carrier group (on days 7, 14 and 21).

Significant reduction of pruritus (p<0.001), induced by carrier body lotion was observed, while not effecting the sleep loss of the patients, which was very low on baseline (mean=1.6) (see FIG. 26).

Figure 27:
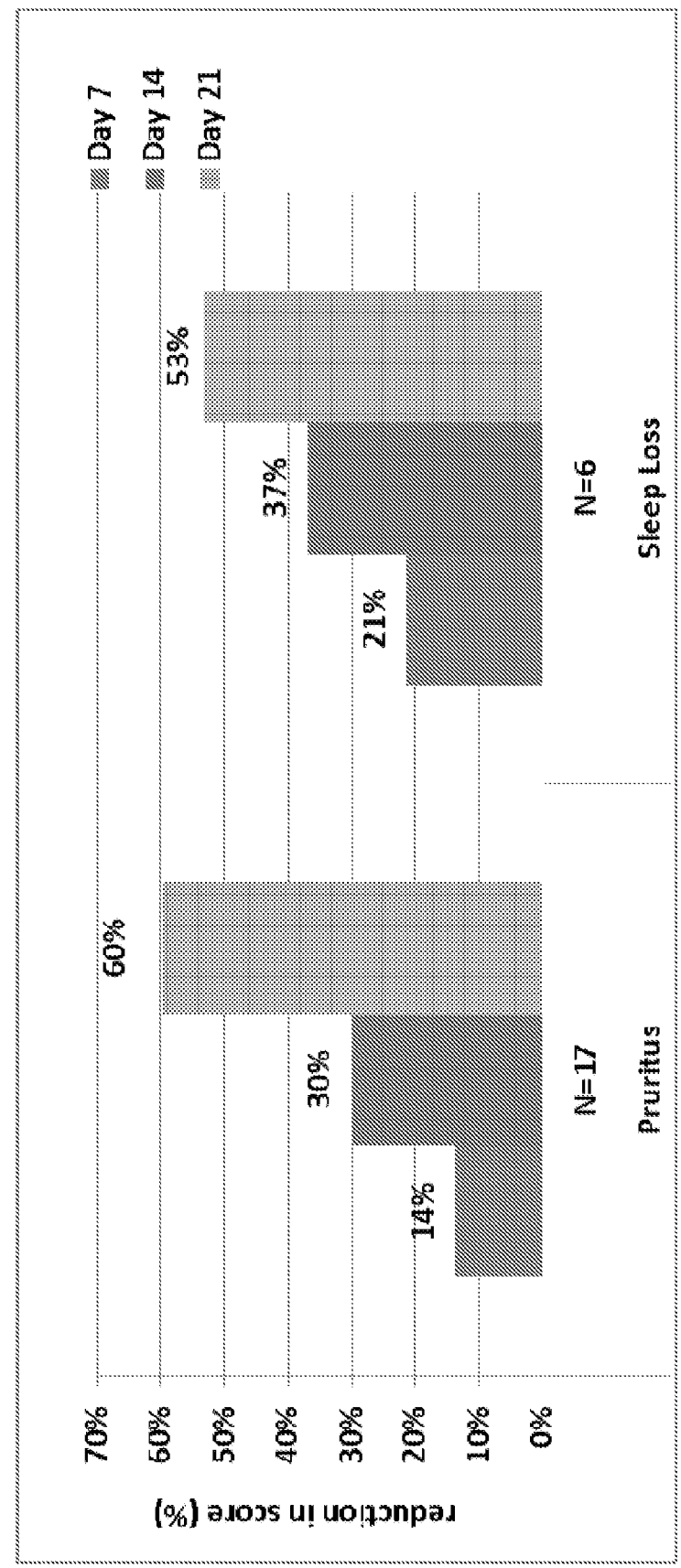
FIG. 27 is a bar graph depicting reduction in pruritus and sleep loss in the treatment group (on days 7, 14 and 21).

In the treatment group, significance was reached in reduction of both pruritus and sleep loss (see FIG. 27, p<0.001). Furthermore, the baseline mean score for sleep loss was higher compared to the carrier group (mean=2.6).

Figure 28:
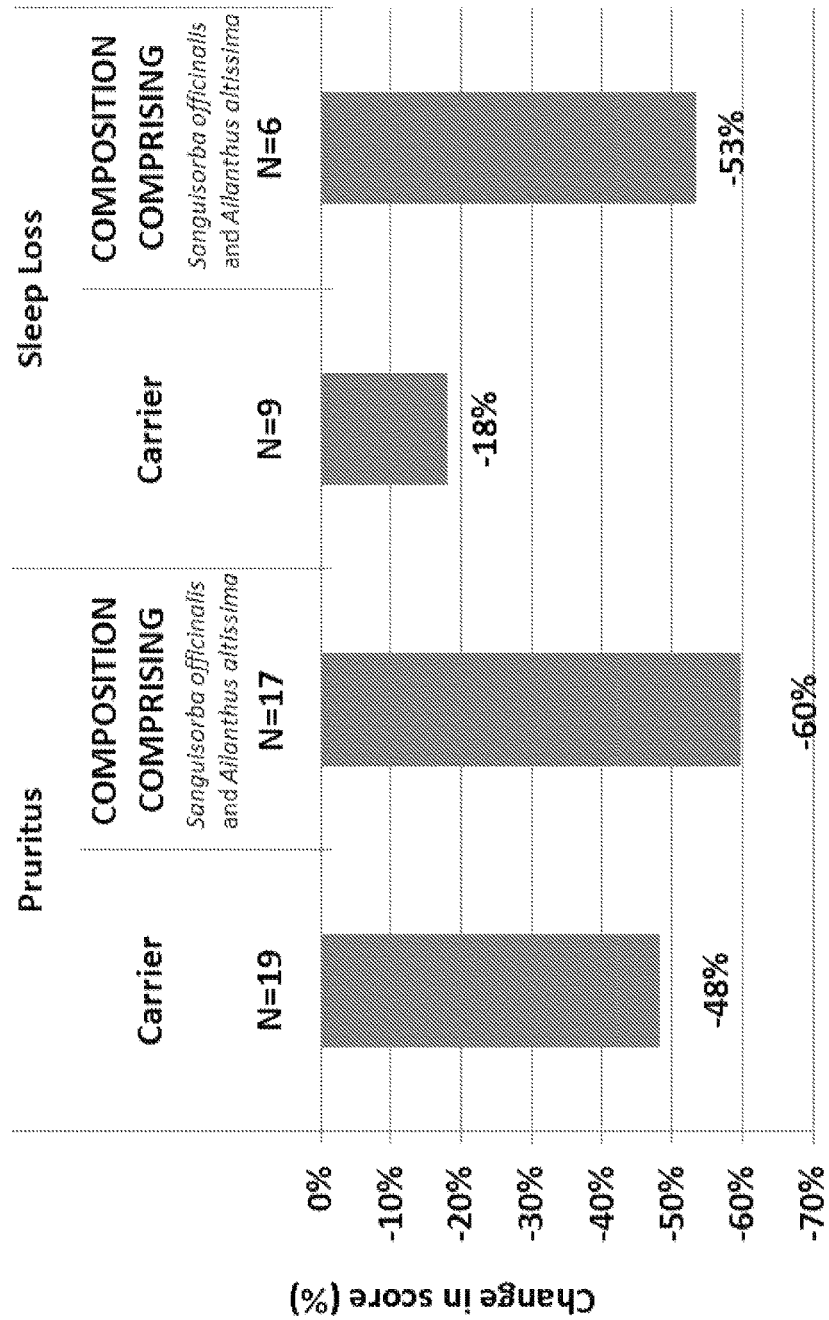
FIG. 28 is a bar graph depicting an improvement in subjective assessment of pruritus and insomnia after 21 days in the carrier and treatment groups.

When compared, no significance was found between itching and reduction in sleep loss between the two groups after 21 days (see FIG. 28). In spite of a higher mean decline of sleep loss in the treatment group, the small sample size played a limiting role for reaching the significant difference.

As both treatment and carrier treated group exhibited significant reduction in pruritus without any significant

TABLE 15

A comparison between the change in symptom intensity in carrier and treatment groups after 21 days of treatment

|                  | Erythema | Oedema | Oozing | Excoriation | Lichenifiction | Dryness |
|------------------|----------|--------|--------|-------------|----------------|---------|
| Carrier group    | 34%      | 27%    | 39%    | 23%         | 28%            | 34%     |
| Treatment group  | 37%      | 50%    | 86%    | 53%         | 53%            | 40%     |
| P <              | NS       | 0.02   | 0.001  | 0.003       | 0.03           | NS      | change between the two groups, the ability of the lotions to reduce pruritus was thus regarded as based mainly on the carrier activity.

Effect of the Treatment on Severe AD

Changes in SCORAD was analyzed in sub-populations of AD subjects with severe (SCORAD>50) and non-severe (mild to moderate, SCORAD<50) appearance of the condition at baseline visit.

Figure 29:
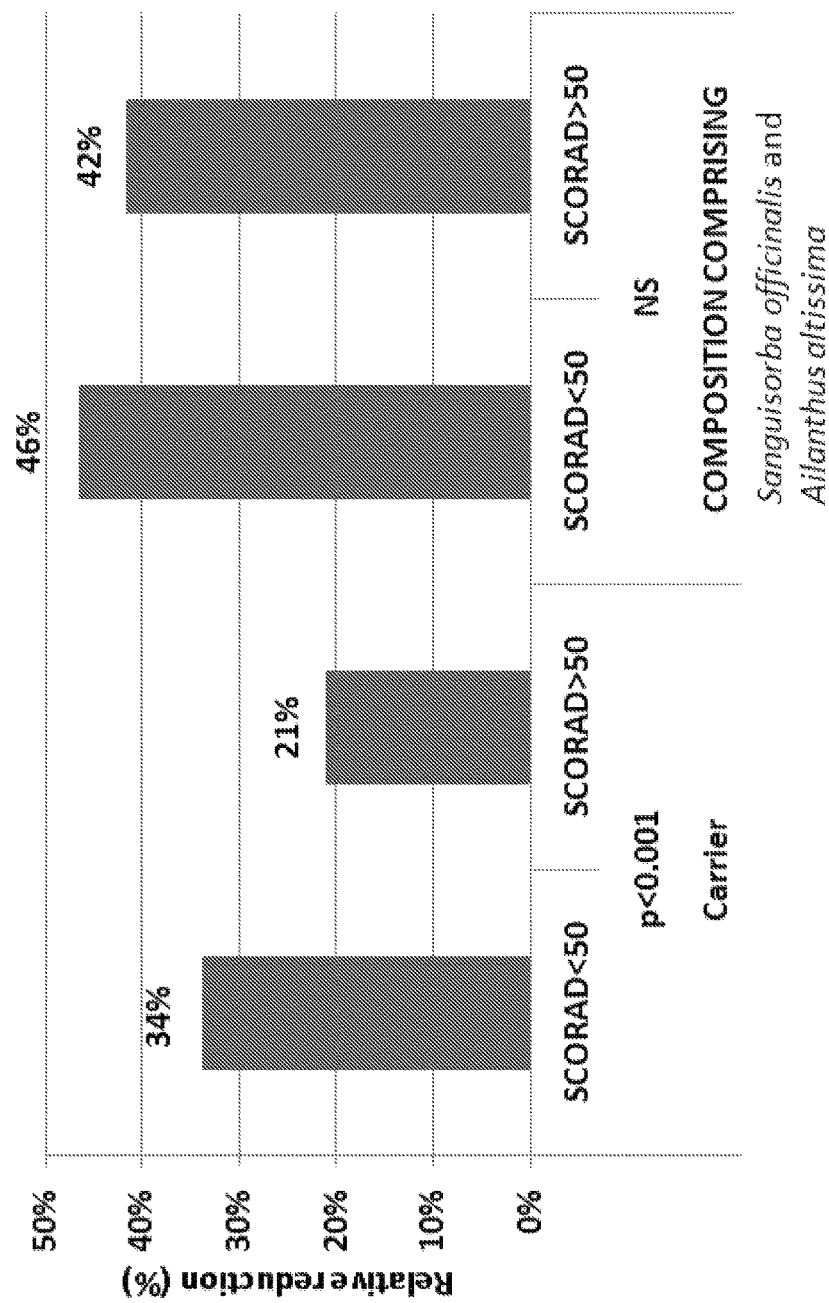
FIG. 29 is a bar graph depicting SCORAD reduction in severe and non-severe AD after 21 days in the carrier and treatment groups.

When comparing the effectiveness of the lotions in treating mild to moderate (SCORAD<50) AD patients, the efficacy of treatment body lotion was 35% higher than carrier (46% versus 34%), while the efficacy of treatment body lotion in treating severe AD (SCORAD>50), typically accompanied by secondary infections, was as much as 50% higher than the carrier (42% versus 21%, see FIG. 29).

Taken together, the results show clearly superior effect of treatment body lotion on AD symptoms, particularly on symptoms related to severe AD and to secondary infections.

Moisturizing Level

Moisturizing level is an indication for the ability of lotion to provide a mechanical barrier and to maintain humidity of the skin. It was tested by 2 methods:

TEWL—measurement of the evaporation through the skin

Skin Hydration—the quantity of liquid which is retained in the skin.

The measurements were conducted on baseline visit and on day 21.

Figure 30:
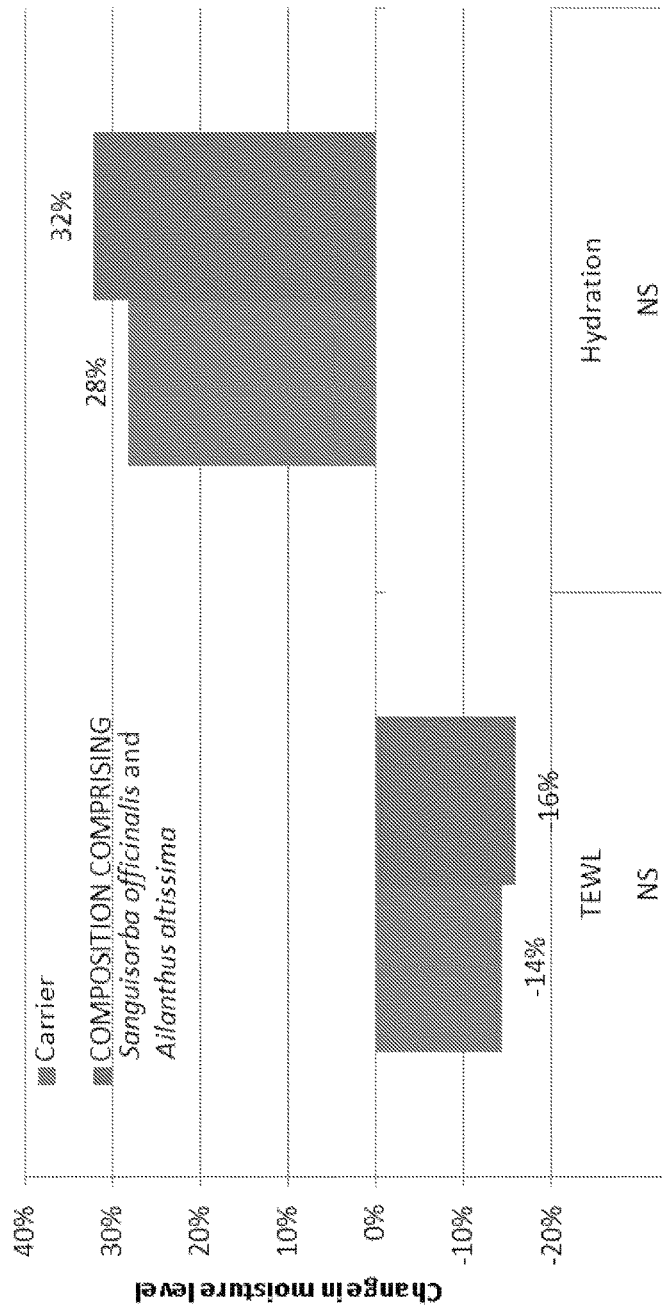
FIG. 30 is a bar graph depicting skin hydration and Transepithelial Water Loss (TEWL) in the carrier and treatment groups.

The results demonstrated the significant differences between baseline and day 21 measurements of the skin moisture in both groups (see FIG. 30, p<0.001). Both lotions improved the skin moisture to the same extent.

Example 11

Human Beta-defensin 3 Stimulating Active Component Characterization from *Ailanthi radicis*

Classical bioassay-guided fractionation has been generally recognized as a tedious and laborious process in the study of natural products chemistry field. In the past decade, more effective strategies for tracking biologically and pharmacologically active natural products has been developed with the improvement of analytical technique including HPLC-coupled activity profiling. This technique with HPLC has been known as an efficient miniaturized approach which is directly applicable to mechanism and cell-based assay.

Materials and Experimental Procedures

HaCaT cell culture: Human keratinocytes (HaCaT) were cultured in DEMD media containing 10% fetal bovine serum (FBS) and antibiotics/antimycotics (penicillin G, streptomycin, amphotericinB), at 37.0° C. and 5% $CO_2$.

Preparation of *Ailanthi radicis* extract: The dried *Ailanthi radicis* were extracted with boiling water for 3 hrs and the hot water extract was freeze-dried at −60° C. at reduced pressure. The freeze-dried extact was suspended in $H_2O$ and successively partitioned with ethyl acetate (EtOAc), butyl alcohol (n-BuOH). All were stored at −20° C.

Real-time PCR Analysis

Total RNA was extracted from keratinocytes using TRIzol reagent (Invitrogen Life Technologies) according to the manufacturer's instructions. First-strand cDNA was synthesized from 3 µg of total RNA with oligo(dT)12-18 primers using SuperScript II RNase H reverse transcriptase (Invitrogen Life Technologies). Furthermore, to remove RNA complementary to the cDNA, 2 U of RNase H (Invitrogen Life Technologies) was added to the reaction mixtures, which were then incubated at 37° C. for 20 min. Real-time quantitative PCR was performed using the TaqMan Universal PCR Master Mix (Applied Biosystems). Amplification and detection of human beta defensin 3 mRNA were analyzed by a real-time PCR system (model 7500; Applied Biosystems), according to the manufacturer's instructions. The human beta-defensin 3 primer/probe set was obtained from Applied Biosystems (Assays on-Demand, Hs0015557_ml). PCR was performed as follows: one initial step at 50° C. for 2 min and 95° C. for 10 min was followed by 40 cycles at 95° C. for 15 s and 60° C. for 1 min. To standardize IL-18 mRNA concentrations, transcript levels of the housekeeping gene GAPDH were determined in parallel for each sample, and relative IL-18 transcript levels were corrected by normalization based on the GAPDH transcript levels. For GAPDH, inventors used a pre-developed assay (Applied Biosystems). All real-time PCRs were performed in triplicate. Changes in gene expression were reported as fold increases relative to untreated controls.

Figure 31:
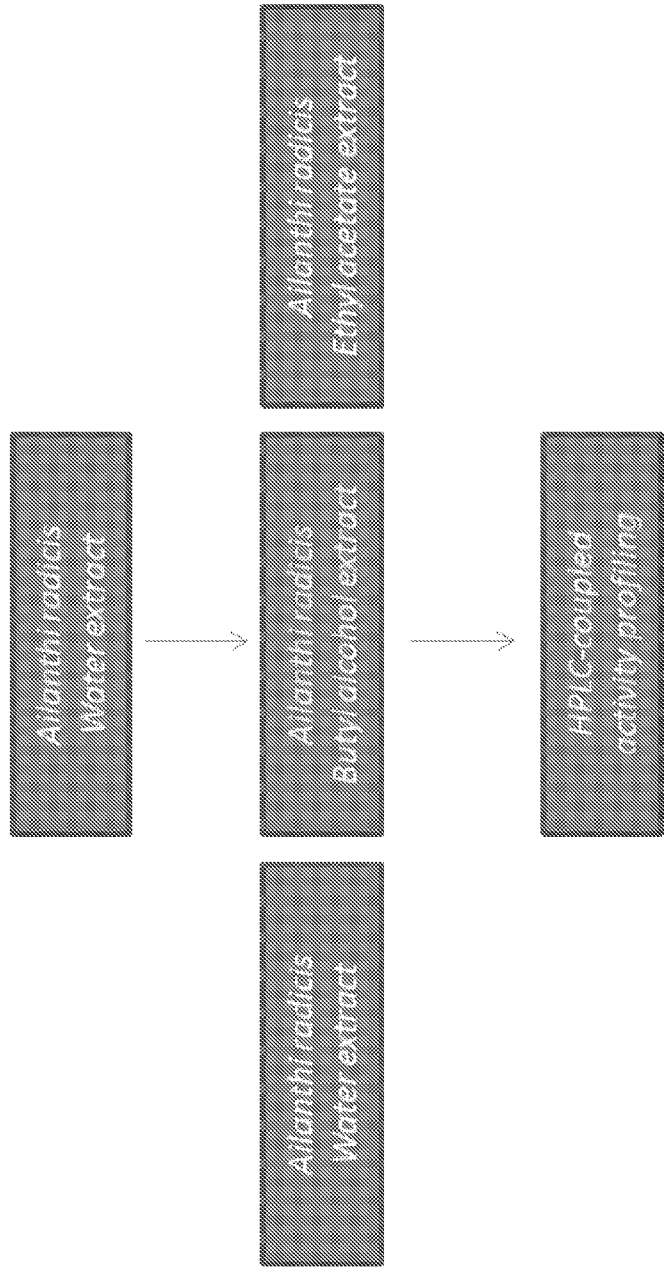
FIG. 31 is a flow diagram illustrating serial fractionations from *Ailanthi radicis*.

Serial Fractionation: The serial fractionation from *Ailanthi radicis* was done as described in FIG. 31.

Results

Among the herbal mixtures, *Ailanthi radicis* extract was originally chosen because of its strong human beta-defensin 3 stimulating activity. Therefore, the present inventors characterized active component responsible for stimulation of human beta defensin 3 (DEF3) in the human keratinocyte cell line, HaCaT using traditional fractionation technique and HPLC-coupled activity profiling in combination with real-time PCR. To identify molecular structure of active components, mass spectroscopy and NMR spectroscopy were used.

Step I: Preparation of Three Types of Solvent-based Fractionations from *Ailanthi radicis* Hot Water Extracts From hot water extracts of *Ailanthi radicis*, 3 kinds of extractions were prepared for the first stage, namely: 1. *Ailanthi radicis* water extract, 2. *Ailanthi radicis* butyl alcohol extract, and 3. *Ailanthi radicis* ethyl acetate extract (FIGS. 32A-E). All fractions were freeze-dried and re-dissolved in water (in the case of *Ailanthi radicis* water extract) and DMSO (in the case of *Ailanthi radicis* butyl alcohol extract and ethyl acetate extract) at the concentration of 10 mg/ml. After treatment, 10 µl of each extract was added to a HaCaT cell culture at a final concentration of 100 µg/3 ml of culture media in 6 well flask for 48 hrs. The changes in human beta-defensin 3 mRNA were compared with water or DMSO control groups by means of real-time PCR analysis.

The relative expression changes of GAPDH (as internal control) and DEF3 in all tested groups are illustrated in Table 16, below. When compared with relative expression changes between GAPDH and DEF3, *Ailanthi radicis* ethyl acetate extract and *Ailanthi radicis* butyl alcohol extract significantly increased the expressions.

TABLE 16

Relative expression of DEF3 from solvents-based fractions from *Ailanthiradicis* hot water extracts

| Group | Delta Ct between GAPDH and DEF3 (Ct of DEF3-Ct of GAPDH) | Expression changes (folds) when compared with control groups |
|---|---|---|
| D.W. control | 16.57 | — |
| *Ailanthiradicis* water extract | 15.52 | $2^{(16.57-15.52)}$ |

TABLE 16-continued

Relative expression of DEF3 from solvents-based fractions from *Ailanthiradicis* hot water extracts

| Group | Delta Ct between GAPDH and DEF3 (Ct of DEF3-Ct of GAPDH) | Expression changes (folds) when compared with control groups |
| --- | --- | --- |
| DMSO control | 17.31 | — |
| *Ailanthiradicis* ethyl acetate | 12.84 | $2^{(17.31-12.84)}$ |
| *Ailanthiradicis* butyl alcohol | 12.8 | $2^{(17.31-12.23)}$ |

Figure 33:
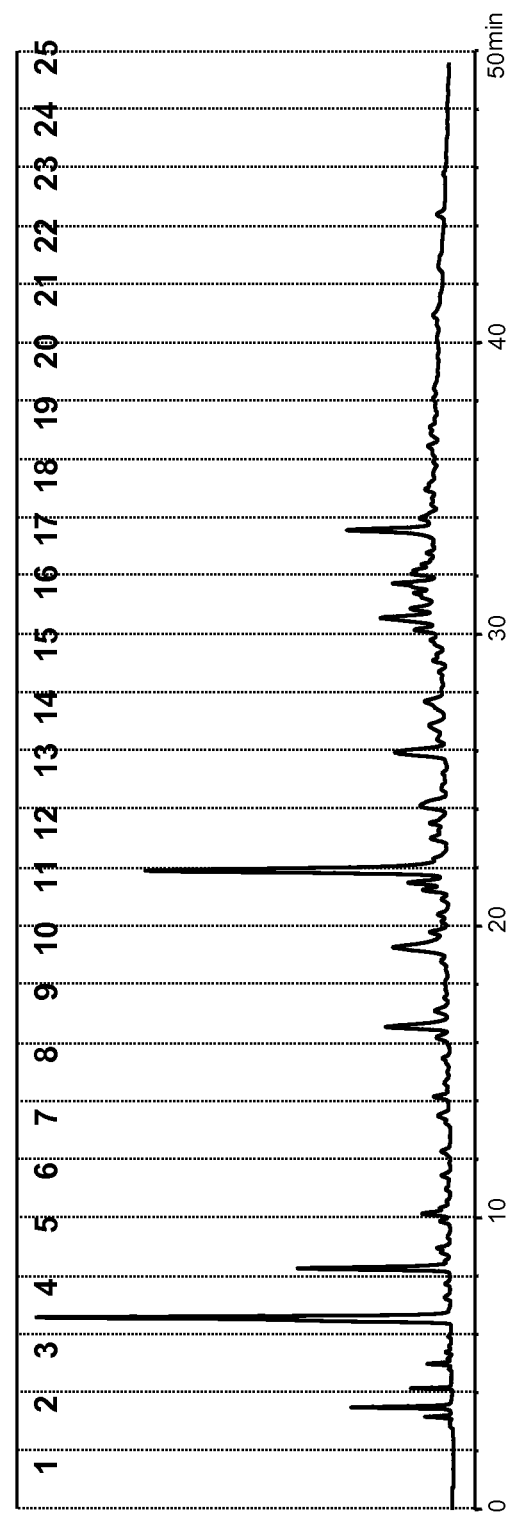
FIG. 33 is a chromatogram obtained by gradient HPCL from *Ailanthi radicis* butyl alcohol extract.

Step II: HPLC-based 25 Kinds of Fractionations from *Ailanthi radicis* butyl Alcohol extract The freeze-dried product (49 g) was successively partitioned with EtOAc, n-BuOH, and $H_2O$. The active extract of n-BuOH (2.1 g) was stored at −20° C. For activity profiling, a portion (177 mg) of the from *Ailanthi radicis* butyl alcohol extract was fractionated using a semi-preparative HPLC at regular intervals of 2 min, based on the following condition: initiation with 90% H2O containing 0.1% HCOOH/10% MeOH, followed by a gradient to 40% H2O containing 0.1% HCOOH/60% MeOH for 50 min, at a flow rate of 4.0 ml/min and UV detection at 254 nm. A total of 25 fractions was collected (FIG. 33 and Table 17, below).

Each 25 fractions were pooled, freeze-dried and re-dissolved in DMSO at the concentration of 10 mg/ml. After treatment, 10 µl of each extract was added to HaCaT cell culture at a final concentration of 100 µg/3 ml of culture media in 6 well flask for 48 hrs, the changes in human beta-defensin 3 mRNA were compared with water or DMSO control groups by means of real-time PCR analysis.

TABLE 17

Number and weights from HPLC-based 25 fractions from *Ailanthiradicis* butyl alcohol extract

| No. | Net weight of each fraction |
| --- | --- |
| 1 | 0.4 mg |
| 2 | 1.6 mg |
| 3 | 0.7 mg |
| 4 | 0.5 mg |
| 5 | 0.8 mg |
| 6 | 0.6 mg |
| 7 | 1.7 mg |
| 8 | 1.9 mg |
| 9 | 0.6 mg |
| 10 | 0.3 mg |
| 11 | 0.6 mg |
| 12 | 0.8 mg |
| 13 | 0.8 mg |
| 14 | 0.9 mg |
| 15 | 0.6 mg |
| 16 | 1.2 mg |
| 17 | 0.2 mg |
| 18 | 0.9 mg |
| 19 | 0.9 mg |
| 20 | 0.6 mg |
| 21 | 1.6 mg |
| 22 | 0.7 mg |
| 23 | 0.9 mg |
| 24 | 0.7 mg |
| 25 | 0.3 mg |

Figure 34:
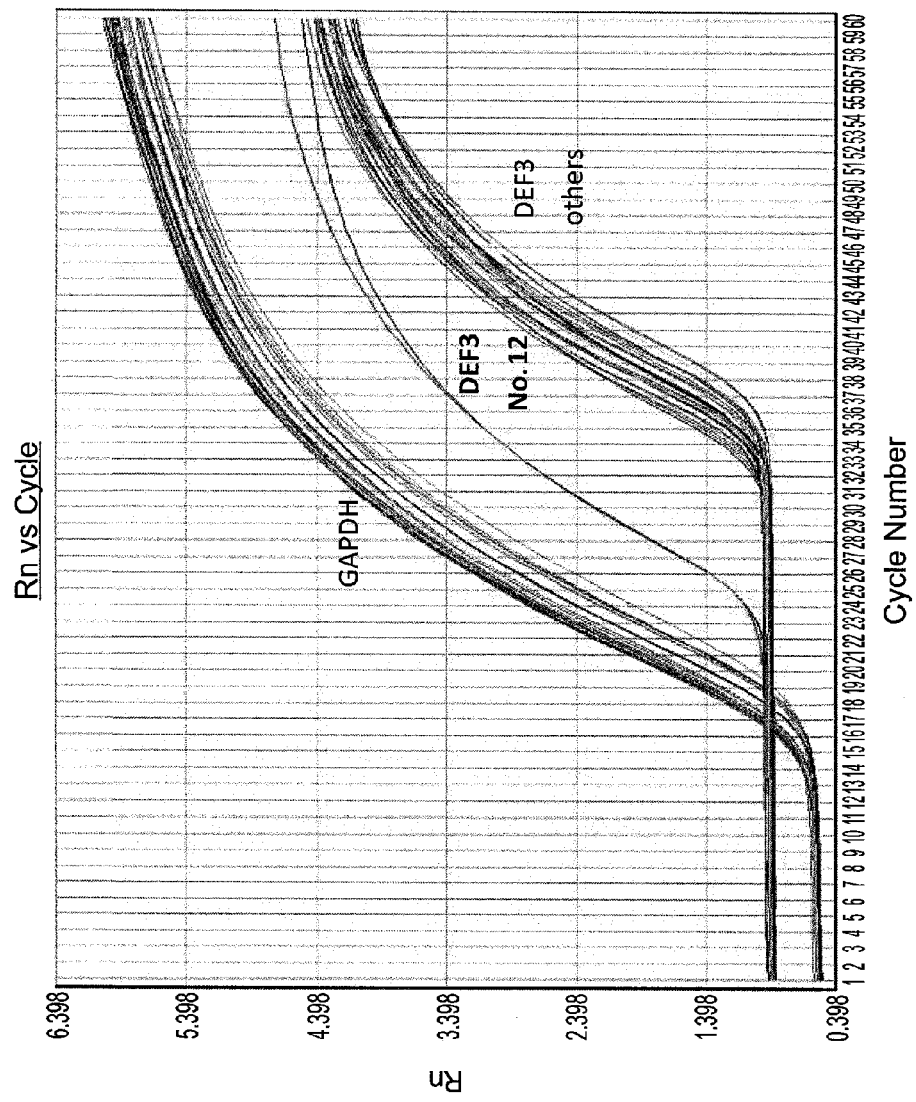
FIG. 34 is a line graph depicting real-time PCR analysis on the expression of DEF3 after treatment with each of the 25 fractions
Figure 35:
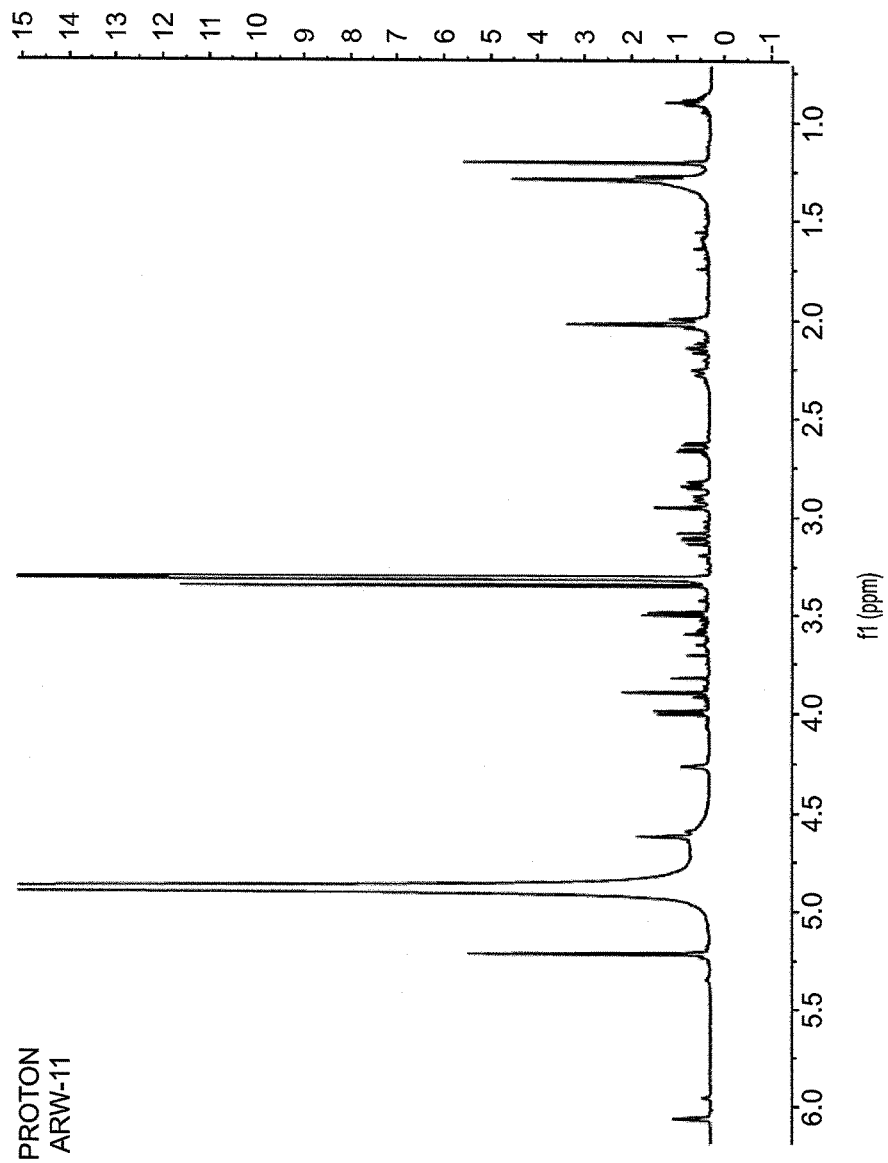
FIG. 35 is a NMR spectrum of DEF3-stimulating compound from *Ailanthi radicis* extract.
Figure 36:
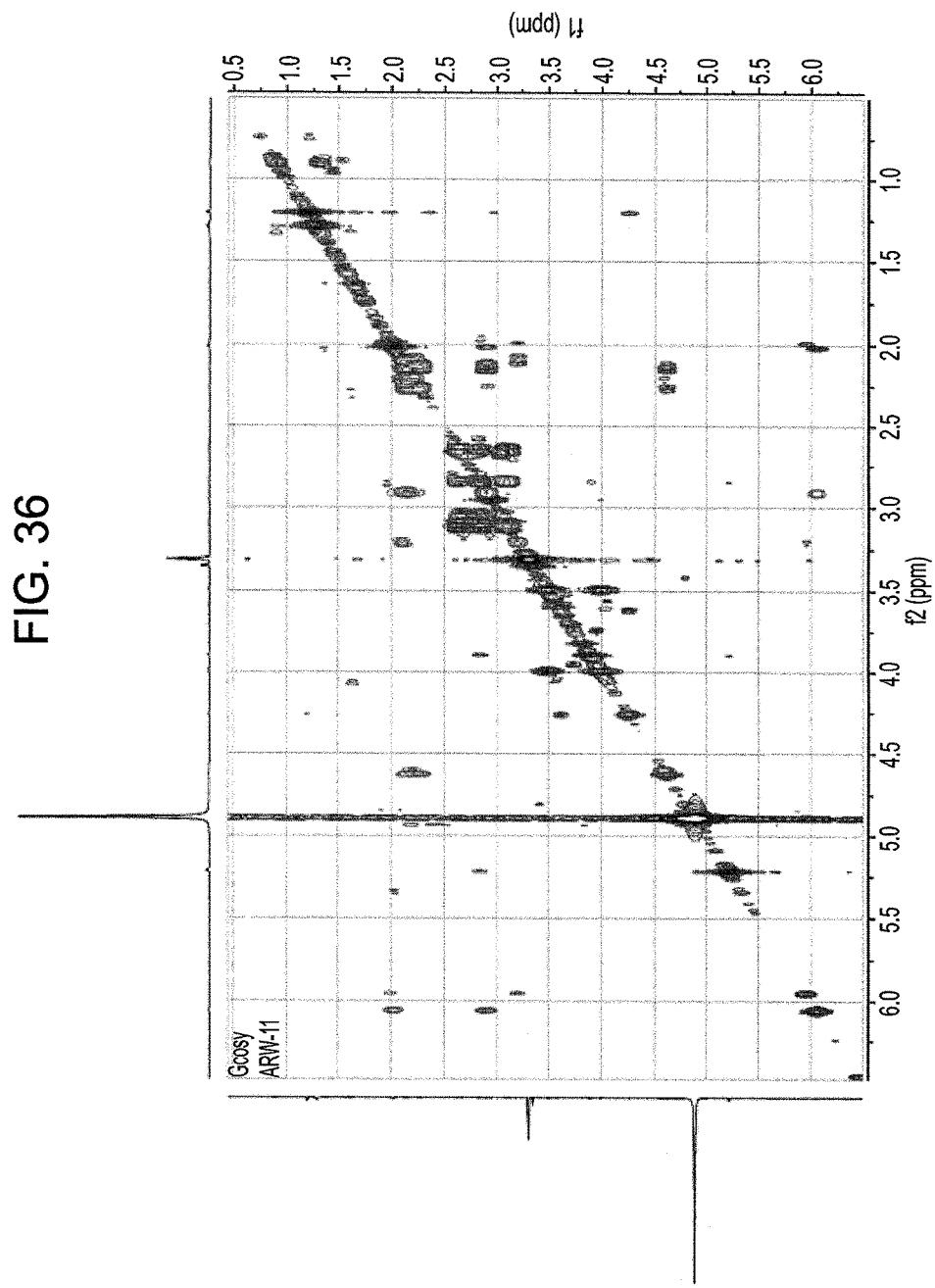
FIG. 36 is a NMR spectrum of DEF3-stimulating compound from *Ailanthi radicis* extract.
Figure 37:
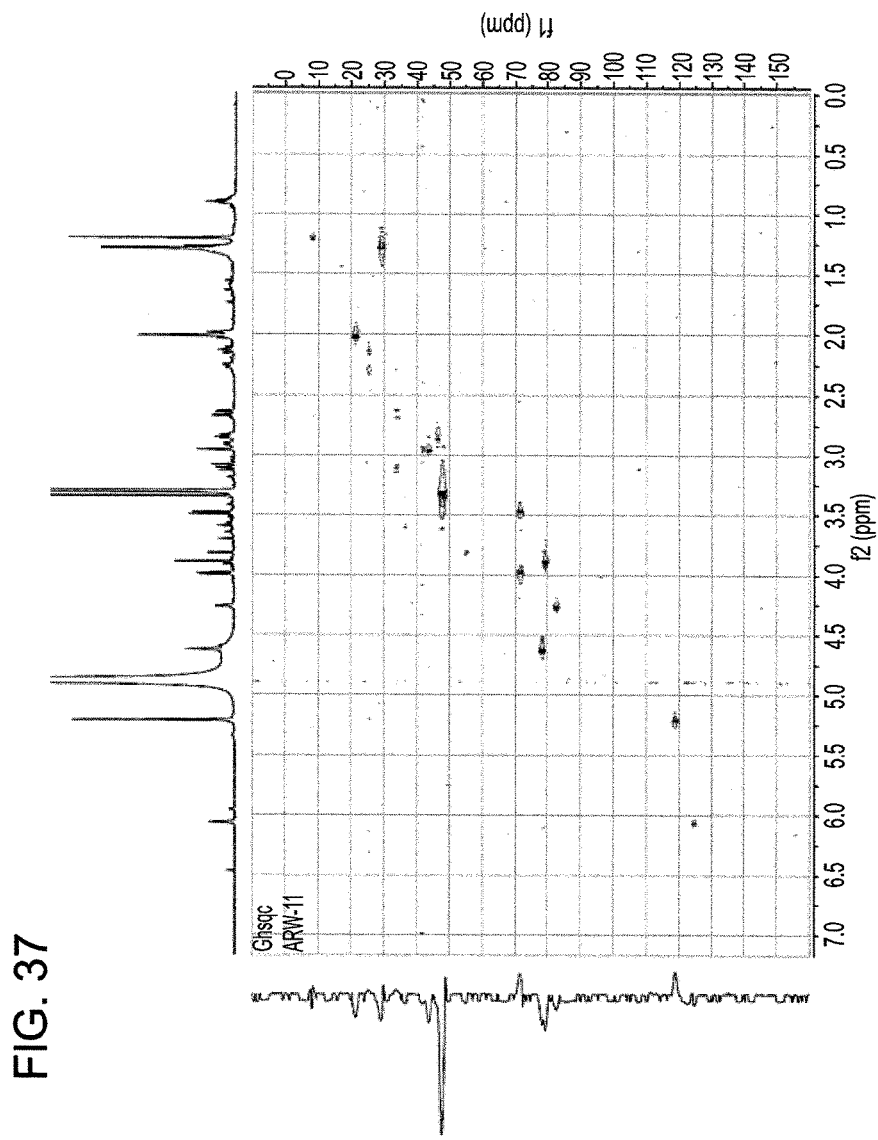
FIG. 37 is a NMR spectrum of DEF3-stimulating compound from *Ailanthi radicis* extract.
Figure 38:
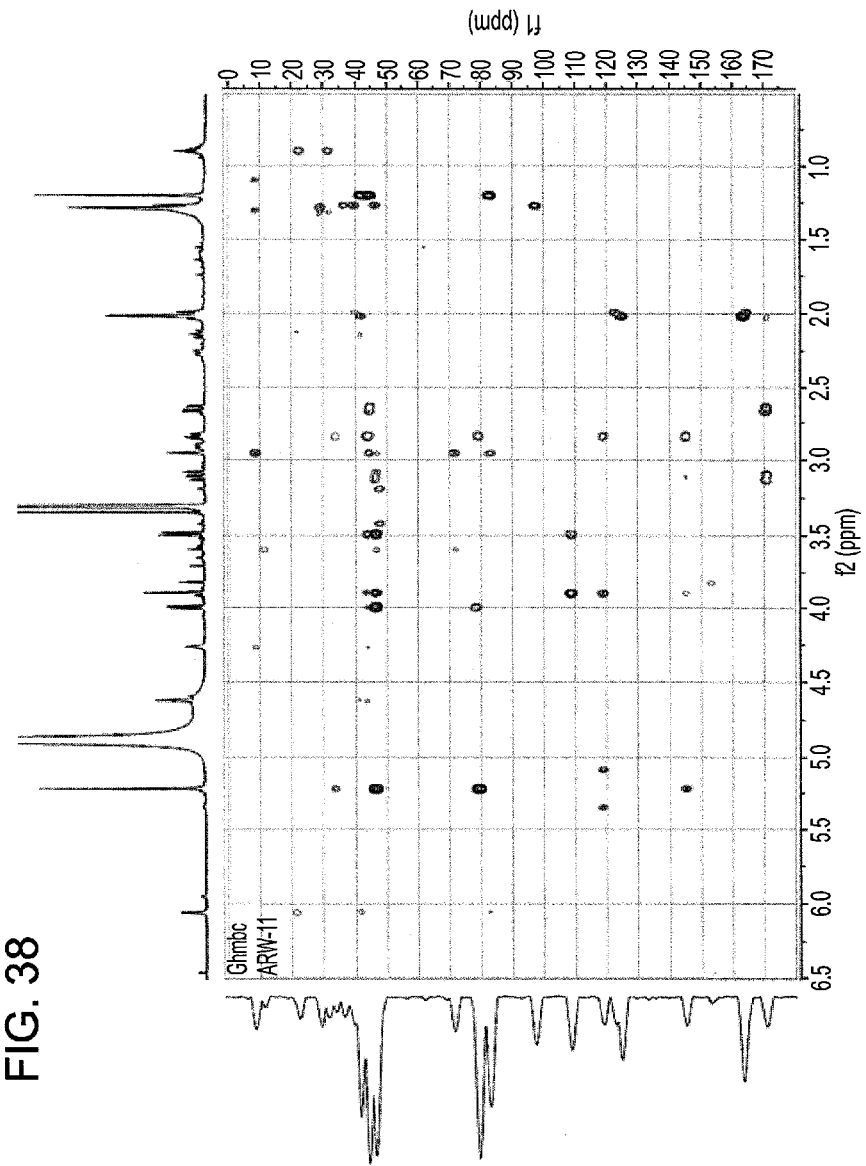
FIG. 38 is a NMR spectrum of DEF3-stimulating compound from *Ailanthi radicis* extract.

The relative expression changes of GAPDH (as internal control) and DEF3 in all tested groups is illustrated in FIG. 34. When compared with relative expression changes between GAPDH and DEF3, fraction number 12 dramatically increased the expression of DEF3 in human keratinocyte cell line, HaCaT.

Step III: Structure Characterization by NMR and Mass Spectroscopy from Fraction No. 12.

Isolation of DEF3-Stimulating Compound: To isolate active compounds from the n-BuOH extract, an aliquot (1.07 g) of the extract was repeatedly separated under the same HPLC condition with the above activity profiling to give an active fraction containing DEF3-stimulating compound. This compound was further purified in a gradient solvent system, 80% $H_2O$ containing 0.1% HCOOH/20% MeOH to 70% $H_2O$ containing 0.1% HCOOH/30% MeOH for 70 min ($t_R$: 24.70 min, 2.2 mg).

NMR Structure Analysis: $^1H$, $^{13}C$, and 2D-NMR experiments were recorded using either a Varian VNMRS 600 MHz NMR spectrometer. LC/$^1H$ NMR was performed on a Varian VNMRS 600 MHz NMR spectrometer ($^1H$, 600.006 MHz) hyphenated to a Varian ProStar HPLC system using a 150 µL triple-resonance microflow cryogenic probe. 1D$^1H$ NMR spectra were obtained both in the stop-flow mode and continuous-flow mode. For the stop-flow mode $^1$HNMR, the HPLC method was initially performed with 95% $D_2O$ containing 0.1% HCOOH/5% ACN, followed by a gradient to 35% $D_2O$ containing 0.1% HCOOH/65% ACN over 35 min (total run time 45 min), with a flow rate of 1.0 ml/min and UV detection at 280 nm. The sample (50 µL) was injected on to a SunFire™ C18 (5 µm, 4.6×150 mm, Waters) reversed phase column. The standard WET1D sequence was used for the pre-saturation of $^1H$ frequency in the HOD, ACN, and HCOOH. Data were acquired with 9 kHz sweep width using 33 K time domain points with an acquisition time of 1.82 second. Variable numbers of scans (128-512) were used upon the relative concentration of the each compound within the probe flow cell. $^1H$ NMR spectra were referenced to the ACN resonance (1.96 ppm). The continuous-flow LC-NMR experiment was performed under the same gradient condition except the flow rate of 0.2 mL/min and total run time of 180 min. $^1H$ NMR spectra were collected by 32 scans each continuously during the chromatographic elution.

The $^1H$ NMR spectra showed two methyl proton signals of H-18 and H-19 (each 3H, s) at δ 1.20 and 2.02, and also exhibited an olefinic proton H-3 (1H, br s) at δ 6.06 and an exomethylene proton H-21 (2H, s) signals. Three oxygenated methine proton signals, H-1, H-7 and H-12 was respectively observed at δ 4.26 (1H, s), 4.62 (1H, t, 2.4) and δ 3.89 (1H, s). In addition, three methine proton signals at δ 2.91 (H-5), 2.95 (H-9), and δ 2.84 (H-14) were shown in the spectrum together with three methylene proton signals at δ 2.27, 2.14 (H-6α and H-6β), 2.65, 3.11 (H-15α and H-15β), and δ 3.99, 3.49 (H-20α and H-20β). The γ-lactone and α,β-unsaturated carbonyl signals were detected at δ 170.6 (H-16) and 197.6 (H-2), respectively. Its HMBC spectrum revealed that an isolated methyl of H-19 was correlated with three carbonyl carbons of C-1, C-5, and C-10, and the methine proton signal H-14 showed long-range correlation with carbon signals of C-10, C-12, C-13, C-15, and C-20. The $^1H$, $^{13}C$, COSY and HMBC NMR data of DEF3-stimulating compound were shown in the Table 18 in detail. The NMR spectrums of DEF3-stimulating compounds are illustrated in FIGS. 35-38. Based on NMR structure analysis, the DEF3-stimulating compound from *Ailanthi radicis* extract was identified as ailanthone (FIGS. 39A-B).

TABLE 18

¹H and ¹³C NMR data for DEF3-stimulating compound

| Position | $\delta_C$ | $\delta_H$ | COSY | HMBC (H→C) |
|---|---|---|---|---|
| 1 | 82.8 | 4.26 (1H, s) | H-19 | C-10, 19 |
| 2 | 197.6 | — | | |
| 3 | 124.7 | 6.06 (1H, br s) | H-5, 18 | C-1, 5, 18 |
| 4 | 163.5 | — | | |
| 5 | 41.8 | 2.91 (1H, br d, 12.3) | H-3, 6α, 6β, 18 | |
| 6α | 25.3 | 2.27 (1H, br d, 15.0) | H-5, 7 | |
| 6β | | 2.14 (1H, ddd, 15.0, 12.3, 2.4) | H-5, 7 | C-5 |
| 7 | 78.4 | 4.62 (1H, t, 2.4) | H-6β | C-5, 9 |
| 8 | 47.0 | — | | |
| 9 | 43.8 | 2.95 (1H, s) | | C-1, 8, 10, 20 |
| 10 | 44.4 | — | | |
| 11 | 108.6 | — | | |
| 12 | 79.4 | 3.89 (1H, s) | H-14 | C-10, 11, 13, 14, 21 |
| 13 | 145.1 | — | | |
| 14 | 46.5 | 2.84 (1H, dd, 13.8, 5.4) | H-12, 15α, 15β, 21 | C-10, 12, 13, 15, 20 |
| 15α | 33.9 | 2.65 (1H, dd, 5.4, 18.6) | H-14, 15β | C-14, 16 |
| 15β | | 3.11 (1H, dd, 13.8, 18.6) | H-14, 15α | C-13, 14, 16 |
| 16 | 170.6 | — | | |
| 17 | — | — | | |
| 18 | 21.2 | 2.02 (3H, s) | H-3, 5 | C-3, 4, 5 |
| 19 | 8.3 | 1.20 (3H, s) | H-1 | C-1, 5, 10 |
| 20α | 71.6 | 3.99 (1H, d, 8.1) | H-20β | C-7, 10, 14 |
| 20β | | 3.49 (1H, d, 8.1) | H-20α | C-10, 11, 14 |
| 21 | 118.9 | 5.22 (2H, s) | H-14 | C-12, 13, 14, 15 |

NMR data were observed at 600 (¹H) MHz in MeOH-d₄ (δ in ppm, J in Hz).
¹³C NMR data were deduced by the 2D NMR experiments including HSQC and HMBC.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating atopic dermatitis in a subject in need thereof, the method comprising administering to the subject a therapeutically effective amount of a composition comprising 0.5-2.0 (v/v) water extracts of each of *Rheum palmatum, Cnidium Monnieri, Scutellaria baicalensis, Sanguisorbae officinalis,* and *Ailanthus altissima,* wherein the extracts are produced by water extraction and further purified using a resin chromatography comprising macroporous resin.

2. The method of claim 1, wherein said administering effectively downregulates secretion of a Th2 type cytokine selected from the group consisting of IL-4, IL-5, IL-6, IL-10 and IL-13 in a cell of said subject.

3. The method of claim 1, wherein said administering effectively upregulates expression of a human beta-defensin in a cell of said subject.

4. The method of claim 1, wherein the composition further comprises one or more of a *Galla rhois gallnut* plant extract, *Peucedanum praeruptorum* plant extract, *Silybum marianum* plant extract and Dipotassium Glycyrrhizate.

* * * * *